(12) United States Patent
Wilson et al.

(10) Patent No.: US 8,158,637 B2
(45) Date of Patent: *Apr. 17, 2012

(54) QUINAZOLINES USEFUL AS MODULATORS OF VOLTAGE GATED ION CHANNELS

(75) Inventors: Dean Wilson, Bedford, MA (US); Lev T. D. Fanning, San Marcos, CA (US); Paul Krenitsky, San Diego, CA (US); Andreas Termin, Encinitas, CA (US); Pramod Joshi, San Diego, CA (US); Urvi Sheth, San Diego, CA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1098 days.

This patent is subject to a terminal disclaimer.

(21) Appl. No.: 11/598,576

(22) Filed: Nov. 13, 2006

(65) Prior Publication Data

US 2008/0221137 A1    Sep. 11, 2008

Related U.S. Application Data

(60) Provisional application No. 60/737,330, filed on Nov. 14, 2005.

(51) Int. Cl.
*A01N 43/54* (2006.01)
*A61K 31/517* (2006.01)
*C07D 239/72* (2006.01)

(52) U.S. Cl. .................. 514/266.1; 544/293

(58) Field of Classification Search ............ 514/266.1; 544/293
See application file for complete search history.

(56) References Cited

U.S. PATENT DOCUMENTS

| 7,678,802 | B2 | 3/2010 | Gonzalez, III et al. |
|---|---|---|---|
| 7,713,983 | B2 | 5/2010 | Gonzalez, III et al. |
| 7,718,658 | B2 | 5/2010 | Wilson et al. |
| 2004/0248890 | A1 | 12/2004 | Gonzalez, III et al. |
| 2006/0154935 | A1 | 7/2006 | Wilson et al. |
| 2006/0166963 | A1 | 7/2006 | Silva et al. |
| 2006/0173018 | A1 | 8/2006 | Wilson et al. |
| 2006/0217377 | A1 | 9/2006 | Gonzalez, III et al. |
| 2008/0167305 | A1* | 7/2008 | Wilson et al. ........... 514/234.2 |
| 2009/0312342 | A1 | 12/2009 | Wilson et al. |
| 2010/0160316 | A1 | 6/2010 | Gonzalez, III et al. |

FOREIGN PATENT DOCUMENTS

| WO | 2004078733 | 9/2004 |
|---|---|---|
| WO | 2006028904 | 3/2006 |

OTHER PUBLICATIONS

International Search Report, PCT/US2006/043895.

* cited by examiner

*Primary Examiner* — Paul V. Ward
(74) *Attorney, Agent, or Firm* — Nancy K. Brennan

(57) ABSTRACT

The present invention relates to compounds useful as inhibitors of voltage-gated sodium channels. The invention also provides pharmaceutically acceptable compositions comprising the compounds of the invention and methods of using the compositions in the treatment of various disorders.

18 Claims, 1 Drawing Sheet

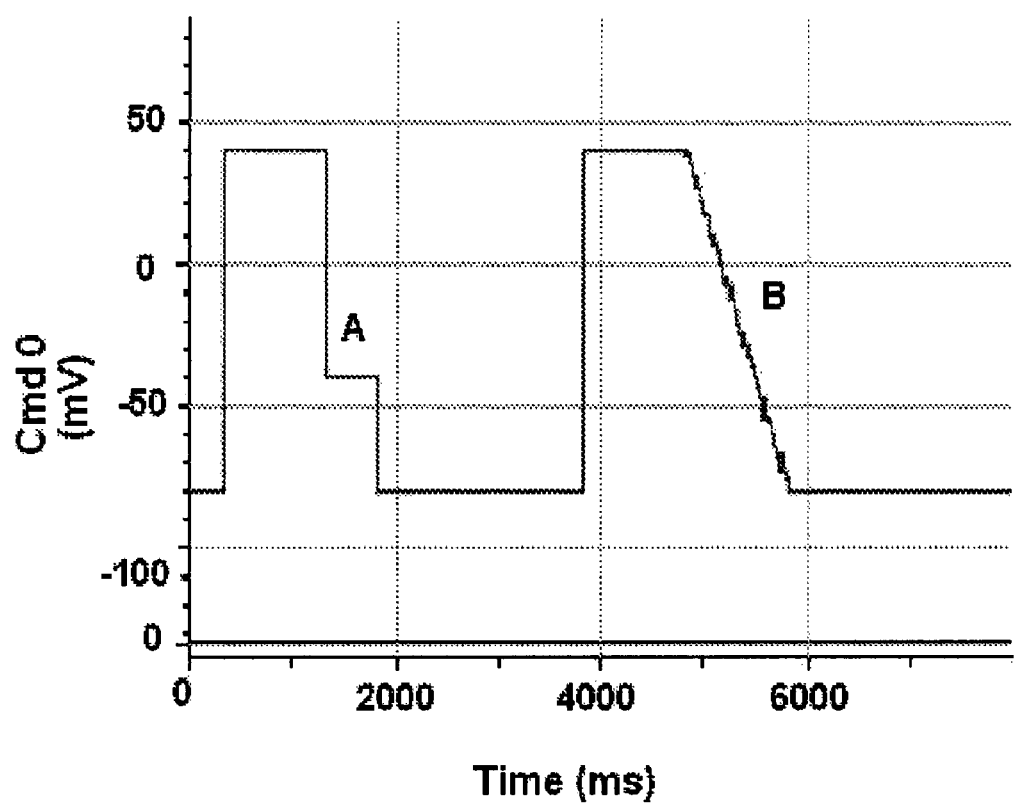

QUINAZOLINES USEFUL AS MODULATORS OF VOLTAGE GATED ION CHANNELS

CROSS-REFERENCE TO RELATED APPLICATIONS

This application claims the benefit under 35 U.S.C. §119 of U.S. Provisional application Ser. No. 60/737,330 filed Nov. 14, 2005, the entire contents of which is incorporated herein by reference.

TECHNICAL FIELD OF THE INVENTION

The present invention relates to compounds useful as inhibitors of ion channels. The invention also provides pharmaceutically acceptable compositions comprising the compounds of the invention and methods of using the compositions in the treatment of various disorders.

BACKGROUND OF THE INVENTION

Na channels are central to the generation of action potentials in all excitable cells such as neurons and myocytes. They play key roles in excitable tissue including brain, smooth muscles of the gastrointestinal tract, skeletal muscle, the peripheral nervous system, spinal cord and airway. As such they play key roles in a variety of disease states such as epilepsy (See, Moulard, B. and D. Bertrand (2002) "Epilepsy and sodium channel blockers" *Expert Opin. Ther. Patents* 12(1): 85-91)), pain (ee, Waxman, S. G., S. Dib-Hajj, et al. (1999) "Sodium channels and pain" *Proc Natl Acad Sci USA* 96(14): 7635-9 and Waxman, S. G., T. R. Cummins, et al. (2000) "Voltage-gated sodium channels and the molecular pathogenesis of pain: a review" *J Rehabil Res Dev* 37(5): 517-28), myotonia (See, Meola, G. and V. Sansone (2000) "Therapy in myotonic disorders and in muscle channelopathies" *Neurol Sci* 21(5): S953-61 and Mankodi, A. and C. A. Thornton (2002) "Myotonic syndromes" *Curr Opin Neurol* 15(5): 545-52), ataxia (See, Meisler, M. H., J. A. Kearney, et al. (2002) "Mutations of voltage-gated sodium channels in movement disorders and epilepsy" *Novartis Found Symp* 241: 72-81), multiple sclerosis (See. Black, J. A., S. Dib-Hajj, et al. (2000) "Sensory neuron-specific sodium channel SNS is abnormally expressed in the brains of mice with experimental allergic encephalomyelitis and humans with multiple sclerosis" *Proc Natl Acad Sci USA* 97(21): 11598-602, and Renganathan, M., M. Gelderblom, et al. (2003) "Expression of Na(v)1.8 sodium channels perturbs the firing patterns of cerebellar purkinje cells" *Brain Res* 959(2): 23542), irritable bowel (See, Su, X., R. E. Wachtel, et al. (1999) "Capsaicin sensitivity and voltage-gated sodium currents in colon sensory neurons from rat dorsal root ganglia" *Am J Physiol* 277(6 Pt 1): G1180-8, and Laird, J. M., V. Souslova, et al. (2002) "Deficits in visceral pain and referred hyperalgesia in Nav1.8 (SNS/PN3)-null mice" *J Neurosci* 22(19): 8352-6), urinary incontinence and visceral pain (See, Yoshimura, N., S. Seki, et al. (2001) "The involvement of the tetrodotoxin-resistant sodium channel Na(v)1.8 (PN3/SNS) in a rat model of visceral pain" *J Neurosci* 21(21): 8690-6), as well as an array of psychiatry dysfunctions such as anxiety and depression (See, Hurley, S. C. (2002) "Lamotrigine update and its use in mood disorders" *Ann Pharmacother* 36(5): 860-73).

Voltage gated Na channels comprise a gene family consisting of 9 different subtypes (NaV1.1-NaV1.9). These subtypes show tissue specific localization and functional differences (See, Goldin, A. L. (2001) "Resurgence of sodium channel research" *Annu Rev Physiol* 63: 871-94). Three members of the gene family (NaV1.8, 1.9, 1.5) are resistant to block by the well-known Na channel blocker TTX, demonstrating subtype specificity within this gene family. Mutational analysis has identified glutamate 387 as a critical residue for TTX binding (See. Noda, M., H. Suzuki, et al. (1989) "A single point mutation confers tetrodotoxin and saxitoxin insensitivity on the sodium channel II" *FEBS Lett* 259(1): 213-6).

In general, voltage-gated sodium channels (NaVs) are responsible for initiating the rapid upstroke of action potentials in excitable tissue in nervous system, which transmit the electrical signals that compose and encode normal and aberrant pain sensations. Antagonists of NaV channels can attenuate these pain signals and are useful for treating a variety of pain conditions, including but not limited to acute, chronic, inflammatory, and neuropathic pain. Known NaV antagonists, such as TTX, lidocaine (See, Mao, J. and L. L. Chen (2000) "Systemic lidocaine for neuropathic pain relief" *Pain* 87(1): 7-17.) bupivacaine, phenyloin (See, Jensen, T. S. (2002) "Anticonvulsants in neuropathic pain: rationale and clinical evidence" *Eur J Pain* 6 (Suppl A): 61-8), lamotrigine (See, Rozen, T. D. (2001) "Antiepileptic drugs in the management of cluster headache and trigeminal neuralgia" *Headache* 41 Suppl 1: S25-32 and Jensen, T. S. (2002) "Anticonvulsants in neuropathic pain: rationale and clinical evidence" *Eur J Pain* 6 (Suppl A): 61-8.), and carbamazepine (See, Backonja, M. M. (2002) "Use of anticonvulsants for treatment of neuropathic pain" *Neurology* 59(5 Suppl 2): S14-7), have been shown to be useful attenuating pain in humans and animal models.

Hyperalgesia (extreme sensitivity to something painful) that develops in the presence of tissue injury or inflammation reflects, at least in part, an increase in the excitability of high-threshold primary afferent neurons innervating the site of injury. Voltage sensitive sodium channels activation is critical for the generation and propagation of neuronal action potentials. There is a growing body of evidence indicating that modulation of NaV currents is an endogenous mechanism used to control neuronal excitability (See, Goldin, A. L. (2001) "Resurgence of sodium channel research" *Annu Rev Physiol* 63: 871-94). Several kinetically and pharmacologically distinct voltage-gated sodium channels are found in dorsal root ganglion (DRG) neurons. The TTX-resistant current is insensitive to micromolar concentrations of tetrodotoxin, and displays slow activation and inactivation kinetics and a more depolarized activation threshold when compared to other voltage-gated sodium channels. TTX-resistant sodium currents are primarily restricted to a subpopulation of sensory neurons likely to be involved in nociception. Specifically, TTX-resistant sodium currents are expressed almost exclusively in neurons that have a small cell-body diameter; and give rise to small-diameter slow-conducting axons and that are responsive to capsaicin. A large body of experimental evidence demonstrates that TTX-resistant sodium channels are expressed on C-fibers and are important in the transmission of nociceptive information to the spinal cord.

Intrathecal administration of antisense oligo-deoxynucleotides targeting a unique region of the TTX-resistant sodium channel (NaV1.8) resulted in a significant reduction in PGE$_2$-induced hyperalgesia (See, Khasar, S. G., M. S. Gold, et al. (1998) "A tetrodotoxin-resistant sodium current mediates inflammatory pain in the rat" *Neurosci Lett* 256(1): 17-20). More recently, a knockout mouse line was generated by Wood and colleagues, which lacks functional NaV1.8. The mutation has an analgesic effect in tests assessing the animal's response to the inflammatory agent carrageenan (ee, Akopian, A. N., V. Souslova, et al. (1999) "The tetrodotoxin-resistant sodium channel SNS has a specialized function in pain pathways" *Nat Neurosci* 2(6): 541-8). In addition, deficit in both mechano- and thermoreception were observed in these animals. The analgesia shown by the Nav1.8 knockout mutants is consistent with observations about the role of TTX-resistant currents in nociception.

Immunohistochemical, in-situ hybridization and in-vitro electrophysiology experiments have all shown that the sodium channel NaV1.8 is selectively localized to the small sensory neurons of the dorsal root ganglion and trigeminal ganglion (See, Akopian, A. N., L. Sivilotti, et al. (1996) "A tetrodotoxin-resistant voltage-gated sodium channel expressed by sensory neurons" *Nature* 379(6562): 257-62). The primary role of these neurons is the detection and transmission of nociceptive stimuli. Antisense and immunohistochemical evidence also supports a role for NaV1.8 in neuropathic pain (See, Lai, J., M. S. Gold, et al. (2002) "Inhibition of neuropathic pain by decreased expression of the tetrodotoxin-resistant sodium channel, NaV1.8" *Pain* 95(1-2): 143-52, and Lai, J., J. C. Hunter, et al. (2000) "Blockade of neuropathic pain by antisense targeting of tetrodotoxin-resistant sodium channels in sensory neurons" *Methods Enzymol* 314: 201-13). NaV1.8 protein is upregulated along uninjured C-fibers adjacent to the nerve injury. Antisense treatment prevents the redistribution of NaV1.8 along the nerve and reverses neuropathic pain. Taken together the gene-knockout and antisense data support a role for NaV1.8 in the detection and transmission of inflammatory and neuropathic pain.

Several Na channel blockers are currently used or being tested in the clinic to treat epilepsy (See, Moulard, B. and D. Bertrand (2002) "Epilepsy and sodium channel blockers" *Expert Opin. Ther. Patents* 12(1): 85-91.); acute (See, Wiffen, P., S. Collins, et al. (2000) "Anticonvulsant drugs for acute and chronic pain" *Cochrane Database Syst Rev* 3), chronic (See, Wiffen, P., S. Collins, et al. (2000) "Anticonvulsant drugs for acute and chronic pain" *Cochrane Database Syst Rev* 3, and Guay, D. R. (2001) "Adjunctive agents in the management of chronic pain" *Pharmacotherapy* 21(9): 1070-81), inflammatory (See, Gold, M. S. (1999) "Tetrodotoxin-resistant Na+ currents and inflammatory hyperalgesia." *Proc Natl Acad Sci USA* 96(14): 7645-9), and neuropathic pain (See Strichartz, G. R., Z. Zhou, et al. (2002) "Therapeutic concentrations of local anaesthetics unveil the potential role of sodium channels in neuropathic pain" *Novartis Found Symp* 241: 189-201, and Sandner-Kiesling, A., G. Rumpold Seitlinger, et al. (2002) "Lamotrigine monotherapy for control of neuralgia after nerve section" *Acta Anaesthesiol Scand* 46(10): 1261-4); cardiac arrhythmias (See An, R. H., R. Bangalore, et al. (1996) "Lidocaine block of LQT-3 mutant human Na+ channels" *Circ Res* 79(1): 103-8, and Wang, D. W., K. Yazawa, et al. (1997) "Pharmacological targeting of long QT mutant sodium channels" *J Clin Invest* 99(7): 1714-20); neuroprotection (See, Taylor, C. P. and L. S, Narasimhan (1997) "Sodium channels and therapy of central nervous system diseases" *Adv Pharmacol* 39: 47-98) and as anesthetics (See, Strichartz, G. R., Z. Zhou, et al. (2002) "Therapeutic concentrations of local anaesthetics unveil the potential role of sodium channels in neuropathic pain." *Novartis Found Symp* 241: 189-201).

Various animal models with clinical significance have been developed for the study of sodium channel modulators for numerous different pain indications. E.g., malignant chronic pain, see Kohase, H., et al., Acta Anaesthesiol Scand. 2004; 48(3):382-3; femur cancer pain (see, Kohase, H., et al., Acta Anaesthesiol Scand. 2004; 48(3):382-3); non-malignant chronic bone pain (see, Ciocon, J. O. et al., J Am Geriatr Soc. 1994; 42(6):593-6); rheumatoid arthritis (see, Calvino, B. et al., Behav Brain Res. 1987; 24(1):11-29); osteoarthritis (see, Guzman, R. E., et al., Toxicol Pathol. 2003; 31(6):619-24); spinal stenosis (see, Takenobu, Y. et al., J Neurosci Methods. 2001; 104(2):191-8); Neuropathic low back pain (see, Hines, R., et al., Pain Med. 2002; 3(4):361-5; Massie, J. B., et al., J Neurosci Methods. 2004; 137(2):283-9; neuropathic low back pain (see, Hines, R., et al., Pain Med. 2002; 3(4):361-5; Massie, J. B., et al., J Neurosci Methods. 2004; 137(2):283-9); myofascial pain syndrome (see, Dalpiaz & Dodds, J Pain Palliat Care Pharmacother. 2002; 16(1):99-104; Sluka K. A. et al., Muscle Nerve. 2001; 24(1):37-46); fibromyalgia (see, Bennet & Tai, Int J Clin Pharmacol Res. 1995; 15(3):115-9); temporomandibular joint pain (see, Ime H., Ren K., Brain Res Mol Brain Res. 1999; 67(1):87-97); chronic visceral pain, including, abdominal (see, Al-Chaer, E. D., et al., Gastroenterology. 2000; 119(5):1276-85); pelvic/perineal pain, (see, Wesselmann et al., Neurosci Lett. 1998; 246(2):73-6); pancreatic (see, Vera-Portocarrero, L. B., et al., Anesthesiology. 2003; 98(2):474-84);

IBS pain (see, Verne, G. N., et al., Pain. 2003; 105(1-2):223-30; La J. H. et al., World Gastroenterol. 2003; 9(12):2791-5); chronic headache pain (see, Willimas & Stark, Cephalalgia. 2003; 23(10):963-71); migraine (see, Yamamura, H., et al., J Neurophysiol. 1999; 81(2):479-93); tension headache, including, cluster headaches (see, Costa, A., et al., Cephalalgia. 2000; 20(2):85-91); chronic neuropathic pain, including, post-herpetic neuralgia (see, Attal, N., et al., Neurology. 2004; 62(2):218-25; Kim & Chung 1992, Pain 50:355); diabetic neuropathy (see, Beidoun A. et al., Clin J Pain. 2004; 20(3):174-8; Courteix, C., et al., Pain. 1993; 53(1):81-8); HIV-associated neuropathy (see, Portegies & Rosenberg, Ned Tijdschr Geneeskd. 2001; 145(15):731-5; Joseph E. K. et al., Pain. 2004; 107(1-2):147-58; Oh, S. B., et al., J. Neurosci. 2001; 21(14):5027-35); trigeminal neuralgia (see, Sato, J., et al., Oral Surg Oral Med Oral Pathol Oral Radiol Endod. 2004; 97(1):18-22; Imamura Y. et al., Exp Brain Res. 1997; 116(1):97-103); Charcot-Marie Tooth neuropathy (see, Sereda, M., et al., Neuron. 1996; 16(5):1049-60); hereditary sensory neuropathies (see, Lee, M. J., et al., Hum Mol. Genet. 2003; 12(15):1917-25); peripheral nerve injury (see, Attal, N., et al., Neurology. 2004; 62(2):218-25; Kim & Chung 1992, Pain 50:355; Bennett & Xie, 1988, Pain 33:87; Decostered, I. & Woolf, C. J., 2000, Pain 87:149; Shir, Y. & Seltzer, Z. 1990; Neurosci Lett 115:62); painful neuromas (see, Nahabedian & Johnson, Ann Plast Surg. 2001; 46(1):15-22; Devor & Raber, Behav Neural Biol. 1983; 37(2):276-83); ectopic proximal and distal discharges (see, Liu, X. et al., Brain Res. 2001; 900(1): 119-27); radiculopathy (see, Devers & Galer, (see, Clin J Pain. 2000; 16(3):205-8; Hayashi N. et al., Spine. 1998; 23(8):877-85); chemotherapy induced neuropathic pain (see, Aley, K. O., et al., Neuroscience. 1996; 73(1):259-65); radiotherapy-induced neuropathic pain; post-mastectomy pain (see, Devers & Galer, Clin J Pain. 2000; 16(3):205-8); central pain (Cahana, A., et al., Anesth Analg. 2004; 98(6):1581-4), spinal cord injury pain (see, Hains, B. C., et al., Exp Neurol. 2000; 164(2):426-37); post-stroke pain; thalamic pain (see, LaBuda, C. J., et al., Neurosci Lett. 2000; 290(1):79-83); complex regional pain syndrome (see, Wallace, M. S., et al., Anesthesiology. 2000; 92(1):75-83; Xantos, D. et al., J Pain. 2004; 5(3 Suppl 2):S1); phantom pain (see, Weber, W. E., Ned Tijdschr Geneeskd. 2001; 145(17):813-7; Levitt & Heyback, Pain. 1981; 10(1):67-73); intractable pain (see, Yokoyama, M., et al., Can J Anaesth. 2002; 49(8):810-3); acute pain, acute post-operative pain (see, Koppert, W., et al., Anesth Analg. 2004; 98(4):1050-5; Brennan, T. J., et al., Pain. 1996; 64(3):493-501); acute musculoskeletal pain; joint pain (see, Gotoh, S., et al., Ann Rheum Dis. 1993; 52(11):817-22);

mechanical low back pain (see, Kehl, L. J., et al., Pain. 2000; 85(3):333-43); neck pain; tendonitis; injury/exercise pain (see, Sesay, M., et al., Can J Anaesth. 2002; 49(2):137-43); acute visceral pain, including, abdominal pain; pyelonephritis; appendicitis; cholecystitis; intestinal obstruction; hernias; etc (see, Giambernardino, M. A., et al., Pain. 1995; 61(3):459-69); chest pain, including, cardiac pain (see, Vergona, R. A., et al., Life Sci. 1984; 35(18):1877-84); pelvic pain, renal colic pain, acute obstetric pain, including, labor pain (see, Segal, S., et al., Anesth Analg. 1998; 87(4):864-9); cesarean section pain; acute inflammatory, burn and trauma pain; acute intermittent pain, including, endometriosis (see, Cason, A. M., et al., Horn Behav. 2003; 44(2):123-31); acute herpes zoster pain; sickle cell anemia; acute pancreatitis (see, Toma, H; Gastroenterology. 2000; 119(5):1373-81); breakthrough pain; orofacial pain, including, sinusitis pain, dental pain (see, Nusstein, J., et al., J Endod. 1998; 24(7):487-91; Chidiac, J. J., et al., Eur J Pain. 2002; 6(1):55-67); multiple sclerosis (MS) pain (see, Sakurai & Kanazawa, J Neurol Sci. 1999; 162(2):162-8); pain in depression (see, Greene, B., Curr Med Res Opin. 2003; 19(4):272-7); leprosy pain; Behcet's disease pain; adiposis dolorosa (see, Devillers & Oranje, Clin Exp Dermatol. 1999; 24(3):240-1); phlebitic pain; Guillain-Barre pain; painful legs and moving toes; Haglund syndrome; erythromelalgia pain (see, Legroux-Crespel, E., et al., Ann Dermatol Venereol. 2003; 130(4):429-33); Fabry's disease pain (see, Germain, D. P., J Soc Biol. 2002; 196(2):183-90); Bladder and urogenital disease, including, urinary incontinence (see, Berggren, T., et al., J Urol. 1993; 150(5 Pt 1):1540-3); hyperactivity bladder (see, Chuang, Y. C., et al., Urology. 2003; 61(3):664-70); painful bladder syndrome (see, Yoshimura, N., et al., J. Neurosci. 2001; 21(21):8690-6); interstitial cystitis (IC) (see, Giannakopoulos& Campilomatos, Arch Ital Urol Nefrol Androl. 1992; 64(4):337-9; Boucher, M., et al., J Urol. 2000; 164(1):203-8); and prostatitis (see, Mayersak, J. S., Int Surg. 1998; 83(4):347-9; Keith, I. M., et al., J Urol. 2001; 166(1):323-8).

Unfortunately, as described above, the efficacy of currently used sodium channel blockers and calcium channel blockers for the disease states described above has been to a large extent limited by a number of side effects. These side effects include various CNS disturbances such as blurred vision, dizziness, nausea, and sedation as well more potentially life threatening cardiac arrhythmias and cardiac failure. Such undesirable side effects may be avoided by using a Na channel blocker that exhibit a degree of selectivity in its activity against a Na channel subtype. However, Na channel blockers currently in the market lack such selectivity. Perhaps because of this lack of molecular selectivity, drugs currently in the market exhibit use-dependent block and generally show higher affinity at depolarized potentials resulting in the preferential targeting of actively firing neurons, believed to be a key factor in the therapeutic window of existing Na channel blocking drugs. While every drug has it own unique therapeutic profile, current Na channel blockers are generally associated with central nervous system (CNS) and cardiovascular (CV) side-effects, including blood pressure changes, which are often dose-limiting. Dizziness, sedation, nausea, ataxia, and confusion are some of the specific side-effects observed for Phenyloin™, Mexiletine™, and Lidocaine™.

There is also a need to develop Na channel blockers that have minimal or no inhibitory activity against the hERG channel. hERG (human ether a-go-go related gene) encodes a potassium ion channel (hERG channel) that is involved in cardiac repolarization. See, e.g., Pearlstein, R., R. Vaz, et al. (2003). "Understanding the Structure-Activity Relationship of the Human Ether-a-go-go-Related Gene Cardiac K(+) Channel. A Model for Bad Behavior." *J Med Chem* 46(11): 2017-22. Interaction with the hERG channel is one indicator of potential cardiac toxicity. hERG-block increases the likelihood of cardiac QT-interval prolongation and dispersion. A subset of compounds that prolong the QT interval can cause ventricular fibrillation and cardiac failure. Belardinelli, L., C. Antzelevitch and M. A. Vos (2003). "Assessing predictors of drug-induced torsade de pointes". Trends Pharmacol Sci. 24 (12): 619-25; Al-Khatib, S. M., N. M. LaPointe, et al. (2003). "What clinicians should know about the QT interval." *Jama* 289(16): 2120-7; http://www.fenichel.net/pages/site_map.htm.

There is also a need to develop Na channel blockers that have minimal or no inhibitory activity against the Cytochrome P450 enzyme family. Within this family, CYP 3A4 isoform is believed to be the major isoform present in the liver and small intestines. Other key isoforms include CYP 2D6, CYP 2C9, and CYP 1A2. See, e.g., U.S. Pat. No. 6,514,687, the disclosure whereof is incorporated herein by reference. A Na channel blocker that inhibits one or more of the isoforms can cause undesirable side effect or can cause undesirable drug-drug interactions when administered with another drug that interacts with that isoform. See, e.g, Davit, B., et al. (1999), "FDA Evaluations Using In Vitro Metabolism to Predict and Interpret In Vivo Metabolic Drug-Drug Interactions: Impact on Labeling," J. Clin. Pharmacol., 39: 899-910; "Drug Metabolism/Drug Interaction Studies in the Drug Development Process: Studies In Vitro, Dept. of Health and Human Services, U.S.F.D.A (http://www.fda.gov/cder/guidance.htm).

There is also a need to develop Na channel blockers that exhibit selectivity against a certain sub-type of Na channel. Particularly useful are compounds that have a desirably low activity against NaV 1.2.

There is also a need to develop Na channel blockers that have a desirably low activity against L-type calcium channel 1.2. CaV1.2 calcium channels are abundantly expressed in smooth and striated muscle, especially in the heart, brain and endocrine cells. Blocking these channels can be therapeutically useful, but it can also result in significant side effects. The most significant concerns are impairment of cardiac contractility (that is, a negative inotropic effect) and slowing of electrical conduction in the pacemaker regions of the heart. See, e.g., Kizer, J. R., et al., "Epidemiologic Review of the Calcium Channel Blocker Drugs," Arch. Intern Med. 2001; 161: 1145-1158.

There is also a need to Na channel blockers that have a desirably low activity against potassium channel 1.5 ("Kv1.5"; also known as KCNA5). Kv1.5 is found primarily in human atrial cells, but also in brain. See, e.g., Gutman, G. A., et al., "Compendium of Voltage-Gated Ion Channels Potassium Channels," Pharmacol. Rev., 55: 583-585 (2003). Unwanted block of Kv1.5 could produce convulsion or ataxia.

There is also a need to develop Na channel blockers that have improved pharmacokinetic and/or pharmacodynamic properties and, therefore, are better suited for in-vivo administration for therapeutic purposes. Such properties include aqueous solubility, bioavailability, clearance kinetics, etc. See, e.g., Shargel, L., Yu, A., Ed's "Applied Biopharmaceutics & Pharmacokinetics", 4th Ed., McGraw-Hill, New York, 1999; Yacobi, A., Skelly, J. P., Shah, V. P., Benet, L. Z., Ed's. "Integration of Pharmacokinetics, Pharmacodynamics, and Toxicokinetics in Rational Drug Development", Plenum Press, New York, 1993; Lee, J. S., Obach, R. S., Fisher, M. B., Ed's. "Drug Metabolizing Enzymes Cytochrome P450 and Other Enzymes in Drug Discovery and Development", Marcel Dekker, New York, 2003; Birkett, D. J. "Pharmacokinetics Made Easy", McGraw-Hill Australia, Roseville, Australia, 2002; Katzung, B. G. "Basic & Clinical Pharmacology", McGraw-Hill, New York, 2001; Welling, P. G., Tse, F. L. S., Ed's. "Pharmacokinetics", Marcel Dekker, New York, 1988; Thomas, G. "Medicinal Chemistry An Introduction", Wiley & Sons, New York, 2000; and Gennaro, A. R., et al., "Remington: The Science and Practice of Pharmacy," 20th Ed., Lippincott, Williams, & Wilkins (2003).

A Na channel blocker that meets one or more of the above unmet needs would be a very desirable improvement over the currently marketed Na channel blockers and would greatly benefit patients in need of a therapy therewith.

SUMMARY OF THE INVENTION

The present invention provides a compound of formula IA or formula IB:

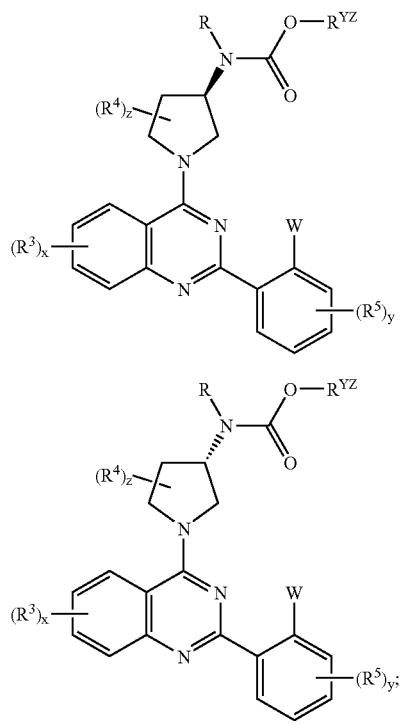

or a pharmaceutically acceptable salt or derivative thereof.

These compounds and pharmaceutically acceptable compositions are useful for treating or lessening the severity of a variety of diseases, disorders, or conditions, including, but not limited to, acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

BRIEF DESCRIPTION OF DRAWINGS

FIG. 1 shows an hERG assay manual patch electronic stimulation protocol

DETAILED DESCRIPTION OF THE INVENTION

1. General Description of Compounds of the Invention:
The present invention provides a compound of formula IA or formula IB:

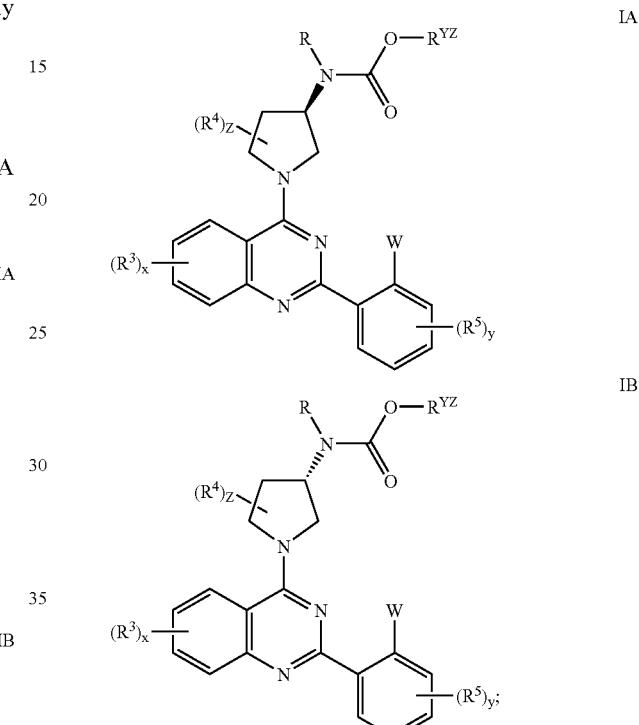

or a pharmaceutically acceptable salt or derivative thereof, wherein:
z is 0-3;
$R^{YZ}$ is $C_1$-$C_6$ aliphatic group, optionally substituted with $w_4$ independent occurrences of —$R^{14}$, wherein $w_4$ is 0-3;
wherein up to two methylene units in $R^{YZ}$ are optionally replaced with —NR—, —O—, —COO, —OCO—, —NRCO—, —CONR—, —SO$_2$NR—, or —NRSO$_2$—;
x and y, each, is independently 0-4;
W is halo, —O$R^{XY}$, —CHF$_2$, or —CF$_3$;
$R^{XY}$ is hydrogen or a group selected from:

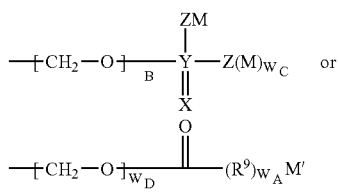

wherein:
each of $w_A$, $w_B$, $w_C$, and $w_D$ is independently 0 or 1;
each M is independently selected from hydrogen, Li, Na, K, Mg, Ca, Ba, —N($R^7$)$_4$, —$C_1$-$C_{12}$-alkyl, —$C_2$-$C_{12}$-alkenyl, or —R$^6$; wherein 1 to 4-CH$_2$ radicals of the alkyl or alkenyl group, other than the —CH$_2$ that is bound to Z, is optionally replaced by a heteroatom group selected from O, S, S(O), S(O$_2$), or N(R$^7$); and wherein any hydrogen in said alkyl, alkenyl or R$^6$ is optionally replaced with a substituent selected from oxo, —OR$^7$, —R$^7$, —N(R$^7$)$_2$, —N(R$^7$), —R$^7$OH, —CN, —CO$_2$R$^7$, —C(O)—N(R$^7$)$_2$, —S(O)$_2$—N(R$^7$)$_2$, —N(R$^7$)—C(O)—R$^7$, —C(O)R$^7$, —S(O)$_n$—R$^7$, —OCF$_3$, —S(O)$_n$—R$^6$, —N(R$^7$)—S(O)$_2$(R$^7$), halo, —CF$_3$, or —NO$_2$;

n is 0-2;

M' is H, —C$_1$-C$_{12}$-alkyl, —C$_2$-C$_{12}$-alkenyl, or —R$^6$; wherein 1 to 4-CH$_2$ radicals of the alkyl or alkenyl group is optionally replaced by a heteroatom group selected from O, S, S(O), S(O$_2$), or N(R$^7$); and wherein any hydrogen in said alkyl, alkenyl or R$^6$ is optionally replaced with a substituent selected from oxo, —OR$^7$, —R$^7$, —N(R$^7$)$_2$, —N(R$^7$)$_3$, —R$^7$OH, —CN, —CO$_2$R$^7$, —C(O)—N(R$^7$)$_2$, —S(O)$_2$—N(R$^7$)$_2$, —N(R$^7$)—C(O)—R$^7$, —C(O)R$^7$, —S(O)$_n$—R$^7$, —OCF$_3$, —S(O)$_n$—R$^6$, —N(R$^7$)—S(O)$_2$(R$^7$), halo, —CF$_3$, or —NO$_2$;

Z is —CH$_2$—, —O—, —S—, —N(R$^7$)$_2$—; or, when M is absent, then Z is hydrogen, =O, or =S;

Y is P or S, wherein when Y is S, then Z is not S;

X is O or S;

each R$^7$ is independently selected from hydrogen, or C$_1$-C$_4$ aliphatic, optionally substituted with up to two Q$_1$;

each Q$_1$ is independently selected from a 3-7 membered saturated, partially saturated or unsaturated carbocyclic ring system; or a 5-7 membered saturated, partially saturated or unsaturated heterocyclic ring containing one or more heteroatom or heteroatom group selected from O, N, NH, S, SO, or SO$_2$; wherein Q$_1$, is optionally substituted with up to three substituents selected from oxo, —OH, —O(C$_1$-C$_4$ aliphatic), —C$_1$-C$_4$ aliphatic, —NH$_2$, —NH(C$_1$-C$_4$ aliphatic), —N(C$_1$-C$_4$ aliphatic)$_2$, —N(C$_1$-C$_4$ aliphatic)-C(O)—C$_1$-C$_4$ aliphatic, —(C$_1$-C$_4$ aliphatic)-OH, —CN, —CO$_2$H, —CO$_2$(C$_1$-C$_4$ aliphatic), —C(O)—NH$_2$, —C(O)—NH(C$_1$-C$_4$ aliphatic), —C(O)—N(C$_1$-C$_4$ aliphatic)$_2$, halo, or —CF$_3$;

R$^6$ is a 5-6 membered saturated, partially saturated or unsaturated carbocyclic or heterocyclic ring system, or an 8-10 membered saturated, partially saturated or unsaturated bicyclic ring system; wherein any of said heterocyclic ring systems contains one or more heteroatoms selected from O, N, S, S(O)$_n$ or N(R$^7$); and wherein any of said ring systems optionally contains 1 to 4 substituents independently selected from OH, —C$_1$-C$_4$ alkyl, —O—C$_1$-C$_4$ alkyl or —O—C(O)—C$_1$-C$_4$ alkyl;

R$^9$ is C(R$^7$)$_2$, O or N(R$^7$);

each occurrence of R$^{14}$, R$^3$, R$^4$, and R$^5$ is independently Q-Rx; wherein Q is a bond or is a C$_1$-C$_6$ alkylidene chain wherein up to two non-adjacent methylene units of Q are optionally and independently replaced by —NR—, —S—, —O—, —CS—, —CO$_2$—, —OCO—, —CO—, —COCO—, —CONR—, —NRCO—, —NRCO$_2$—, —SO$_2$NR—, —NRSO$_2$—, —CONRNR—, —NRCONR—, —OCONR—, —NRNR—, —NRSO$_2$NR—, —SO—, —SO$_2$—, —PO—, —PO$_2$—, —OP(O)(OR)—, or —POR—; and each occurrence of R$^x$ is independently selected from —R', halogen, =NR', —NO$_2$, —CN, —OR', —SR', —N(R')$_2$, —NR'COR', —NR'CON(R')$_2$, —NR'CO$_2$R', —COR', —CO$_2$R', —OCOR', —CON(R')$_2$, —OCON(R')$_2$, —SOR', —SO$_2$R', —SO$_2$N(R')$_2$, —NR'SO$_2$R', —NR'SO$_2$N(R')$_2$, —COCOR', —COCH$_2$COR', —OP(O)(OR')$_2$, —P(O)(OR')$_2$, —OP(O)$_2$OR', —P(O)$_2$OR', —PO(R')$_2$, or —OPO(R')$_2$; and each occurrence of R is independently hydrogen or C$_1$-C$_6$ aliphatic group having up to three substituents; and each occurrence of R' is independently hydrogen or C$_1$-C$_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein R' has up to four substituents; or R' and R', two occurrences of R', or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

provided that the following compounds are excluded:

carbamic acid, [(3R)-1-[2-(2-hydroxyphenyl)-7-methyl-4-quinazolinyl]-3-pyrrolidinyl]-,phenylmethyl ester;

carbamic acid, [(3R)-1-[2-(2-hydroxyphenyl)-7-methyl-4-quinazolinyl]-3-pyrrolidinyl]-,phenylmethyl ester, monohydrochloride;

carbamic acid, [(3S)-1-[2-(2-hydroxyphenyl)-7-methyl-4-quinazolinyl]-3-pyrrolidinyl]-,1,1-dimethylethyl ester;

carbamic acid, [(3R)-1-[2-(2-hydroxyphenyl)-7-methyl-4-quinazolinyl]-3-pyrrolidinyl]-,1,1-dimethylethyl ester;

carbamic acid, [(3R)-1-[6-fluoro-2-(2-hydroxyphenyl)-4-quinazolinyl]-3-pyrrolidinyl]-,1,1-dimethylethyl ester;

carbamic acid, [(3R)-1-[2-(2-fluoro-6-hydroxyphenyl)-7-methyl-4-quinazolinyl]-3-pyrrolidinyl]-,1,1-dimethylethyl ester;

carbamic acid, [(3R)-1-[2-(2-hydroxyphenyl)-7-methyl-4-quinazolinyl]-3-pyrrolidinyl]-,3-pyridinylmethyl ester, trifluoroacetate (salt);

carbamic acid, [(3R)-1-[2-(2-hydroxyphenyl)-7-methyl-4-quinazolinyl]-3-pyrrolidinyl]-,4-pyridinylmethyl ester, trifluoroacetate (salt);

carbamic acid, [(3R)-1-[2-(2-hydroxyphenyl)-7-methyl-4-quinazolinyl]-3-pyrrolidinyl]-,1,3-benzodioxol-4-ylmethyl ester, trifluoroacetate (salt);

carbamic acid, [(3R)-1-[6-fluoro-2-(2-hydroxyphenyl)-4-quinazolinyl]-3-pyrrolidinyl]-,(tetrahydro-2H-pyran-2-yl)methyl ester, trifluoroacetate (salt); and carbamic acid, [(3R)-1-[2-(2-hydroxyphenyl)-7-methyl-4-quinazolinyl]-3-pyrrolidinyl]-,(tetrahydro-2H-pyran-2-yl)methyl ester.

2. Compounds and Definitions:

Compounds of this invention include those described generally above, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle" "cycloaliphatic" or "cycloalkyl"), that has a single point of attachment to the rest of the molecule. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. In some embodiments, "cycloaliphatic" (or "carbocycle" or "cycloalkyl") refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

The term "heteroaliphatic", as used herein, means aliphatic groups wherein one or two carbon atoms are independently replaced by one or more of oxygen, sulfur, nitrogen, phosphorus, or silicon. Heteroaliphatic groups may be substituted or unsubstituted, branched or unbranched, cyclic or acyclic, and include "heterocycle", "heterocyclyl", "heterocycloaliphatic", or "heterocyclic" groups.

The term "heterocycle", "heterocyclyl", "heterocycloaliphatic", or "heterocyclic" as used herein means non-aromatic, monocyclic, bicyclic, or tricyclic ring systems in which one or more ring members are an independently selected heteroatom. In some embodiments, the "heterocycle", "heterocyclyl", "heterocycloaliphatic", or "heterocyclic" group has three to fourteen ring members in which one or more ring members is a heteroatom independently selected from oxygen, sulfur, nitrogen, or phosphorus, and each ring in the system contains 3 to 7 ring members.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the principal carbon chain through an oxygen ("alkoxy") or sulfur ("thioalkyl") atom.

The terms "haloalkyl", "haloalkenyl" and "haloalkoxy" means alkyl, alkenyl or alkoxy, as the case may be, substituted with one or more halogen atoms. The term "halogen" means F, Cl, Br, or I.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", used alone or as part of a larger moiety as in "heteroaralkyl" or "heteroarylalkoxy", refers to monocyclic, bicyclic, and tricyclic ring systems having a total of five to fourteen ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic".

An aryl (including aralkyl, aralkoxy, aryloxyalkyl and the like) or heteroaryl (including heteroaralkyl and heteroarylalkoxy and the like) group may contain one or more substituents and thus may be "optionally substituted". Unless otherwise defined above and herein, suitable substituents on the unsaturated carbon atom of an aryl or heteroaryl group are generally selected from halogen; —$R^\circ$; —$OR^\circ$; —$SR^\circ$; phenyl (Ph) optionally substituted with $R^\circ$; —O(Ph) optionally substituted with $R^\circ$; —$(CH_2)_{1-2}$(Ph), optionally substituted with $R^\circ$; —CH=CH(Ph), optionally substituted with $R^\circ$; —$NO_2$; —CN; —$N(R^\circ)_2$; —$NR^\circ C(O)R^\circ$; —$NR^\circ C(S)R^\circ$; —$NR^\circ C(O)N(R^\circ)_2$; —$NR^\circ C(S)N(R^\circ)_2$; —$NR^\circ CO_2 R^\circ$; —$NR^\circ NR^\circ C(O)R^\circ$; —$NR^\circ NR^\circ C(O)N(R^\circ)_2$; —$NR^\circ NR^\circ CO_2 R^\circ$; —$C(O)C(O)R^\circ$; —$C(O)CH_2 C(O)R^\circ$; —$CO_2 R^\circ$; —$C(O)R^\circ$; —$C(S)R^\circ$; —$C(O)N(R^\circ)_2$; —$C(S)N(R^\circ)_2$; —$OC(O)N(R^\circ)_2$; —$OC(O)R^\circ$; —$C(O)N(OR^\circ)R^\circ$; —$C(NOR^\circ)R^\circ$; —$S(O)_2 R^\circ$; —$S(O)_3 R^\circ$; —$SO_2 N(R^\circ)_2$; —$S(O)R^\circ$; —$NR^\circ SO_2 N(R^\circ)_2$; —$NR^\circ SO_2 R^\circ$; —$N(OR^\circ)R^\circ$; —C(=NH)—$N(R^\circ)_2$; —$P(O)_2 R^\circ$; —$PO(R^\circ)_2$; —$OPO(R^\circ)_2$; —$(CH_2)_{0-2} NHC(O)R^\circ$; phenyl (Ph) optionally substituted with $R^\circ$; —O(Ph) optionally substituted with $R^\circ$; —$(CH_2)_{1-2}$(Ph), optionally substituted with $R^\circ$; or —CH=CH(Ph), optionally substituted with $R^\circ$; wherein each independent occurrence of $R^\circ$ is selected from hydrogen, optionally substituted $C_{1-6}$ aliphatic, an unsubstituted 5-6 membered heteroaryl or heterocyclic ring, phenyl, —O(Ph), or —$CH_2$(Ph), or, notwithstanding the definition above, two independent occurrences of $R^\circ$, on the same substituent or different substituents, taken together with the atom(s) to which each $R^\circ$ group is bound, to form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group of R° are selected from NH₂, NH(C₁₋₄aliphatic), N(C₁₋₄aliphatic)₂, halogen, C₁₋₄aliphatic, OH, O(C₁₋₄aliphatic), NO₂, CN, CO₂H, CO₂(C₁₋₄aliphatic), O(halo C₁₋₄ aliphatic), or halo C₁₋₄aliphatic, wherein each of the foregoing C₁₋₄aliphatic groups of R° is unsubstituted.

An aliphatic or heteroaliphatic group, or a non-aromatic heterocyclic ring may contain one or more substituents and thus may be "optionally substituted". Unless otherwise defined above and herein, suitable substituents on the saturated carbon of an aliphatic or heteroaliphatic group, or of a non-aromatic heterocyclic ring are selected from those listed above for the unsaturated carbon of an aryl or heteroaryl group and additionally include the following: =O, =S, =NNHR*, =NN(R*)₂, =NNHC(O)R*, =NNHCO₂ (alkyl), =NNHSO₂(alkyl), or =NR*, where each R* is independently selected from hydrogen or an optionally substituted C₁₋₆ aliphatic group.

Unless otherwise defined above and herein, optional substituents on the nitrogen of a non-aromatic heterocyclic ring are generally selected from —R⁺, —N(R⁺)₂, —C(O)R⁺, —CO₂R⁺, —C(O)C(O)R⁺, —C(O)CH₂C(O)R⁺, —SO₂R⁺, —SO₂N(R⁺)₂, —C(=S)N(R⁺)₂, —C(=NH)—N(R⁺)₂, or —NR⁺SO₂R⁺; wherein R⁺ is hydrogen, an optionally substituted C₁₋₆ aliphatic, optionally substituted phenyl, optionally substituted —O(Ph), optionally substituted —CH₂(Ph), optionally substituted —(CH₂)₁₋₂(Ph); optionally substituted —CH=CH(Ph); or an unsubstituted 5-6 membered heteroaryl or heterocyclic ring having one to four heteroatoms independently selected from oxygen, nitrogen, or sulfur, or, notwithstanding the definition above, two independent occurrences of R⁺, on the same substituent or different substituents, taken together with the atom(s) to which each R⁺ group is bound, form an optionally substituted 3-12 membered saturated, partially unsaturated, or fully unsaturated monocyclic or bicyclic ring having 0-4 heteroatoms independently selected from nitrogen, oxygen, or sulfur.

Optional substituents on the aliphatic group or the phenyl ring of R⁺ are selected from —NH₂, —NH(C₁₋₄ aliphatic), —N(C₁₋₄ aliphatic)₂, halogen, C₁₋₄ aliphatic, —OH, —O(C₁₋₄ aliphatic), —NO₂, —CN, —CO₂H, —CO₂(C₁₋₄ aliphatic), —O(halo C₁₋₄ aliphatic), or halo(C₁₋₄ aliphatic), wherein each of the foregoing C₁₋₄ aliphatic groups of R⁺ is unsubstituted.

The term "alkylidene chain" refers to a straight or branched carbon chain that may be fully saturated or have one or more units of unsaturation and has two points of attachment to the rest of the molecule.

As detailed above, in some embodiments, two independent occurrences of R° (or R⁺, R, R' or any other variable similarly defined herein), are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

Exemplary rings that are formed when two independent occurrences of R° (or R⁺, R, R' or any other variable similarly defined herein), are taken together with the atom(s) to which each variable is bound include, but are not limited to the following: a) two independent occurrences of R° (or R⁺, R, R' or any other variable similarly defined herein) that are bound to the same atom and are taken together with that atom to form a ring, for example, N(R°)₂, where both occurrences of R° are taken together with the nitrogen atom to form a piperidin-1-yl, piperazin-1-yl, or morpholin-4-yl group; and b) two independent occurrences of R° (or R⁺, R, R' or any other variable similarly defined herein) that are bound to different atoms and are taken together with both of those atoms to form a ring, for example where a phenyl group is substituted with two occurrences of

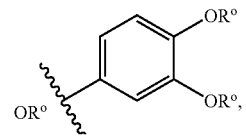

these two occurrences of R° are taken together with the oxygen atoms to which they are bound to form a fused 6-membered oxygen containing ring:

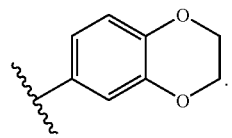

It will be appreciated that a variety of other rings can be formed when two independent occurrences of R° (or R⁺, R, R' or any other variable similarly defined herein) are taken together with the atom(s) to which each variable is bound and that the examples detailed above are not intended to be limiting.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a ¹³C— or ¹⁴C-enriched carbon are within the scope of this invention. Such compounds are useful, for example, as analytical tools or probes in biological assays.

As used herein, the quinazoline ring in formula IA, formula IB, formula IA-1, formula IB-1, formula IIA, formula IIB, formula IIA-1, formula IIB-1, formula IIIA, formula IIIB, formula IIIA-1, formula IIIB-1, and embodiments thereof employs the following numbering system:

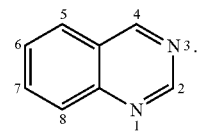

3. Description of Exemplary Compounds:

In one embodiment, the present invention provides a compound of formula IA or formula IB:

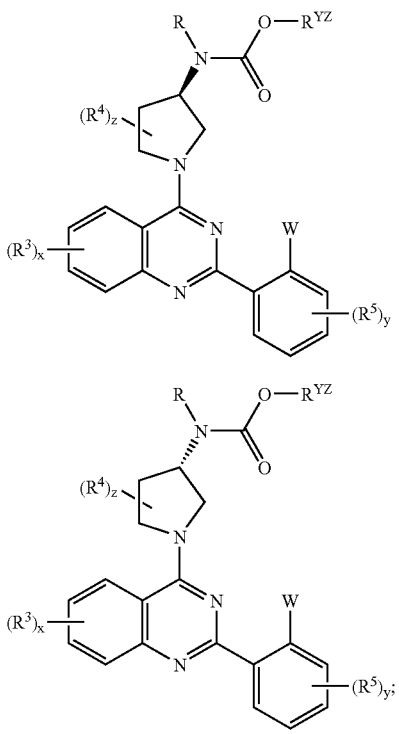

or a pharmaceutically acceptable salt or derivative thereof, wherein:

z is 0-3;

$R^{YZ}$ is $C_1$-$C_6$ aliphatic group, optionally substituted with $w_4$ independent occurrences of $-R^{14}$, wherein $w_4$ is 0-3;

wherein up to two methylene units in $R^{YZ}$ are optionally replaced with $-NR-$, $-O-$, $-COO$, $-OCO-$, $-NRCO-$, $-CONR-$, $-SO_2NR-$, or $-NRSO_2-$;

x and y, each, is independently 0-4;

W is halo, $-OR^{XY}$, $-CHF_2$, or $-CF_3$;

$R^{XY}$ is hydrogen or a group selected from:

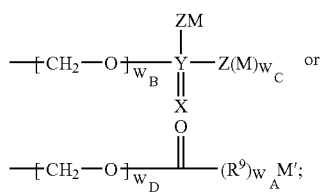

wherein:

each of $w_A$, $w_B$, $w_C$, and $w_D$ is independently 0 or 1;

each M is independently selected from hydrogen, Li, Na, K, Mg, Ca, Ba, $-N(R^7)_4$, $-C_1$-$C_{12}$-alkyl, $-C_2$-$C_{12}$-alkenyl, or $-R^6$; wherein 1 to 4-$CH_2$ radicals of the alkyl or alkenyl group, other than the $-CH_2$ that is bound to Z, is optionally replaced by a heteroatom group selected from O, S, S(O), S(O$_2$), or N(R$^7$); and wherein any hydrogen in said alkyl, alkenyl or $R^6$ is optionally replaced with a substituent selected from oxo, $-OR^7$, $-R^7$, $-N(R^7)_2$, $-N(R^7)_3$, $-R^7OH$, $-CN$, $-CO_2R^7$, $-C(O)-N(R^7)_2$, $-S(O)_2-N(R')_2$, $-N(R^7)-C(O)-R^7$, $-C(O)R^7$, $-S(O)_n-R^7$, $-OCF_3$, $-S(O)_n-R^6$, $-N(R^7)-S(O)_2(R^7)$, halo, $-CF_3$, or $-NO_2$;

n is 0-2;

M' is H, $-C_1$-$C_{12}$-alkyl, $-C_2$-$C_{12}$-alkenyl, or $-R^6$; wherein 1 to 4-$CH_2$ radicals of the alkyl or alkenyl group is optionally replaced by a heteroatom group selected from O, S, S(O), S(O$_2$), or N(R$^7$); and wherein any hydrogen in said alkyl, alkenyl or $R^6$ is optionally replaced with a substituent selected from oxo, $-OR^7$, $-R^7$, $-N(R^7)_2$, $-N(R^7)$, $-R^7OH$, $-CN$, $-CO_2R^7$, $-C(O)-N(R^7)_2$, $-S(O)_2-N(R')_2$, $-N(R^7)-C(O)-R^7$, $-C(O)R^7$, $-S(O)_n-R^7$, $-OCF_3$, $-S(O)_n-R^6$, $-N(R^7)-S(O)_2(R^7)$, halo, $-CF_3$, or $-NO_2$;

Z is $-CH_2-$, $-O-$, $-S-$, $-N(R^7)_2-$; or, when M is absent, then Z is hydrogen, $=O$, or $=S$;

Y is P or S, wherein when Y is S, then Z is not S;

X is O or S;

each $R^7$ is independently selected from hydrogen, or $C_1$-$C_4$ aliphatic, optionally substituted with up to two $Q_1$;

each $Q_1$ is independently selected from a 3-7 membered saturated, partially saturated or unsaturated carbocyclic ring system; or a 5-7 membered saturated, partially saturated or unsaturated heterocyclic ring containing one or more heteroatom or heteroatom group selected from O, N, NH, S, SO, or SO$_2$; wherein $Q_1$, is optionally substituted with up to three substituents selected from oxo, $-OH$, $-O(C_1$-$C_4$ aliphatic), $-C_1$-$C_4$ aliphatic, $-NH_2$, $-NH(C_1$-$C_4$ aliphatic), $-N(C_1$-$C_4$ aliphatic)$_2$, $-N(C_1$-$C_4$ aliphatic)-C(O)-$C_1$-$C_4$ aliphatic, $-(C_1$-$C_4$ aliphatic)-OH, $-CN$, $-CO_2H$, $-CO_2(C_1$-$C_4$ aliphatic), $-C(O)-NH_2$, $-C(O)-NH(C_1$-$C_4$ aliphatic), $-C(O)-N(C_1$-$C_4$ aliphatic)$_2$, halo or $-CF_3$;

$R^6$ is a 5-6 membered saturated, partially saturated or unsaturated carbocyclic or heterocyclic ring system, or an 8-10 membered saturated, partially saturated or unsaturated bicyclic ring system; wherein any of said heterocyclic ring systems contains one or more heteroatoms selected from O, N, S, S(O)$_n$ or N(R$^7$); and wherein any of said ring systems optionally contains 1 to 4 substituents independently selected from OH, $-C_1$-$C_4$ alkyl, $-O-C_1$-$C_4$ alkyl or $-O-C(O)-C_1$-$C_4$ alkyl;

$R^9$ is $C(R^7)_2$, O or $N(R^7)$;

each occurrence of $R^{14}$, $R^3$, $R^4$, and $R^5$ is independently Q-$R^X$; wherein Q is a bond or is a $C_1$-$C_6$ alkylidene chain wherein up to two non-adjacent methylene units of Q are optionally and independently replaced by $-NR-$, $-S-$, $-O-$, $-CS-$, $-CO_2-$, $-OCO-$, $-CO-$, $-COCO-$, $-CONR-$, $-NRCO-$, $-NRCO_2-$, $-SO_2NR-$, $-NRSO_2-$, $-CONRNR-$, $-NRCONR-$, $-OCONR-$, $-NRNR-$, $-NRSO_2NR-$, $-SO-$, $-SO_2-$, $-PO-$, $-PO_2-$, $-OP(O)(OR)-$, or $-POR-$; and each occurrence of $R^X$ is independently selected from $-R'$, halogen, $=NR'$, $-NO_2$, $-CN$, $-OR'$, $-SR'$, $-N(R')_2$, $-NR'COR'$, $-NR'CON(R')_2$, $-NR'CO_2R'$, $-COR'$, $-CO_2R'$, $-OCOR'$, $-CON(R')_2$, $-OCON(R')_2$, $-SOR'$, $-SO_2R'$, $-SO_2N(R')_2$, $-NR'SO_2R'$, $-NR'SO_2N(R')_2$, $-COCOR'$, $-COCH_2COR'$, $-OP(O)(OR')_2$, $-P(O)(OR')_2$, $-OP(O)_2OR'$, $-P(O)_2OR'$, $-PO(R')_2$, or $-OPO(R')_2$; and each occurrence of R is independently hydrogen or $C_1$-$C_6$ aliphatic group having up to three substituents; and each occurrence of R is independently hydrogen or $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein R has up to four substituents; or R and R', two occurrences of R, or two occurrences of R, are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur;

provided that the following compounds are excluded:

carbamic acid, [(3R)-1-[2-(2-hydroxyphenyl)-7-methyl-4-quinazolinyl]-3-pyrrolidinyl]-,phenylmethyl ester;

carbamic acid, [(3R)-1-[2-(2-hydroxyphenyl)-7-methyl-4-quinazolinyl]-3-pyrrolidinyl]-,phenylmethyl ester, monohydrochloride;

carbamic acid, [(3S)-1-[2-(2-hydroxyphenyl)-7-methyl-4-quinazolinyl]-3-pyrrolidinyl]-,1,1-dimethylethyl ester;

carbamic acid, [(3R)-1-[2-(2-hydroxyphenyl)-7-methyl-4-quinazolinyl]-3-pyrrolidinyl]-,1,1-dimethylethyl ester;

carbamic acid, [(3R)-1-[6-fluoro-2-(2-hydroxyphenyl)-4-quinazolinyl]-3-pyrrolidinyl]-,1,1-dimethylethyl ester;

carbamic acid, [(3R)-1-[2-(2-fluoro-6-hydroxyphenyl)-7-methyl-4-quinazolinyl]-3-pyrrolidinyl]-,1,1-dimethylethyl ester;

carbamic acid, [(3R)-1-[2-(2-hydroxyphenyl)-7-methyl-4-quinazolinyl]-3-pyrrolidinyl]-,3-pyridinylmethyl ester, trifluoroacetate (salt);

carbamic acid, [(3R)-1-[2-(2-hydroxyphenyl)-7-methyl-4-quinazolinyl]-3-pyrrolidinyl]-,4-pyridinylmethyl ester, trifluoroacetate (salt);

carbamic acid, [(3R)-1-[2-(2-hydroxyphenyl)-7-methyl-4-quinazolinyl]-3-pyrrolidinyl]-,1,3-benzodioxol-4-ylmethyl ester, trifluoroacetate (salt);

carbamic acid, [(3R)-1-[6-fluoro-2-(2-hydroxyphenyl)-4-quinazolinyl]-3-pyrrolidinyl]-,(tetrahydro-2H-pyran-2-yl)methyl ester, trifluoroacetate (salt); and carbamic acid, [(3R)-1-[2-(2-hydroxyphenyl)-7-methyl-4-quinazolinyl]-3-pyrrolidinyl]-,(tetrahydro-2H-pyran-2-yl)methyl ester.

In another embodiment, the present invention provides a compound of formula IA-1 or formula IB-1:

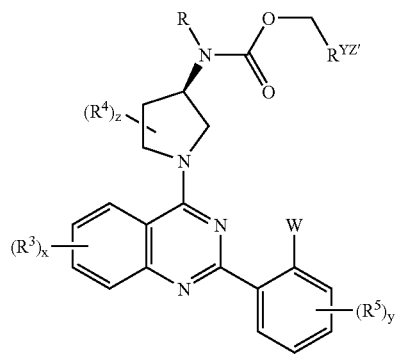

IA-1

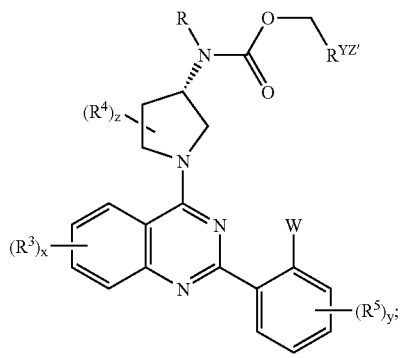

IB-1 or a pharmaceutically acceptable salt or derivative thereof, wherein:

z is 0-3;

$R^{YZ'}$ is a $C_1$-$C_6$ straight or branched alkyl group optionally substituted with $w_4$ independent occurrences of —$R^{14}$, wherein $w_4$ is 0-3;

wherein up to two methylene units in $R^{YZ'}$ are optionally replaced with —O—;

x and y, each, is independently 0-4;

W is halo, —$OR^{XY}$, —$CHF_2$, or —$CF_3$;

$R^{XY}$ is hydrogen or a group selected from:

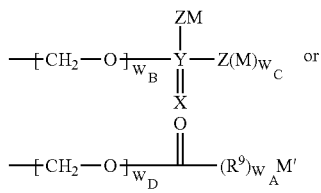

wherein:

each of $w_A$, $w_B$, $w_C$, and $w_D$ is independently 0 or 1;

each M is independently selected from hydrogen, Li, Na, K, Mg, Ca, Ba, —$N(R^7)_4$, —$C_1$-$C_{12}$-alkyl, —$C_2$-$C_{12}$-alkenyl, or —$R^6$; wherein 1 to 4-$CH_2$ radicals of the alkyl or alkenyl group, other than the —$CH_2$ that is bound to Z, is optionally replaced by a heteroatom group selected from O, S, S(O), S(O$_2$), or N($R^7$); and wherein any hydrogen in said alkyl, alkenyl or $R^6$ is optionally replaced with a substituent selected from oxo, —$OR^7$, —$R^7$, —$N(R^7)_2$, —$N(R^7)_3$, —$R^7OH$, —CN, —$CO_2R^7$, —C(O)—$N(R^7)_2$, —$S(O)_2$—N($R^7$)$_2$, —N($R^7$)—C(O)—$R^7$, —C(O)$R^7$, —$S(O)_n$—$R^7$, —$OCF_3$, —$S(O)_n$—$R^6$, —N($R^7$)—$S(O)_2(R^7)$, halo, —$CF_3$, or —$NO_2$;

n is 0-2;

M' is H, —$C_1$-$C_{12}$-alkyl, —$C_2$-$C_{12}$-alkenyl, or —$R^6$; wherein 1 to 4-$CH_2$ radicals of the alkyl or alkenyl group is optionally replaced by a heteroatom group selected from O, S, S(O), S(O$_2$), or N($R^7$); and wherein any hydrogen in said alkyl, alkenyl or $R^6$ is optionally replaced with a substituent selected from oxo, —$OR^7$, —$R^7$, —$N(R^7)_2$, —$N(R^7)_3$, —$R^7OH$, —CN, —$CO_2R^7$, —C(O)—$N(R^7)_2$, —$S(O)_2$—N($R^7$)$_2$, —N($R^7$)—C(O)—$R^7$, —C(O)$R^7$, —$S(O)^n$—$R^7$, —$OCF_3$, —$S(O)_n$—$R^6$, —N($R^7$)—$S(O)_2(R^7)$, halo, —$CF_3$, or —$NO_2$;

Z is —$CH_2$—, —O—, —S—, —$N(R^7)_2$—; or, when M is absent, then Z is hydrogen, =O, or =S;

Y is P or S, wherein when Y is S, then Z is not S;

X is O or S;

each $R^7$ is independently selected from hydrogen, or $C_1$-$C_4$ aliphatic, optionally substituted with up to two Ql;

each $Q_1$ is independently selected from a 3-7 membered saturated, partially saturated or unsaturated carbocyclic ring system; or a 5-7 membered saturated, partially saturated or unsaturated heterocyclic ring containing one or more heteroatom or heteroatom group selected from O, N, NH, S, SO, or $SO_2$; wherein $Q_1$ is optionally substituted with up to three substituents selected from oxo, —OH, —O($C_1$-$C_4$ aliphatic), —$C_1$-$C_4$ aliphatic, —$NH_2$, —NH($C_1$-$C_4$ aliphatic), —N($C_1$-$C_4$ aliphatic)$_2$, —N($C_1$-$C_4$ aliphatic)-C(O)—$C_1$-$C_4$ aliphatic, —($C_1$-$C_4$ aliphatic)-OH, —CN, —$CO_2$H, —$CO_2$($C_1$-$C_4$ aliphatic), —C(O)—$NH_2$, —C(O)—NH($C_1$-$C_4$ aliphatic), —C(O)—N($C_1$-$C_4$ aliphatic)$_2$, halo or —$CF_3$;

$R^6$ is a 5-6 membered saturated, partially saturated or unsaturated carbocyclic or heterocyclic ring system, or an 8-10 membered saturated, partially saturated or unsaturated bicyclic ring system; wherein any of said heterocyclic ring systems contains one or more heteroatoms selected from O, N, S, S(O)$_n$, or N($R^7$); and wherein any of said ring systems optionally contains 1 to 4 substituents independently selected from OH, —$C_1$-$C_4$ alkyl, —O—$C_1$-$C_4$ alkyl or —O—C(O)—$C_1$-$C_4$ alkyl;

$R^9$ is C($R^7$)$_2$, O or N($R^7$);

each occurrence of $R^{14}$, $R^3$, $R^4$, and $R^5$ is independently Q-Rx; wherein Q is a bond or is a $C_1$-$C_6$ alkylidene chain wherein up to two non-adjacent methylene units of Q are optionally and independently replaced by —NR—, —S—, —O—, —CS—, —$CO_2$—, —OCO—, —CO—, —COCO—, —CONR—, —NRCO—, —$NRCO_2$—, —$SO_2$NR—, —$NRSO_2$—, —CONRNR—, —NRCONR—, —OCONR—, —NRNR—, —$NRSO_2$NR—, —SO—, —$SO_2$—, —PO—, —$PO_2$—, —OP(O)(OR)—, or —POR—; and each occurrence of $R^X$ is independently selected from —R', halogen, =NR', —$NO_2$, —CN, —OR', —SR', —N(R')$_2$, —NR'COR', —NR'CON(R')$_2$, —NR'$CO_2$R', —COR', —$CO_2$R', —OCOR', —CON(R')$_2$, —OCON(R')$_2$, —SOR', —$SO_2$R', —$SO_2$N(R')$_2$, —NR'$SO_2$R', —NR'$SO_2$N(R')$_2$, —COCOR', —$COCH_2$COR', —OP(O)(OR')$_2$, —P(O)(OR')$_2$, —OP(O)$_2$OR', —P(O)$_2$OR', —PO(R')$_2$, or —OPO(R')$_2$; and each occurrence of R is independently hydrogen or $C_1$-$C_6$ aliphatic group having up to three substituents; and each occurrence of R is independently hydrogen or $C_1$-$C_6$ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur, wherein R' has up to four substituents; or R and R', two occurrences of R, or two occurrences of R', are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur.

In one embodiment, R is hydrogen. In another embodiment, R is $C_1$-$C_6$ aliphatic. In another embodiment R is $C_1$-$C_6$ straight or branched alkyl. Exemplary R includes $C_1$-$C_6$ straight or branched alkyl, e.g., methyl, ethyl, propyl, or butyl.

In one embodiment, R' is hydrogen. In another embodiment, R' is $C_1$-$C_6$ aliphatic.

In one embodiment, R' is a $C_1$-$C_6$ aliphatic group, optionally substituted with up to 3 substituents selected from halo, —CN, —$CF_3$, —$CHF_2$, —$OCF_3$, or —$OCHF_2$, wherein up to two methylene units of said $C_1$-$C_6$ aliphatic is optionally replaced with —CO—, —CONH($C_1$-$C_4$ alkyl)-, —$CO_2$—, —OCO—, —N($C_1$-$C_4$ alkyl)$CO_2$—, —O—, —N($C_1$-$C_4$ alkyl)CON($C_1$-$C_4$ alkyl)-, —OCON($C_1$-$C_4$ alkyl)-, —N($C_1$-$C_4$ alkyl)CO—, —S—, —N($C_1$-$C_4$ alkyl)-, —$SO_2$N($C_1$-$C_4$ alkyl)-, N($C_1$-$C_4$ alkyl)$SO_2$—, or —N($C_1$-$C_4$ alkyl)$SO_2$N($C_1$-$C_4$ alkyl)-.

In one embodiment, R' is a 3-8 membered saturated, partially unsaturated, or fully unsaturated monocyclic ring having 0-3 heteroatoms independently selected from nitrogen, oxygen, or sulfur, wherein R' is optionally substituted with up to 3 substituents selected from halo, —CN, —$CF_3$, —$CHF_2$, —$OCF_3$, —$OCHF_2$, or $C_1$-$C_6$ alkyl, wherein up to two methylene units of said $C_1$-$C_6$ alkyl is optionally replaced with —CO—, —CONH($C_1$-$C_4$ alkyl)-, —$CO_2$—, —OCO—, —N($C_1$-$C_4$ alkyl)$CO_2$—, —O—, —N($C_1$-$C_4$ alkyl)CON($C_1$-$C_4$ alkyl)-, —OCON($C_1$-$C_4$ alkyl)-, —N($C_1$-$C_4$ alkyl)CO—, —S—, —N($C_1$-$C_4$ alkyl)-, —$SO_2$N($C_1$-$C_4$ alkyl)-, N($C_1$-$C_4$ alkyl)$SO_2$—, or —N($C_1$-$C_4$ alkyl)$SO_2$N($C_1$-$C_4$ alkyl)-.

In one embodiment, R' is an 8-12 membered saturated, partially unsaturated, or fully unsaturated bicyclic ring system having 0-5 heteroatoms independently selected from nitrogen, oxygen, or sulfur; wherein R' is optionally substituted with up to 3 substituents selected from halo, —CN, —$CF_3$, —$CHF_2$, —$OCF_3$, —$OCHF_2$, or $C_1$-$C_6$ alkyl, wherein up to two methylene units of said $C_1$-$C_6$ alkyl is optionally replaced with —CO—, —CONH($C_1$-$C_4$ alkyl)-, —$CO_2$—, —OCO—, —N($C_1$-$C_4$ alkyl)$CO_2$—, —O—, —N($C_1$-$C_4$ alkyl)CON($C_1$-$C_4$ alkyl)-, —OCON($C_1$-$C_4$ alkyl)-, —N($C_1$-$C_4$ alkyl)CO—, —S—, —N($C_1$-$C_4$ alkyl)-, —$SO_2$N($C_1$-$C_4$ alkyl)-, —N($C_1$-$C_4$ alkyl)$SO_2$—, or —N($C_1$-$C_4$ alkyl)$SO_2$N($C_1$-$C_4$ alkyl)-.

In one embodiment, two occurrences of R' are taken together with the atom(s) to which they are bound to form an optionally substituted 3-12 membered saturated, partially unsaturated, or fully unsaturated monocyclic or bicyclic ring having 0-4 heteroatoms independently selected from nitrogen, oxygen, or sulfur, wherein R' is optionally substituted with up to 3 substituents selected from halo, —CN, —$CF_3$, —$CHF_2$, —$OCF_3$, —$OCHF_2$, or $C_1$-$C_6$ alkyl, wherein up to two methylene units of said $C_1$-$C_6$ alkyl is optionally replaced with —CO—, —CONH($C_1$-$C_4$ alkyl)-, —$CO_2$—, —OCO—, —N($C_1$-$C_4$ alkyl)$CO_2$—, —O—, —N($C_1$-$C_4$ alkyl)CON($C_1$-$C_4$ alkyl)-, —OCON($C_1$-$C_4$ alkyl)-, —N($C_1$-$C_4$ alkyl)CO—, —S—, —N($C_1$-$C_4$ alkyl)-, —$SO_2$N($C_1$-$C_4$ alkyl)-, —N($C_1$-$C_4$ alkyl)$SO_2$—, or —N($C_1$-$C_4$ alkyl)$SO_2$N($C_1$-$C_4$ alkyl)-.

In another embodiment, W is OH.

In still another embodiment, $R^{XY}$ is:

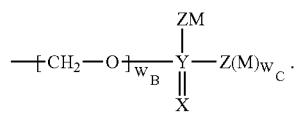

In certain embodiment, Y is P and X is O.

In another embodiment, each Z is —O—.

In yet another embodiment, $R^{XY}$ is selected from:

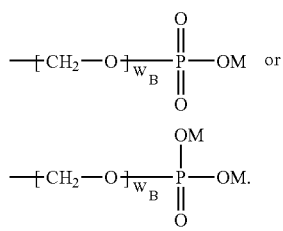

In yet another embodiment, $R^{XY}$ is selected from:

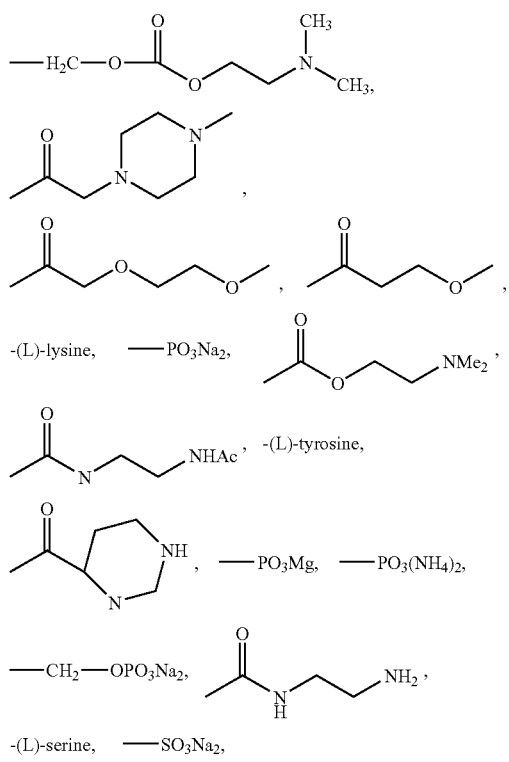

-(L)-lysine, —PO$_3$Na$_2$,

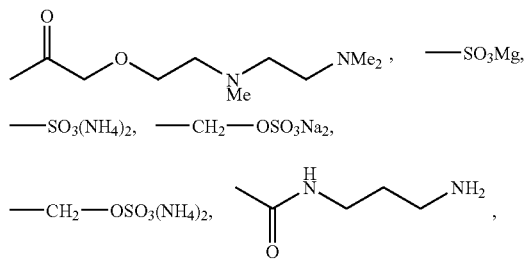

-(L)-tyrosine,

—PO$_3$Mg, —PO$_3$(NH$_4$)$_2$,

—CH$_2$—OPO$_3$Na$_2$,

-(L)-serine, —SO$_3$Na$_2$,

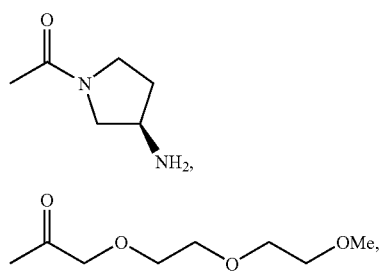

—SO$_3$Mg, —SO$_3$(NH$_4$)$_2$, —CH$_2$—OSO$_3$Na$_2$, —CH$_2$—OSO$_3$(NH$_4$)$_2$,

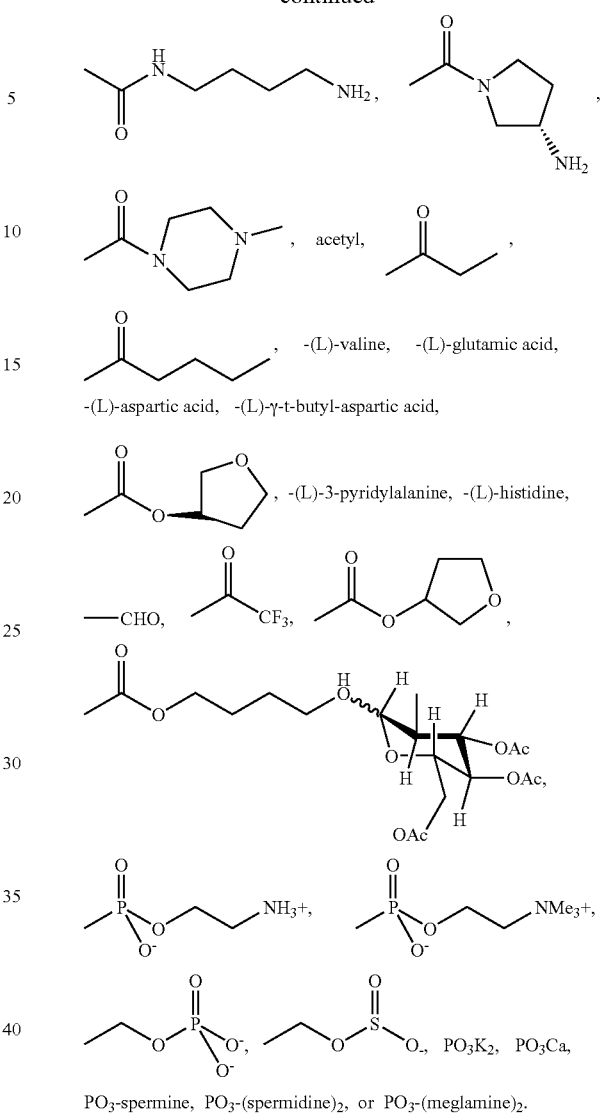

, -(L)-valine, -(L)-glutamic acid, -(L)-aspartic acid, -(L)-γ-t-butyl-aspartic acid, , -(L)-3-pyridylalanine, -(L)-histidine,

—CHO,

PO$_3$-spermine, PO$_3$-(spermidine)$_2$, or PO$_3$-(meglamine)$_2$.

In yet another embodiment, $R^{XY}$ is selected from:

| $R^{XY}$ |
| --- |

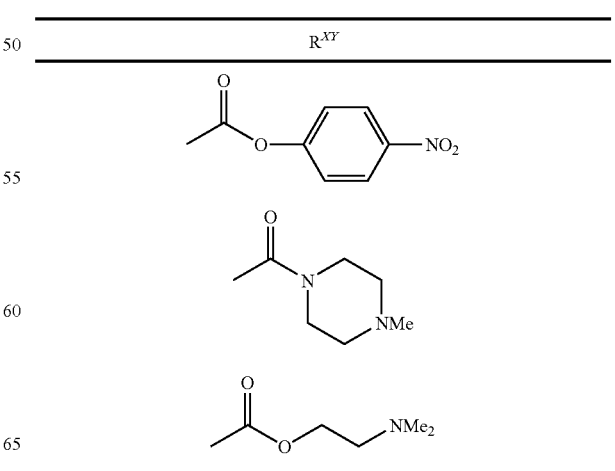

23
-continued
R<sup>XY</sup>
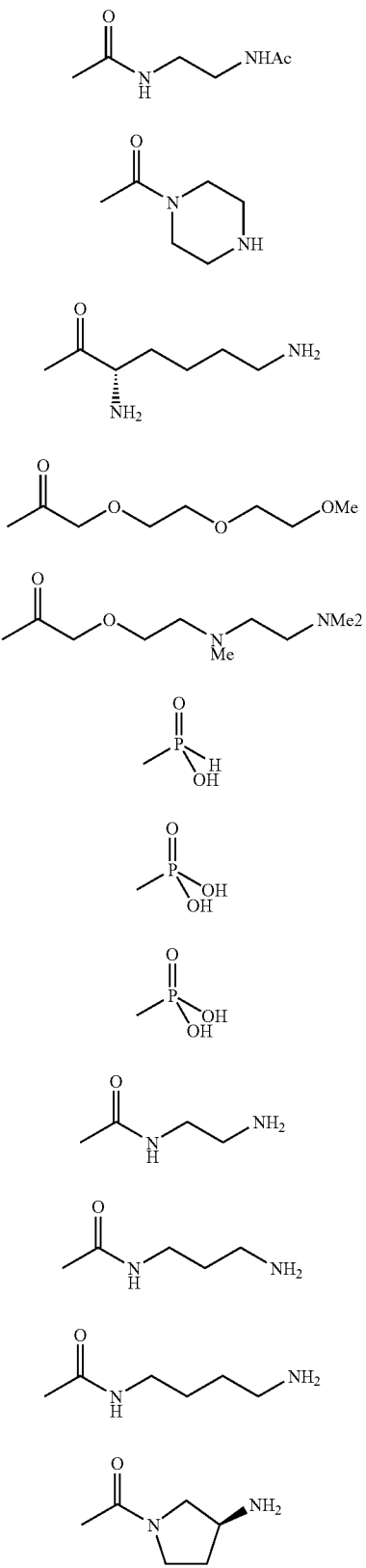
24
-continued
R<sup>XY</sup>
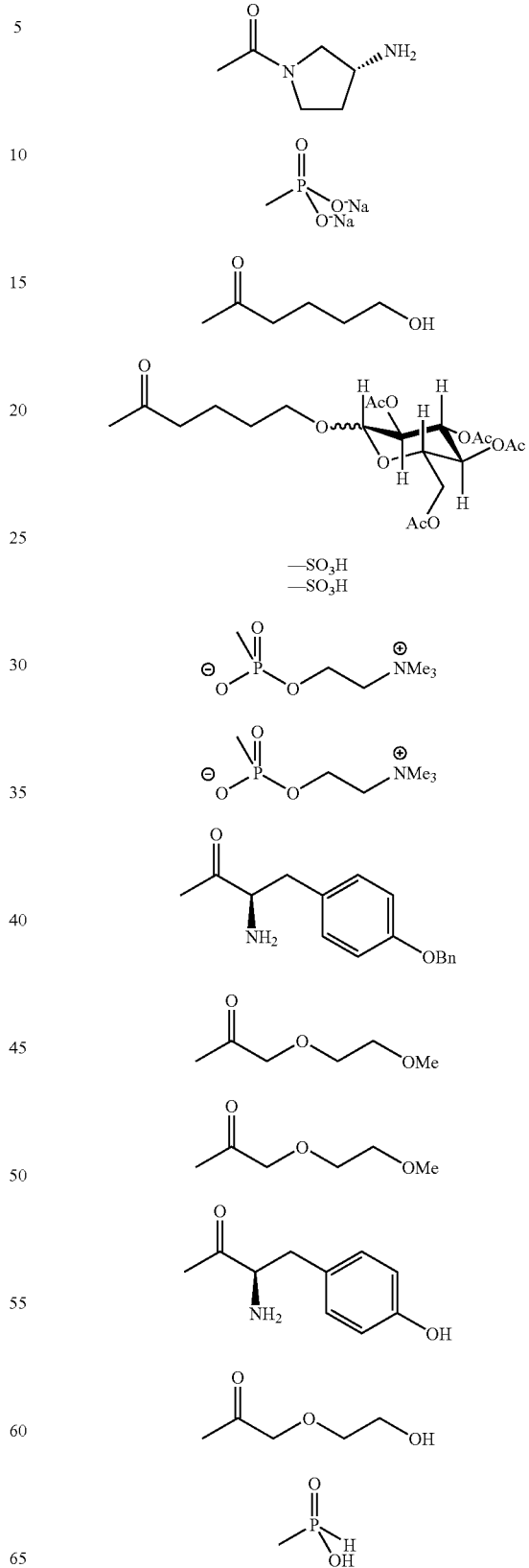
—SO$_3$H
—SO$_3$H $R^{XY}$

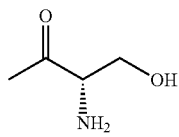

PO₃K₂
PO₃Ca
PO₃Mg

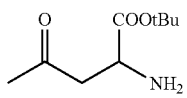

In one embodiment, x is 0-2. Or, x is 1 or 2. Or, x is 1.

In one embodiment, $R^3$ is present at the 6- or 7-position of the quinazoline ring.

In another embodiment, $R^3$ is selected from halo, —CN, —NO₂, —N(R')₂, —CH₂N(R')₂, —OR', —CH₂OR', —SR', —CH₂SR', —COOR', —NRCOR', —CON(R')₂, —OCON(R')₂, —COR', —NHCOOR', —SO₂R', —SO₂N(R')₂, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or heterocycloaliphatic $C_1$-$C_6$alkyl.

In one embodiment, $R^3$ is independently —Cl, —Br, —F, —CF₃, —OCF₃, —CH₃, —CH₂CH₃, —CN, —COOH, —NH₂, —N(CH₃)₂, —N(Et)₂, —N(iPr)₂, —O(CH₂)₂OCH₃, —CONH₂, —COOCH₃, —OH, —OCH₃, —OCH₂CH₃, —CH₂OH, —NHCOCH₃, —NHCOCH(CH₃)₂, —SO₂NH₂, —CONH(cyclopropyl), —CONHCH₃, —CONHCH₂CH₃, or an optionally substituted group selected from piperidinyl, piperazinyl, morpholino, phenyl, phenyloxy, benzyl, or benzyloxy.

In another embodiment, each $R^3$ group is independently halogen, —CN, optionally substituted $C_1$-$C_6$alkyl, —OR', —N(R')₂, —CON(R')₂, or —NRCOR'.

In one embodiment, x is 1 or 2, and each $R^3$ group is —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN.

In yet another embodiment, x is 1 and $R^3$ is at the 6-position of the quinazoline ring and is selected from —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN.

In yet another embodiment, x is 1 and $R^3$ is at the 6-position of the quinazoline ring and is —Cl, —CH₃, —CH₂CH₃, —F, —CF₃, —OCF₃, —OCH₃, or —OCH₂CH₃.

In one embodiment, $R^3$ is at the 6-position of the quinazoline ring and is —CON(R')₂, or —NRCOR'.

In another embodiment, x is 1 and $R^3$ is at the 7-position of the quinazoline ring and is selected from —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN.

In yet another embodiment, x is 1 and $R^3$ is at the 7-position of the quinazoline ring and is —Cl, —CH₃, —CH₂CH₃, —F, —CF₃, —OCF₃, —OCH₃, or —OCH₂CH₃. Or, x is 1 and $R^3$ is at the 7-position of the quinazoline ring and is —CON(R')₂, or —NRCOR'.

In one embodiment, y is 0-4 and $R^5$ is independently halogen, —CN, —NO₂, —N(R')₂, —CH₂N(R')₂, —OR', —CH₂OR', —SR', —CH₂SR', —NRCOR', —CON(R')₂, —S(O)₂N(R')₂, —OCOR', —COR', —CO₂R', —OCON(R')₂, —NR'SO₂R', —OP(O)(OR')₂, —P(O)(OR')₂, —OP(O)₂OR', —P(O)₂OR', —PO(R')₂, —OPO(R')₂, or an optionally substituted group selected from $C_1$-$C_6$aliphatic, aryl, heteroaryl, cycloaliphatic, heterocycloaliphatic, aryl$C_1$-$C_6$alkyl, heteroaryl $C_1$-$C_6$alkyl, cycloaliphatic $C_1$-$C_6$alkyl, or heterocycloaliphatic $C_1$-$C_6$alkyl.

In another embodiment, $R^5$ is independently —Cl, —Br, —F, —CF₃, —CH₃, —CH₂CH₃, —CN, —COOH, —NH₂, —N(CH₃)₂, —N(Et)₂, —N(iPr)₂, —O(CH₂)₂OCH₃, —CONH₂, —COOCH₃, —OH, —OCH₃, —OCH₂CH₃, —CH₂OH, —NHCOCH₃, —SO₂NH₂, —SO₂NHC(CH₃)₂, —OCOC(CH₃)₃, —OCOCH₂C(CH₃)₃, —O(CH₂)₂N(CH₃)₂, 4-CH₃-piperazin-1-yl, —OCOCH(CH₃)₂, —OCO(cyclopentyl), —COCH₃, optionally substituted phenoxy, or optionally substituted benzyloxy.

In certain embodiments, z is 0-2. In other embodiments, z is 0 and the ring is unsubstituted. Preferred $R^4$ groups, when present, are each independently halogen, —CN, —NO₂, —N(R')₂, —CH₂N(R')₂, —OR', —CH₂OR', —SR', —CH₂SR', —COOR', —NRCOR', —CON(R')₂, —OCON(R')₂, —COR', —NHCOOR', —SO₂R', —SO₂N(R')₂, or an optionally substituted group selected from $C_1$-$C_6$aliphatic, aryl, heteroaryl, cycloaliphatic, heterocycloaliphatic, aryl $C_1$-$C_6$alkyl, heteroaryl $C_1$-$C_6$alkyl, cycloaliphatic $C_1$-$C_6$alkyl, or heterocycloaliphatic $C_1$-$C_6$alkyl. Other exemplary $R^4$ groups are —Cl, —Br, —F, —CF₃, —CH₃, —CH₂CH₃, —CN, —COOH, —N(CH₃)₂, —N(Et)₂, —N(iPr)₂, —O(CH₂)₂OCH₃, —CONH₂, —COOCH₃, —OH, —CH₂OH, —NHCOCH₃, —SO₂NH₂, —SO₂(CH₂)₃CH₃, —SO₂CH(CH₃)₂, —SO₂N(CH₃)₂, —SO₂CH₂CH₃, —C(O)OCH₂CH(CH₃)₂, —C(O)NHCH₂CH(CH₃)₂, —NH-COOCH₃, —C(O)C(CH₃)₃, —COO(CH₂)₂CH₃, —C(O)NHCH(CH₃)₂, —C(O)CH₂CH₃, or an optionally substituted group selected from piperidinyl, piperazinyl, morpholino, $C_{1-4}$alkoxy, phenyl, phenyloxy, benzyl, benzyloxy, —CH₂cyclohexyl, pyridyl, —CH₂pyridyl, or —CH₂thiazolyl.

In certain embodiments, x is 0-2. In other embodiments, x is 1 or 2. In still other embodiments x is 1 and $R^3$ is substituted at the 6- or 7-position of the quinazoline ring. When the quinazoline ring is substituted (x is 1-4), $R^3$ groups are halogen, —CN, —NO₂, —N(R')₂, —CH₂N(R')₂, —OR', —CH₂OR', —SR', —CH₂SR', —COOR', —NRCOR', —CON(R')₂, —OCON(R')₂, —COR', —NHCOOR', —SO₂R', —SO₂N(R')₂, or an optionally substituted group selected from $C_1$-$C_6$aliphatic, aryl, heteroaryl, cycloaliphatic, heterocycloaliphatic, aryl$C_1$-$C_6$alkyl, heteroaryl $C_1$-$C_6$alkyl, cycloaliphatic $C_1$-$C_6$alkyl, or heterocycloaliphatic $C_1$-$C_6$alkyl. In still other embodiments, each occurrence of $R^3$ is independently —Cl, —Br, —F, —CF₃, —OCF₃, —CH₃, —CH₂CH₃, —CN, —COOH, —NH₂, —N(CH₃)₂, —N(Et)₂, —N(iPr)₂, —O(CH₂)₂OCH₃, —CONH₂, —COOCH₃, —OH, —OCH₃, —OCH₂CH₃, —CH₂OH, —NHCOCH₃, —NHCOCH(CH₃)₂, —SO₂NH₂, —CONH(cyclopropyl), —CONHCH₃, —CONHCH₂CH₃, or an optionally substituted group selected from piperidinyl, piperazinyl, morpholino, phenyl, phenyloxy, benzyl, or benzyloxy. In still other embodiments, x is 1 or 2 and each $R^3$ group is independently halogen, —CN, optionally substituted $C_1$-$C_6$alkyl, —OR', —N(R')₂, —CON(R')₂, or —NRCOR'. In yet other embodiments, x is 1 or 2, and each $R^3$ group is —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN. In still other embodiments, x is 1 and $R^3$ is at the 6-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In yet other embodiments, x is 1 and R$^3$ is at the 7-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In other embodiments, x is 1 and R$^3$ is at the 6-position of the quinazoline ring and is —Cl, —CH$_3$, —CH$_2$CH$_3$, —F, —CF$_3$, —OCF$_3$, —OCH$_3$, or —OCH$_2$CH$_3$. In still other embodiments, x is 1 and R$^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$. In other embodiments, x is 1 and R$^3$ is at the 6-position of the quinazoline ring and is —CON(R')$_2$, or —NRCOR'. In yet other embodiments, x is 1 and R$^3$ is at the 7-position of the quinazoline ring and is —CON(R')$_2$, or —NRCOR'.

In some embodiments, y is 0-4 and R$^5$ group, when present, is each independently halogen, —CN, —NO$_2$, —N(R')$_2$, —CH$_2$N(R')$_2$, —OR', —CH$_2$OR', —SR', —CH$_2$SR', —NRCOR', —CON(R')$_2$, —S(O)$_2$N(R')$_2$, —OCOR', —COR', —CO$_2$R', —OCON(R')$_2$, —NR'SO$_2$R', —OP(O)(OR')$_2$, —P(O)(OR')$_2$, —OP(O)$_2$OR', —P(O)$_2$OR', —PO(R')$_2$, —OPO(R')$_2$, or an optionally substituted group selected from C$_1$-C$_6$aliphatic, aryl, heteroaryl, cycloaliphatic, heterocycloaliphatic, arylC$_1$-C$_6$alkyl, heteroaryl C$_1$-C$_6$alkyl, cycloaliphatic C$_1$-C$_6$alkyl, or heterocycloaliphatic C$_1$-C$_6$alkyl.

In yet other embodiments, y is 0-4 and each occurrence of R$^5$ is independently —Cl, —Br, —F, —CF$_3$, —CH$_3$, —CH$_2$CH$_3$, —CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —SO$_2$NH$_2$, —SO$_2$NHC(CH$_3$)$_2$, —OCOC(CH$_3$)$_3$, —OCOCH$_2$C(CH$_3$)$_3$, —O(CH$_2$)$_2$N(CH$_3$)$_2$, 4-CH$_3$-piperazin-1-yl, —OCOCH(CH$_3$)$_2$, —OCO(cyclopentyl), —COCH$_3$, optionally substituted phenoxy, or optionally substituted benzyloxy.

In yet another embodiment, z is 0-4, and R$^4$ groups, when present, are each independently halogen, —CN, —NO$_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, —COR', —NHCOOR', —SO$_2$R', —SO$_2$N(R')$_2$, or an optionally substituted group selected from C$_1$-C$_6$aliphatic, aryl, heteroaryl, cycloaliphatic, heterocycloaliphatic, aryl C$_1$-C$_6$alkyl, heteroaryl C$_1$-C$_6$alkyl, cycloaliphatic C$_1$-C$_6$alkyl, or heterocycloaliphatic C$_1$-C$_6$alkyl.

In still other embodiments, z is 0-4 and R$^4$ groups are each independently —Cl, —Br, —F, —CF$_3$, —CH$_3$, —CH$_2$CH$_3$, —CN, —COOH, —N(CH$_3$)$_2$, —N(Et)$_2$, —N(iPr)$_2$, —O(CH$_2$)$_2$OCH$_3$, —CONH$_2$, —COOCH$_3$, —OH, —CH$_2$OH, —NHCOCH$_3$, —SO$_2$NH$_2$, —SO$_2$(CH$_2$)$_3$CH$_3$, —SO$_2$CH(CH$_3$)$_2$, —SO$_2$N(CH$_3$)$_2$, —SO$_2$CH$_2$CH$_3$, —C(O)OCH$_2$CH(CH$_3$)$_2$, —C(O)NHCH$_2$CH(CH$_3$)$_2$, —NHCOOCH$_3$, —C(O)C(CH$_3$)$_3$, —COO(CH$_2$)$_2$CH$_3$, —C(O)NHCH(CH$_3$)$_2$, —C(O)CH$_2$CH$_3$, or an optionally substituted group selected from piperidinyl, piperazinyl, morpholino, C$_{1-4}$alkoxy, phenyl, phenyloxy, benzyl, benzyloxy, —CH$_2$cyclohexyl, pyridyl, —CH$_2$pyridyl, or —CH$_2$thiazolyl.

For compounds described directly above, in some embodiments, x is 0-4, and R$^3$ groups, when present, are each independently halogen, —CN, —NO$_2$, —N(R')$_2$, —CH$_2$N(R')$_2$, —OR', —CH$_2$OR', —SR', —CH$_2$SR', —COOR', —NRCOR', —CON(R')$_2$, —OCON(R')$_2$, —COR', —NHCOOR', —SO$_2$R', —SO$_2$N(R')$_2$, or an optionally substituted group selected from C$_1$-C$_6$aliphatic, aryl, heteroaryl, cycloaliphatic, heterocycloaliphatic, aryl C$_1$-C$_6$alkyl, heteroaryl C$_1$-C$_6$alkyl, cycloaliphatic C$_1$-C$_6$alkyl, or heterocycloaliphatic C$_1$-C$_6$alkyl.

In yet other embodiments, x is 1 or 2, and each occurrence of R$^3$ is independently —Cl, —Br, —F, —CF$_3$, —OCF$_3$, —CH$_3$, —CH$_2$CH$_3$, —CN, —COOH, —NH$_2$, —N(CH$_3$)$_2$, —N(Et)$_2$, —N(iPr)$_2$, —O(CH$_2$)$_2$OCH$_3$, —CONH$_2$, —COOCH$_3$, —OH, —OCH$_3$, —OCH$_2$CH$_3$, —CH$_2$OH, —NHCOCH$_3$, —NHCOCH(CH$_3$)$_2$, —SO$_2$NH$_2$, —CONH(cyclopropyl), —CONHCH$_3$, —CONHCH$_2$CH$_3$, or an optionally substituted group selected from piperidinyl, piperazinyl, morpholino, phenyl, phenyloxy, benzyl, or benzyloxy.

In still other embodiments, x is 1 or 2 and each R$^3$ group is independently halogen, —CN, optionally substituted C$_1$-C$_6$alkyl, —OR', —N(R')$_2$, —CON(R')$_2$, or —NRCOR'.

In yet other embodiments, x is 1 or 2, and each R$^3$ group is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In still other embodiments, x is 1 and R$^3$ is at the 6-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In yet other embodiments, x is 1 and R$^3$ is at the 7-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN.

In still other embodiments, x is 1 and R$^3$ is at the 6-position of the quinazoline ring and is —Cl, —CH$_3$, —CH$_2$CH$_3$, —F, —CF$_3$, —OCF$_3$, —OCH$_3$, or —OCH$_2$CH$_3$.

In yet other embodiments, x is 1 and R$^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$.

In still other embodiments, x is 1 and R$^3$ is at the 6-position of the quinazoline ring and is —CON(R')$_2$, or —NRCOR'.

In yet other embodiments, x is 1 and R$^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$.

In yet other embodiments for compounds described directly above, x is 1 and R$^3$ is at the 6-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In still other embodiments, x is 1 and R$^3$ is at the 7-position of the quinazoline ring and is —Cl, —CH$_3$, —CH$_2$CH$_3$, —F, —CF$_3$, —OCF$_3$, —CONHCH$_3$, —CONHCH$_2$CH$_3$, —CONH(cyclopropyl), —OCH$_3$, —NH$_2$, —OCH$_2$CH$_3$, or —CN. In yet other embodiments, x is 1 and R$^3$ is at the 6-position of the quinazoline ring and is —Cl, —CH$_3$, —CH$_2$CH$_3$, —F, —CF$_3$, —OCF$_3$, —OCH$_3$, or —OCH$_2$CH$_3$. In still other embodiments, x is 1 and R$^3$ is at the 7-position of the quinazoline ring and is —Cl, —CH$_3$, —CH$_2$CH$_3$, —F, —CF$_3$, —OCF$_3$, —OCH$_3$, or —OCH$_2$CH$_3$. In yet other embodiments, x is 1 and R$^3$ is at the 6-position of the quinazoline ring and is —CON(R')$_2$, or —NRCOR'. In yet other embodiments, x is 1 and R$^3$ is at the 7-position of the quinazoline ring and is —CON(R')$_2$, or —NRCOR'.

In one embodiment of formula IA or formula IB, R$^{YZ}$ is —CH$_3$, —CH$_2$CH$_3$, —CH(CH$_3$)$_2$, —CH$_2$CH$_2$CH$_3$, —CH$_2$CH(CH$_3$)$_2$, or —CH$_2$C(CH$_3$)$_3$. In another embodiment of formula IA or formula IB, R$^{YZ}$ is C$_1$-C$_6$ aliphatic wherein one methylene unit is replaced by —O—. In one embodiment of formula IA or formula IB, R$^{YZ}$ is —CH$_3$, —CH$_2$CH$_3$, —CH(CH$_3$)$_2$, —CH$_2$CH$_2$CH$_3$, —CH$_2$ $CH_2OCH_3$, —$CH_2CH(CH_3)_2$, or —$CH_2C(CH_3)_3$. In another embodiment of formula IB, $R^{YZ}$ is —$CH(CH_3)_2$, or —$CH_2CH_2OCH_3$.

In one embodiment of formula IA-1, $R^{YZ'}$ is —$CH_3$, —$CH_2CH_3$, —$CH(CH_3)_2$, —$C(CH_3)_3$, or —$CH_2OCH_3$. In one embodiment of formula IB-1, $R^{YZ}$ is —$CH_3$, —$CH_2CH_3$, —$CH(CH_3)_2$, —$C(CH_3)_3$, or —$CH_2OCH_3$. In another embodiment of formula IB-1, $R^{YZ'}$ is —$CH(CH_3)_2$ or —$CH_2OCH_3$.

In one embodiment, the present invention provides a compound of formula IIA or formula IIB:

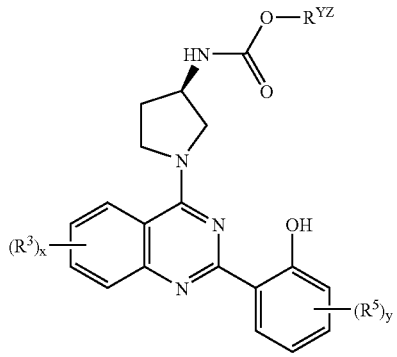

IIA

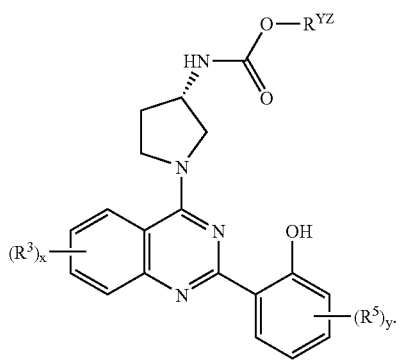

IIB

In one embodiment of formula IIA or formula IIB, $R^{YZ}$ is —$CH_3$, —$CH_2CH_3$, —$CH(CH_3)_2$, —$CH_2CH_2CH_3$, —$CH_2CH(CH_3)_2$, or —$CH_2C(CH_3)_3$. In another embodiment of formula IIA or formula IIB, $R^{YZ}$ is —$CH_3$, —$CH_2CH_3$, —$CH(CH_3)_2$, —$CH_2CH_2CH_3$, —$CH_2CH_2OCH_3$, —$CH_2CH(CH_3)_2$, or —$CH_2C(CH_3)_3$. In another embodiment of formula IIB, $R^{YZ}$ is —$CH(CH_3)_2$ or —$CH_2CH_2OCH_3$.

In another embodiment, the present invention provides a compound of formula IIA-1 or formula IIB-1:

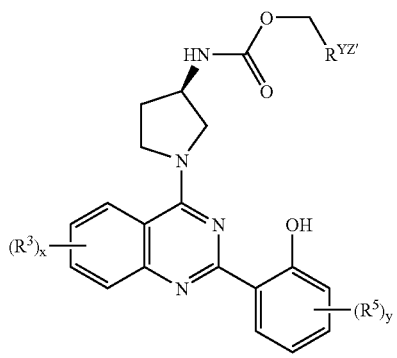

IIA-1

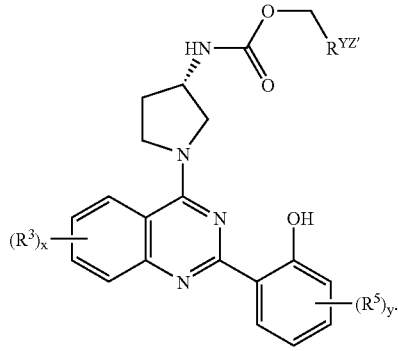

IIB-1

In one embodiment of formula IIA-1, $R^{YZ'}$ is —$CH_3$, —$CH_2CH_3$, —$CH(CH_3)_2$, —$C(CH_3)_3$, or —$CH_2OCH_3$. In one embodiment of formula IIB-1, $R^{YZ'}$ is —$CH_3$, —$CH_2CH_3$, —$CH(CH_3)_2$, —$C(CH_3)_3$, or —$CH_2OCH_3$. In another embodiment of formula IIB-1, $R^{YZ'}$ is —$CH(CH_3)_2$ or —$CH_2OCH_3$.

In another embodiment, the present invention provides a compound of formula IIIA or formula IIIB:

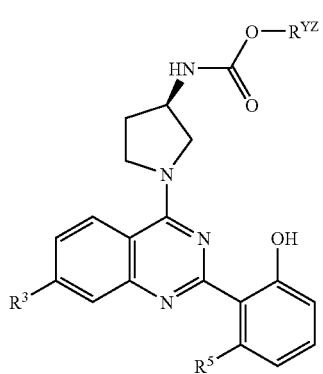

IIIA

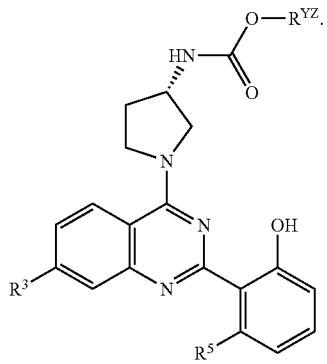

IIIB

In one embodiment of formula IIIA or formula IIIB, $R^{YZ}$ is $C_1$-$C_6$ alkyl. In another embodiment of formula IIIA or formula IIIB, $R^{YZ}$ is $C_1$-$C_6$ alkyl wherein one methylene unit is replaced by —O—.

In one embodiment of formula IIIA or formula IIIB, $R^{YZ}$ is —$CH_3$, —$CH_2CH_3$, —$CH(CH_3)_2$, —$CH_2CH_2CH_3$, —$CH_2CH(CH_3)_2$, or —$CH_2C(CH_3)_3$. In another embodiment of formula IIIA or formula IIIB, $R^{YZ}$ is —$CH_3$, —$CH_2CH_3$, —$CH(CH_3)_2$, —$CH_2CH_2CH_3$, —CH$_2$CH$_2$OCH$_3$, —CH$_2$CH(CH$_3$)$_2$, or —CH$_2$C(CH$_3$)$_3$. In another embodiment of formula IIIB, R$^{YZ}$ is —CH(CH$_3$)$_2$ or —CH$_2$CH$_2$OCH$_3$.

In one embodiment of formula IIIA:
R$^3$ is C$_1$-C$_4$ alkyl;
R$^5$ is hydrogen; and
R$^{YZ}$ is —CH$_3$, —CH$_2$CH$_3$, —CH(CH$_3$)$_2$, —CH$_2$CH$_2$CH$_3$, —CH$_2$CH(CH$_3$)$_2$, or —CH$_2$C(CH$_3$)$_3$.

In another embodiment of formula IIIA:
R$^3$ is C$_1$-C$_4$ alkyl;
R$^5$ is fluoro; and
R$^{YZ}$ is —CH$_3$, —CH$_2$CH$_3$, —CH(CH$_3$)$_2$, —CH$_2$CH$_2$CH$_3$, —CH$_2$CH(CH$_3$)$_2$, or —CH$_2$C(CH$_3$)$_3$.

In one embodiment of formula IIIA:
R$^3$ is —CH$_3$;
R$^5$ is hydrogen; and
R$^{YZ}$ is —CH$_3$, —CH$_2$CH$_3$, —CH(CH$_3$)$_2$, —CH$_2$CH$_2$CH$_3$, —CH$_2$CH(CH$_3$)$_2$, or —CH$_2$C(CH$_3$)$_3$.

In one embodiment of formula IIIA:
R$^3$ is —CH$_3$;
R$^5$ is fluoro; and
R$^{YZ}$ is —CH$_3$, —CH$_2$CH$_3$, —CH(CH$_3$)$_2$, —CH$_2$CH$_2$CH$_3$, —CH$_2$CH(CH$_3$)$_2$, or —CH$_2$C(CH$_3$)$_3$.

In one embodiment of formula IIIB:
R$^3$ is C$_1$-C$_4$ alkyl;
R$^5$ is hydrogen; and
R$^{YZ}$ is —CH$_3$, —CH$_2$CH$_3$, —CH(CH$_3$)$_2$, —CH$_2$CH$_2$CH$_3$, —CH$_2$CH(CH$_3$)$_2$, or —CH$_2$C(CH$_3$)$_3$.

In another embodiment of formula IIIB:
R$^3$ is C$_1$-C$_4$ alkyl;
R$^5$ is fluoro; and
R$^{YZ}$ is —CH$_3$, —CH$_2$CH$_3$, —CH(CH$_3$)$_2$, —CH$_2$CH$_2$CH$_3$, —CH$_2$CH(CH$_3$)$_2$, or —CH$_2$C(CH$_3$)$_3$.

In one embodiment of formula IIIB:
R$^3$ is —CH$_3$;
R$^5$ is hydrogen; and
R$^{YZ}$ is —CH$_3$, —CH$_2$CH$_3$, —CH(CH$_3$)$_2$, —CH$_2$CH$_2$CH$_3$, —CH$_2$CH(CH$_3$)$_2$, or —CH$_2$C(CH$_3$)$_3$.

In one embodiment of formula IIIB:
R$^3$ is —CH$_3$;
R$^5$ is fluoro; and
R$^{YZ}$ is —CH$_3$, —CH$_2$CH$_3$, —CH(CH$_3$)$_2$, —CH$_2$CH$_2$CH$_3$, —CH$_2$CH(CH$_3$)$_2$, or —CH$_2$C(CH$_3$)$_3$.

In another embodiment, the present invention provides a compound of formula IIIA-1 or formula IIIB-1:

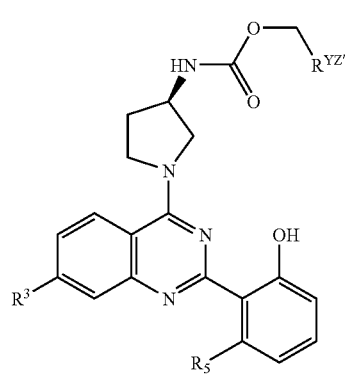

IIIA-1

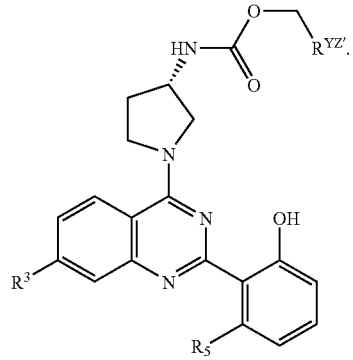

IIIB-1

In one embodiment of formula IIIA-1 or formula IIIB-1, R$^3$ is C$_1$-C$_4$ alkyl. In another embodiment, R$^3$ is methyl, ethyl, propyl, or butyl.

In another embodiment of formula IIIA-1 or formula IIIB-1, R$^5$ is hydrogen or halo. In one embodiment, R$^5$ is hydrogen. In another embodiment, R$^5$ is halo.

In one embodiment of formula IIIA-1 or formula IIIB-1, R$^{YZ'}$ is —CH$_3$, —CH$_2$CH$_3$, —CH(CH$_3$)$_2$, —C(CH$_3$)$_3$, or —CH$_2$OCH$_3$.

In one embodiment of formula IIIA-1:
R$^3$ is C$_1$-C$_4$ alkyl;
R$^5$ is hydrogen or fluoro; and
R$^{YZ'}$ is —CH$_3$, —CH$_2$CH$_3$, —CH(CH$_3$)$_2$, —C(CH$_3$)$_3$, or —CH$_2$OCH$_3$.

In one embodiment of formula IIIA-1:
R$^3$ is C$_1$-C$_4$ alkyl;
R$^5$ is hydrogen; and
R$^{YZ'}$ is —CH$_3$, —CH$_2$CH$_3$, —CH(CH$_3$)$_2$, —C(CH$_3$)$_3$, or —CH$_2$OCH$_3$.

In another embodiment of formula IIIA-1:
R$^3$ is C$_1$-C$_4$ alkyl;
R$^5$ is fluoro; and
R$^{YZ'}$ is —CH$_3$, —CH$_2$CH$_3$, —CH(CH$_3$)$_2$, —C(CH$_3$)$_3$, or —CH$_2$OCH$_3$.

In one embodiment of formula IIIA-1:
R$^3$ is —CH$_3$;
R$^5$ is hydrogen; and
R$^{YZ'}$ is —CH$_3$, —CH$_2$CH$_3$, —CH(CH$_3$)$_2$, —C(CH$_3$)$_3$, or —CH$_2$OCH$_3$.

In one embodiment of formula IIIB-1:
R$^3$ is C$_1$-C$_4$ alkyl;
R$^5$ is hydrogen or fluoro; and
R$^{YZ'}$ is —CH$_3$, —CH$_2$CH$_3$, —CH(CH$_3$)$_2$, —C(CH$_3$)$_3$, or —CH$_2$OCH$_3$.

In one embodiment of formula IIIB-1:
R$^3$ is C$_1$-C$_4$ alkyl;
R$^5$ is hydrogen; and
R$^{YZ'}$ is —CH$_3$, —CH$_2$CH$_3$, —CH(CH$_3$)$_2$, —C(CH$_3$)$_3$, or —CH$_2$OCH$_3$.

In another embodiment of formula IIIB-1:
R$^3$ is C$_1$-C$_4$ alkyl;
R$^5$ is fluoro; and
R$^{YZ'}$ is —CH$_3$, —CH$_2$CH$_3$, —CH(CH$_3$)$_2$, —C(CH$_3$)$_3$, or —CH$_2$OCH$_3$.

In one embodiment of formula IIIB-1:
R$^3$ is —CH$_3$;
R$^5$ is hydrogen; and
R$^{YZ'}$ is —CH$_3$, —CH$_2$CH$_3$, —CH(CH$_3$)$_2$, —C(CH$_3$)$_3$, or —CH$_2$OCH$_3$.

In one embodiment of formula IIIB-1:
$R^3$ is —CH$_3$;
$R^5$ is hydrogen; and
$R^{YZ'}$ is —CH(CH$_3$)$_2$ or —CH$_2$OCH$_3$.
In one embodiment, the present invention provides compounds shown below in Table 2.
TABLE 2
1
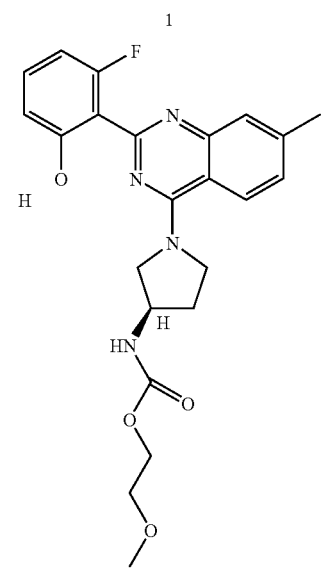
2
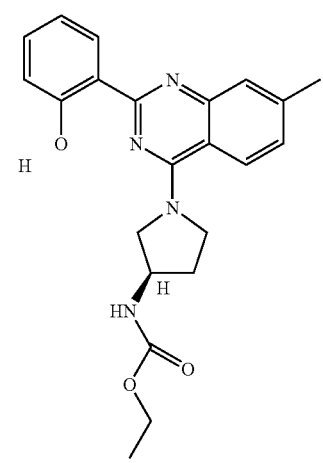
TABLE 2-continued
3
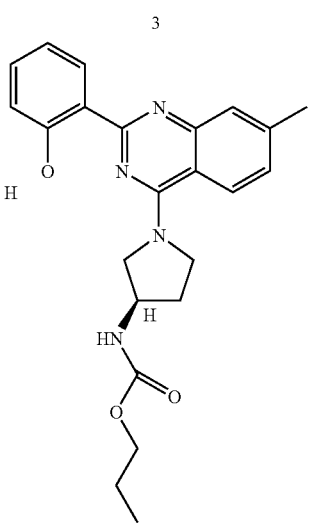
4
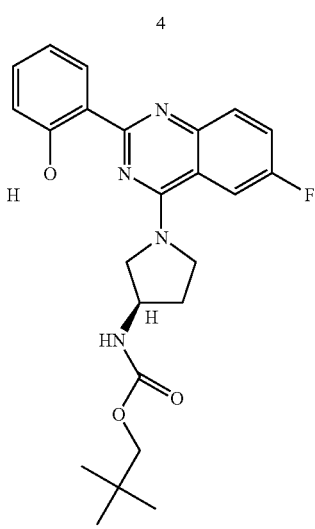
5
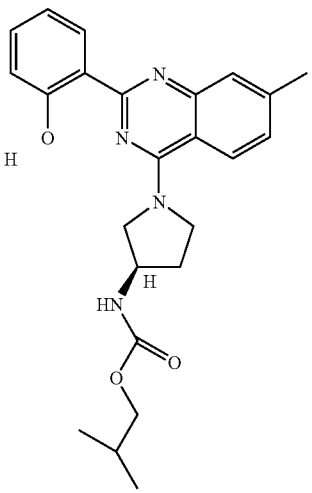

TABLE 2-continued
6
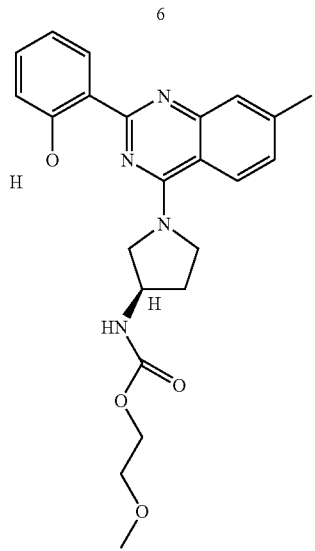
7
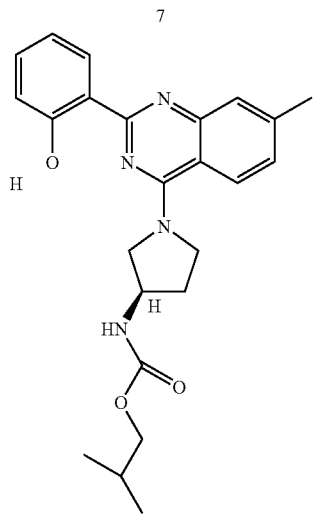
8
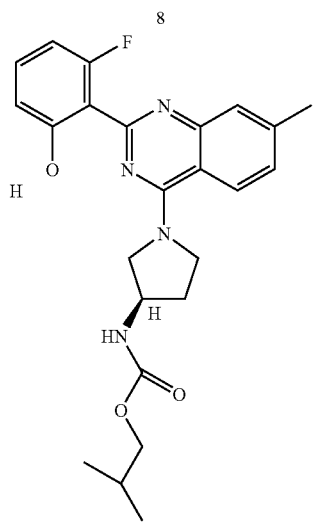
TABLE 2-continued
9
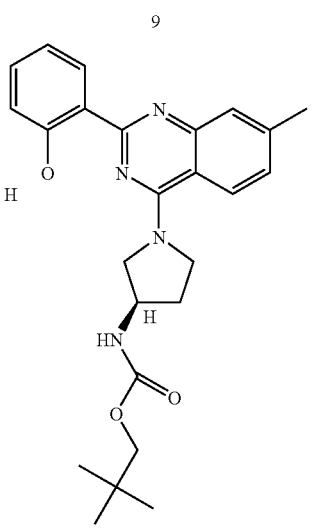
10
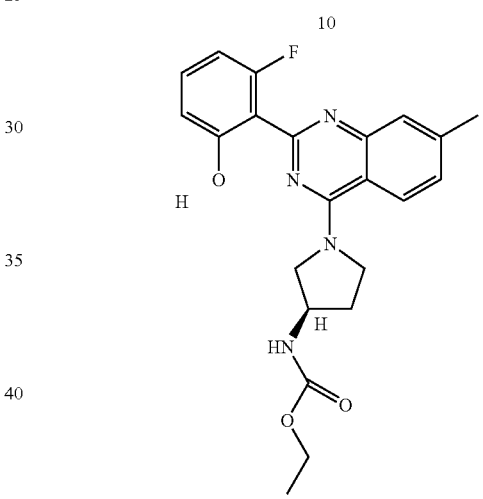
11
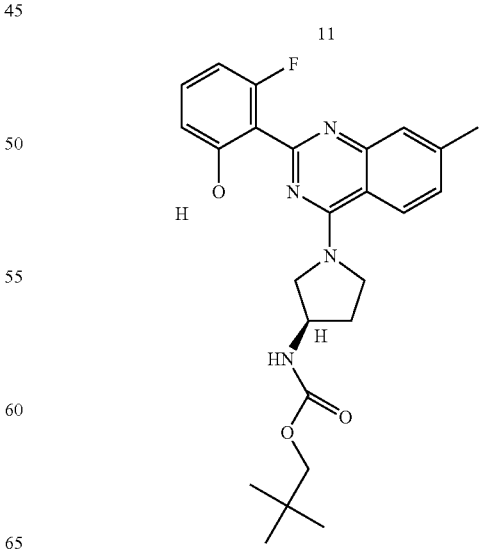

TABLE 2-continued
12
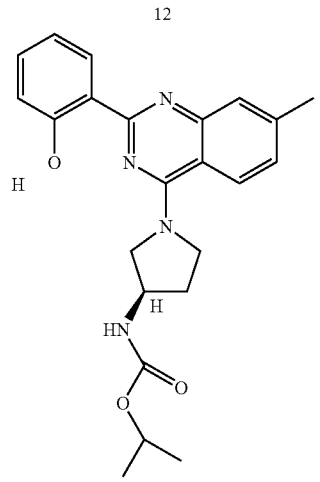
13
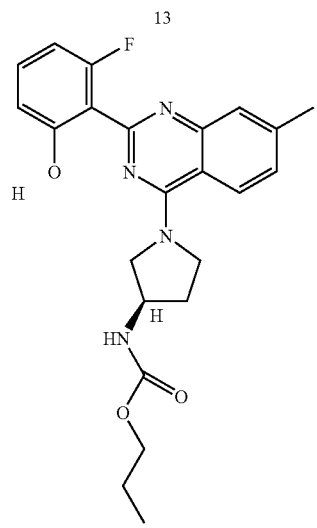
14
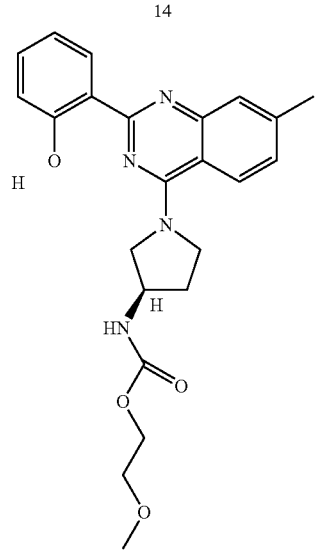
TABLE 2-continued
15
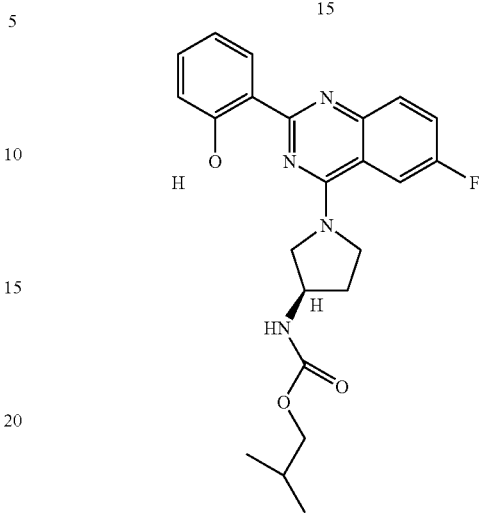
16
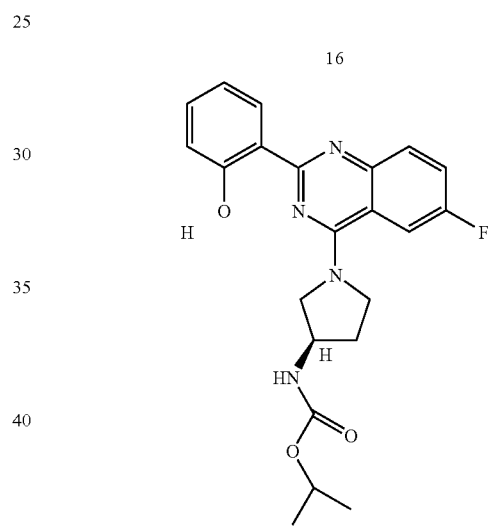
17
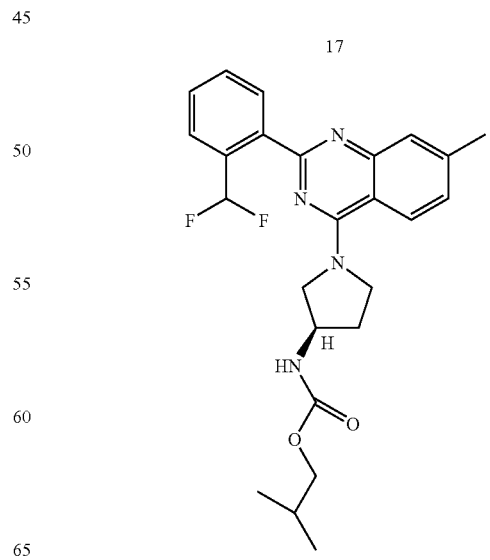

TABLE 2-continued
18
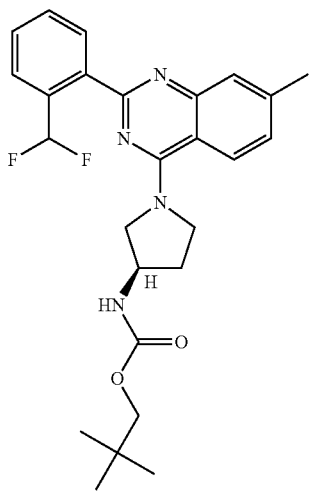
4. General Synthetic Methodology:
The compounds of this invention may be prepared in general by methods known to those skilled in the art for analogous compounds, as illustrated by the general schemes below, and the preparative examples that follow.
Scheme A: General Preparation of Compounds of Formula IA via 4-Chloroquinazolines
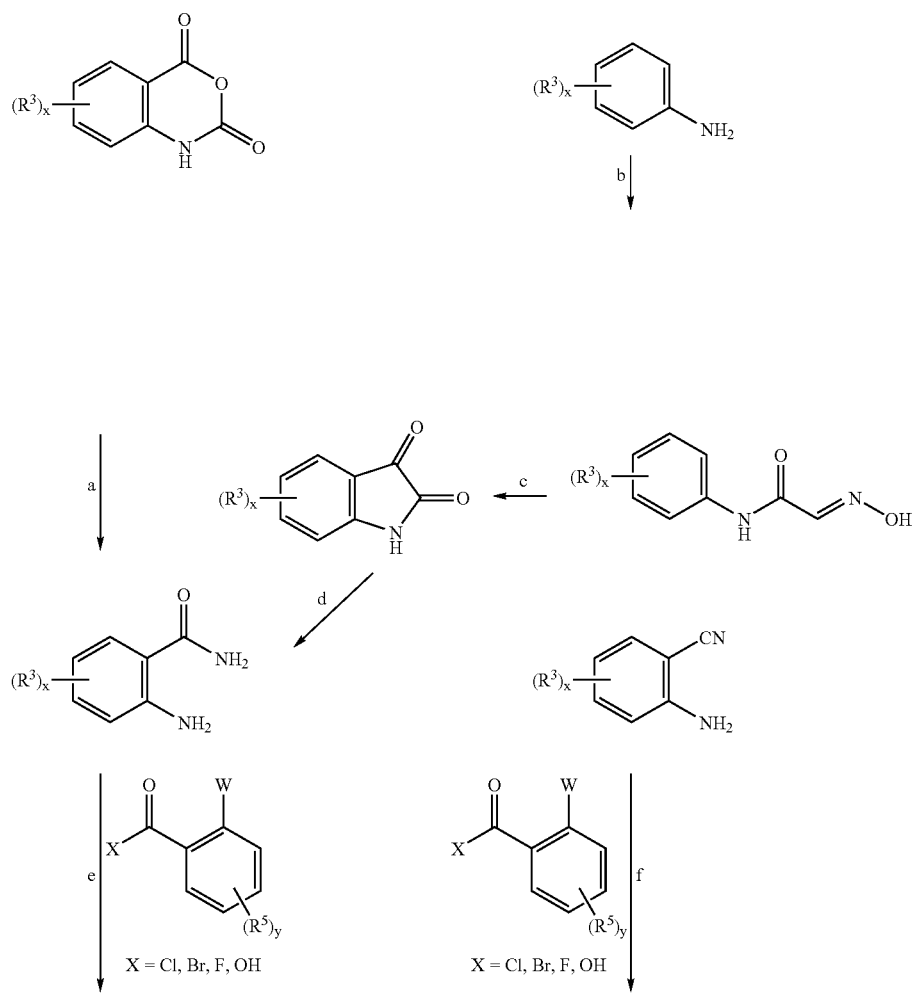

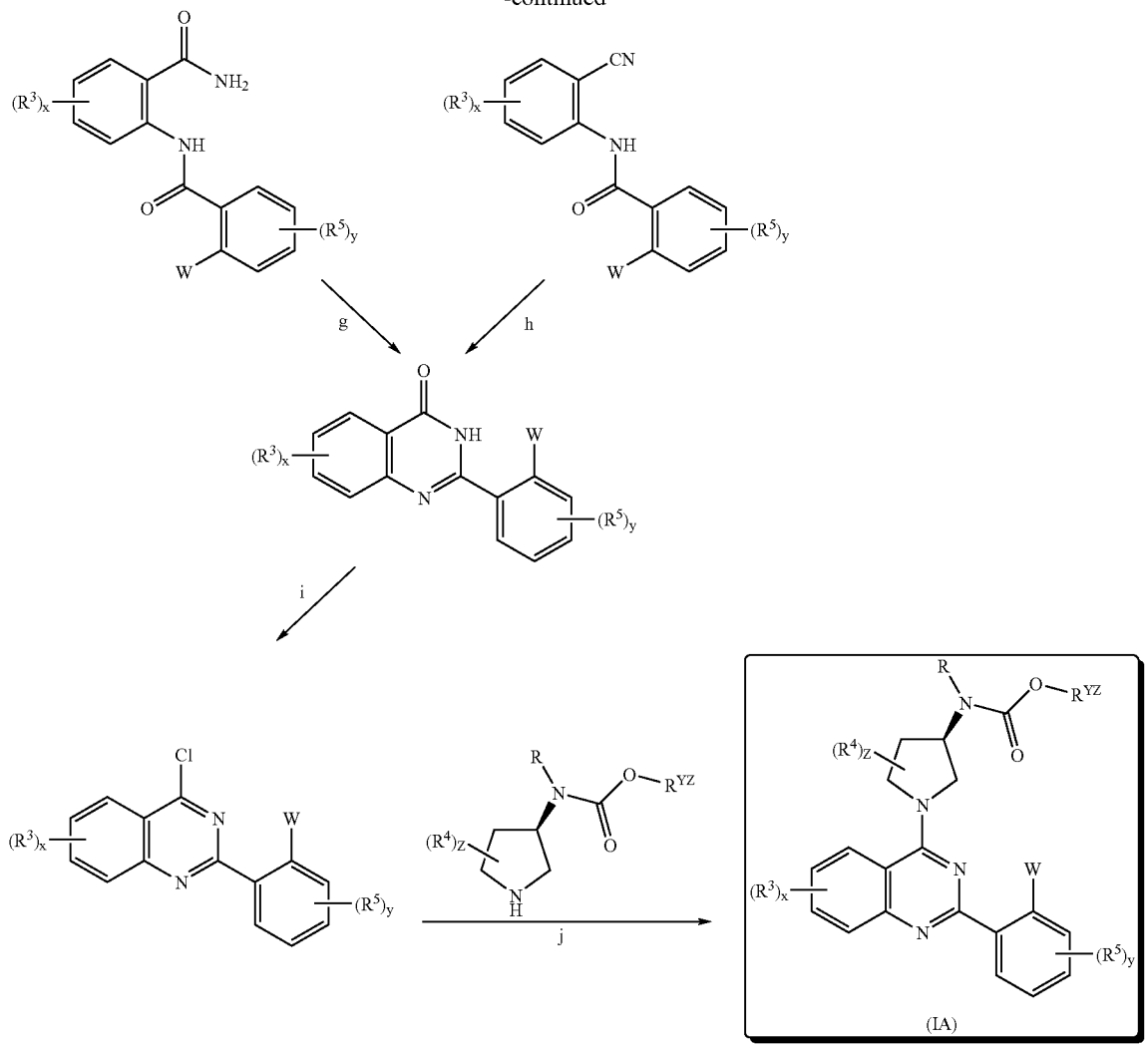

Conditions: a) aq. NH$_4$OH; b) chloral hydrate, HCl, Na$_2$SO$_4$, HONH$_2$*HCl c) H$_2$SO$_4$; d) acetic acid, H$_2$SO$_4$, aq. H$_2$O$_2$; e) For acid halides when X=Cl, Br, or F, then DCM or THF, triethylamine; for carboxylic acids when X=OH, EDC, HOBt, triethylamine, DMF; f) For acid halides when X=Cl, Br, or F, then Et$_3$N, DMAP, CH$_2$Cl$_2$; for carboxylic acids when X=OH, EDC, HOBt, triethylamine, DMF; g) aq. NaOH; h) aq. NaOH, aq. H$_2$O$_2$; i) POCl$_3$, N,N-dimethylaniline, benzene; j) Et$_3$N, CH$_2$Cl$_2$.

Scheme B: Additional Preparations of Compounds of Formula IA via 4-Chloroquinazolines

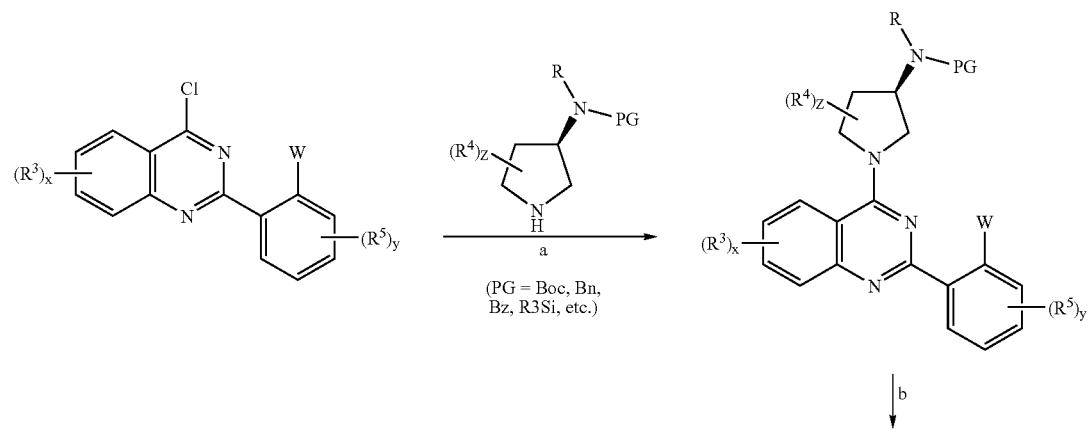

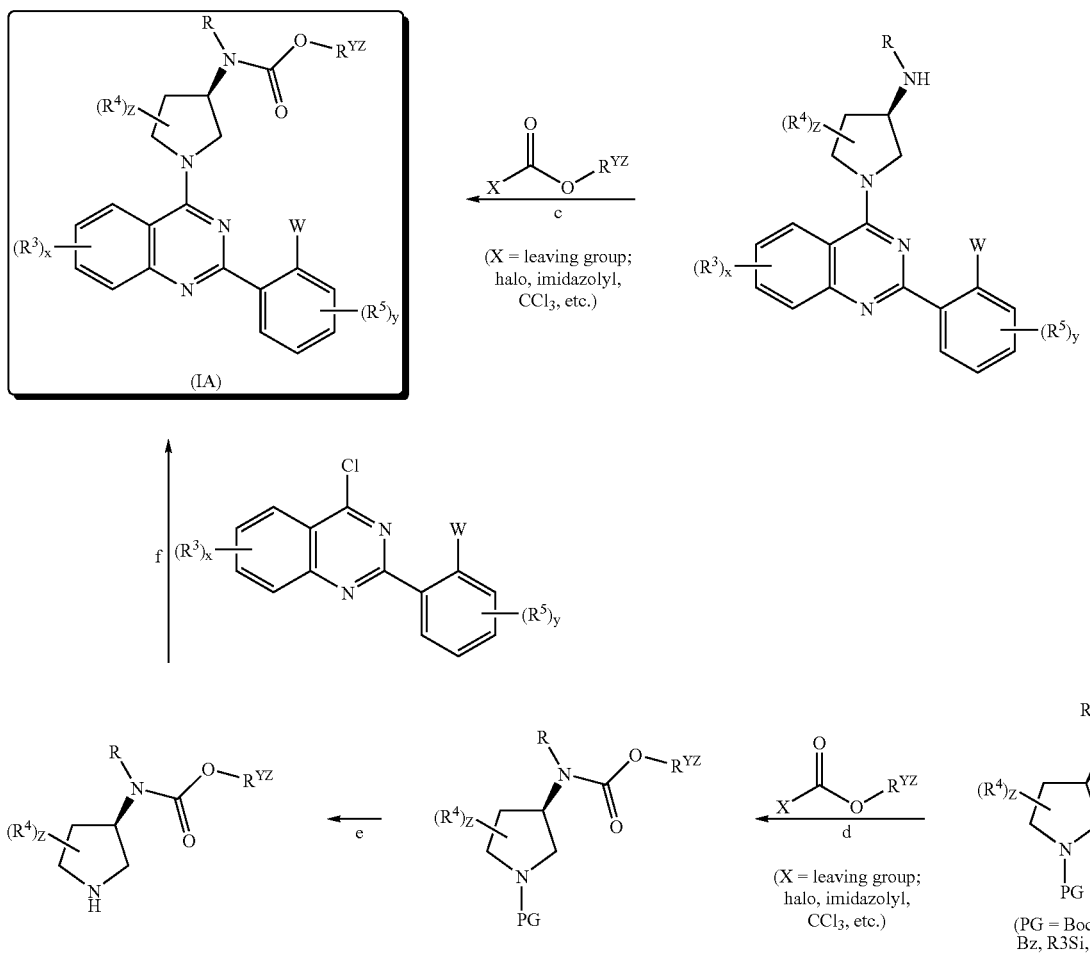

Conditions: a) DCM or THF, triethylamine, 0° C. to room temperature; b) Deprotect: 1:1 TFA/DCM, rt, for Boc; H₂, Pd/C for Bn; NaOH for Bz, TBAF for R3Si, etc.; c) DCM or THF, triethylamine; d) DCM or THF, triethylamine; e) Deprotect: 1:1 TFA/DCM, rt, for Boc; H₂, Pd/C for Bn; NaOH for Bz, TBAF for R3Si, etc.; f) DCM or THF, triethylamine, 0° C. to room temperature.

Scheme C: General Preparation of Compounds of Formula IA via 2,4-Dichloroquinazolines

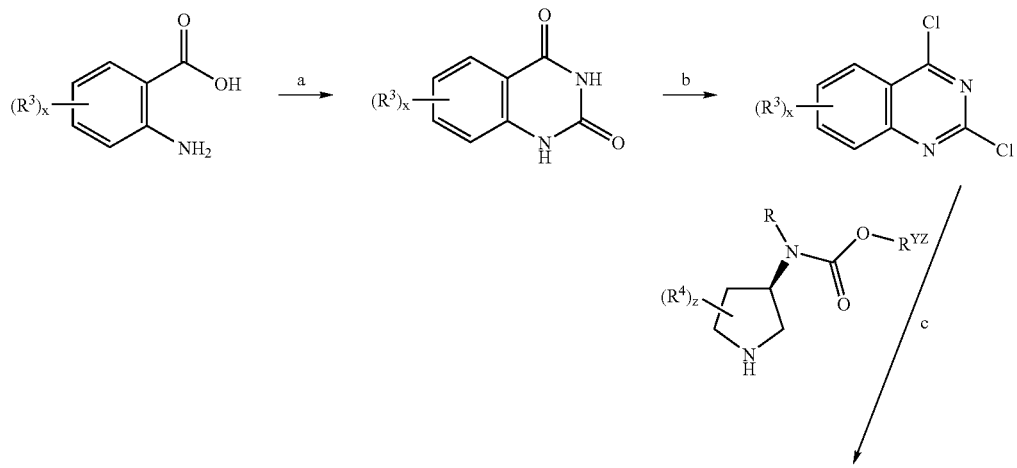

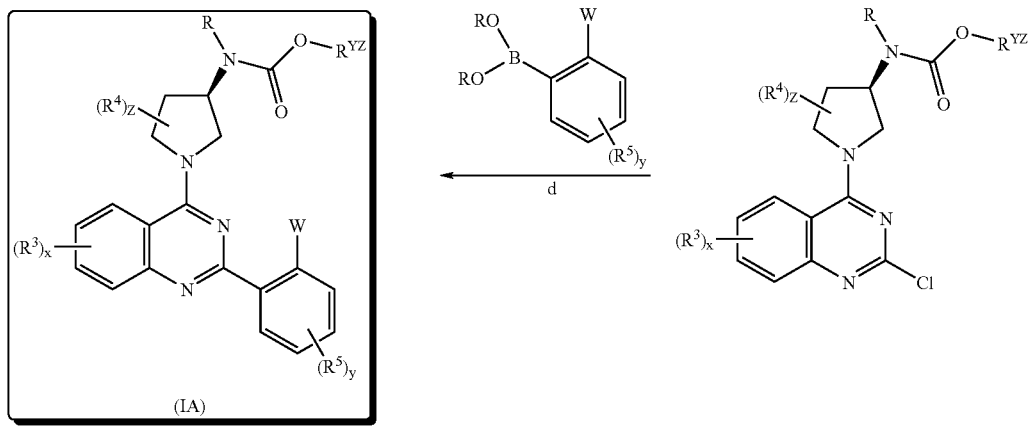
Conditions: a) AcOH, KOCN; b) POCl₃; c) Et₃N, DCM; d) Pd(PPh₃)₄, K₂CO₃, CH₃CN, H₂O.
Scheme D: General Preparation of Compounds of Formula IB via 4-Chloroquinazolines
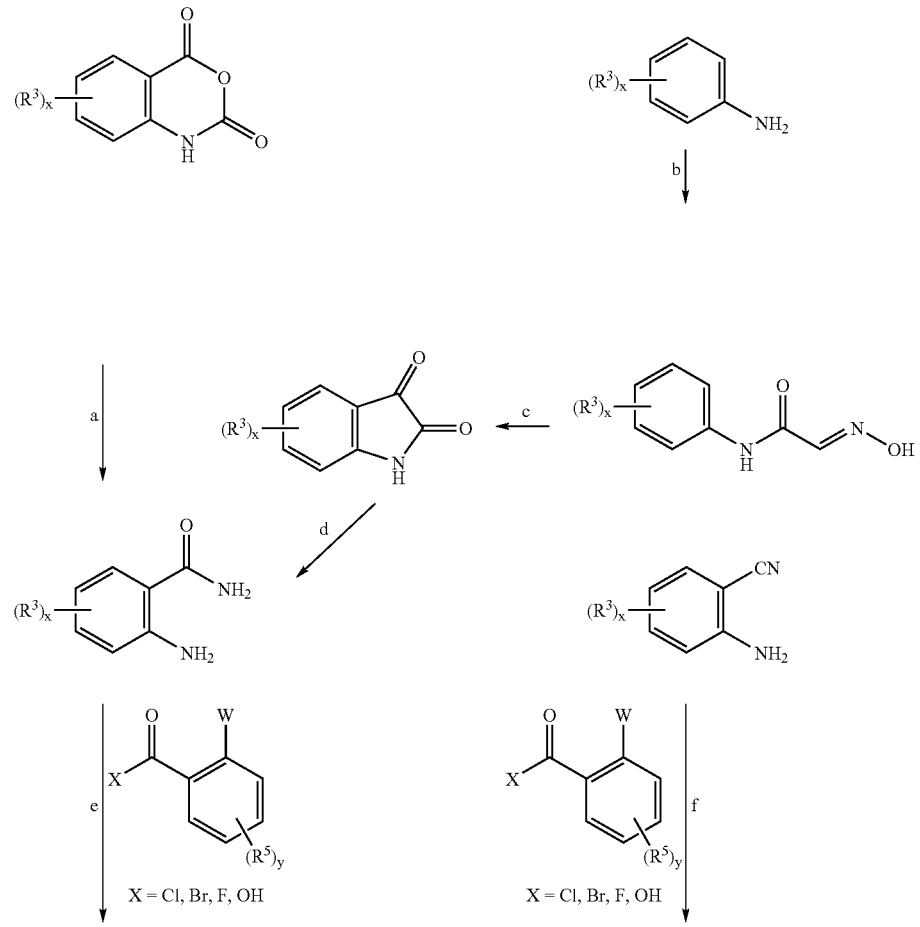

-continued

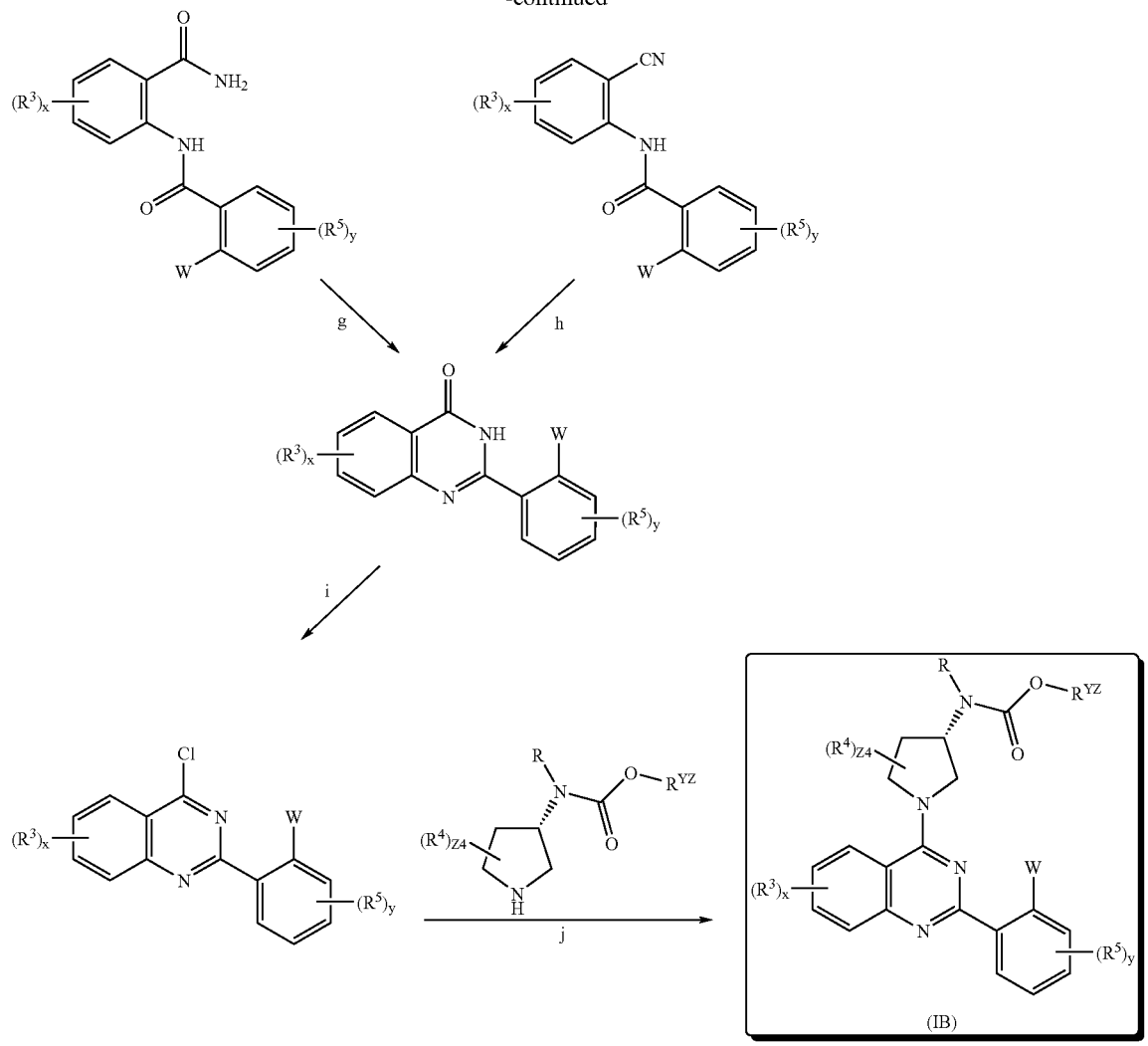

Conditions: a) aq. NH$_4$OH; b) chloral hydrate, HCl, Na$_2$SO$_4$, HONH$_2$*HCl c) H$_2$SO$_4$; d) acetic acid, H$_2$SO$_4$, aq. H$_2$O$_2$; e) For acid halides when X=Cl, Br, or F, then DCM or THF, triethylamine; for carboxylic acids when X=OH, EDC, HOBt, triethylamine, DMF; f) For acid halides when X=Cl, Br, or F, then Et$_3$N, DMAP, CH$_2$Cl$_2$; for carboxylic acids when X=OH, EDC, HOBt, triethylamine, DMF; g) aq. NaOH; h) aq. NaOH, aq. H$_2$O$_2$; i) POCl$_3$, N,N-dimethylaniline, benzene; j) Et$_3$N, CH$_2$Cl$_2$.

Scheme E: Additional Preparations of Compounds of Formula IB via 4-Chloroquinazolines

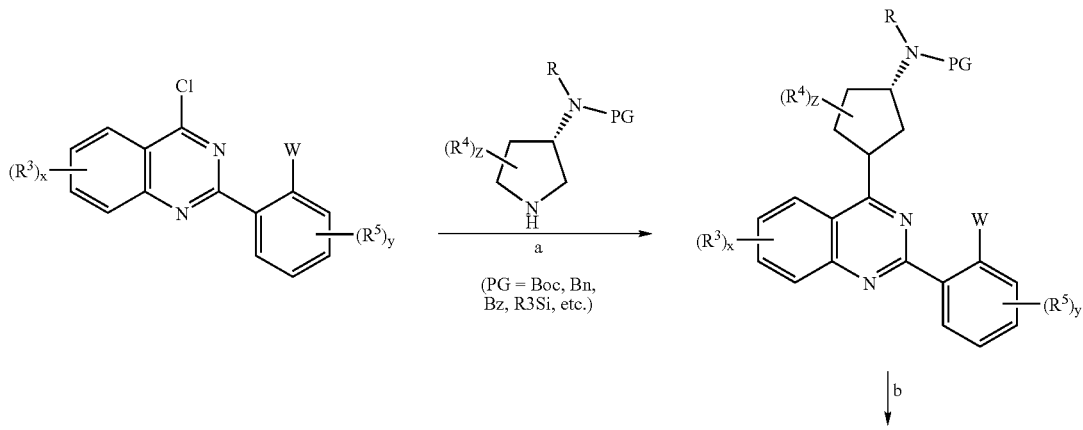

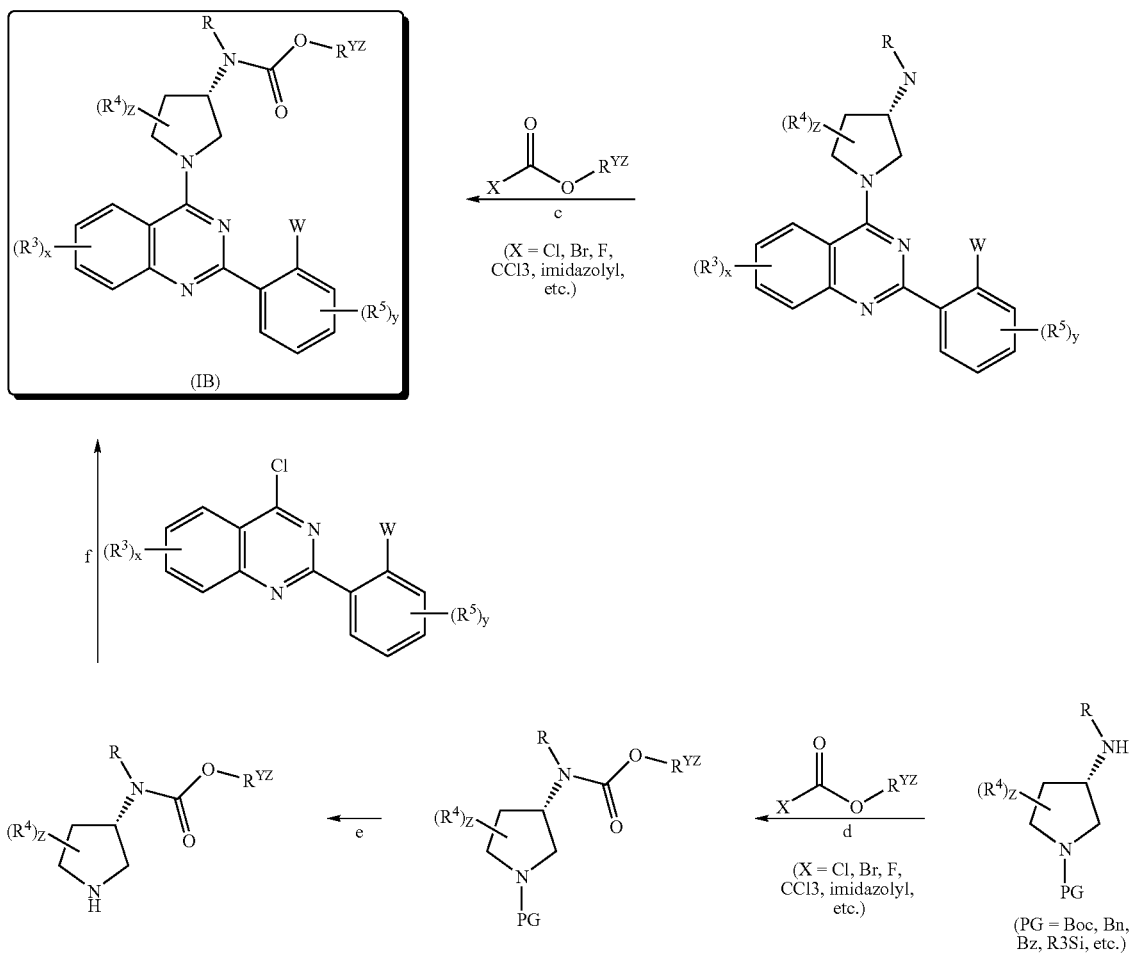

Conditions: a) DCM or THF, triethylamine, 0° C. to room temperature; b) Deprotect: 1:1 TFA/DCM, rt, for Boc; H₂, Pd/C for Bn; NaOH for Bz, TBAF for R3Si, etc.; c) DCM or THF, triethylamine; d) DCM or THF, triethylamine, rt or heat;

e) Deprotect: 1:1 TFA/DCM, rt, for Boc; H₂, Pd/C for Bn; NaOH for Bz, TBAF for R3Si, etc.; f) DCM or THF, triethylamine, 0° C. to room temperature.

Scheme F: General Preparation of Compounds of Formula IB via 2,4-Dichloroquinazolines

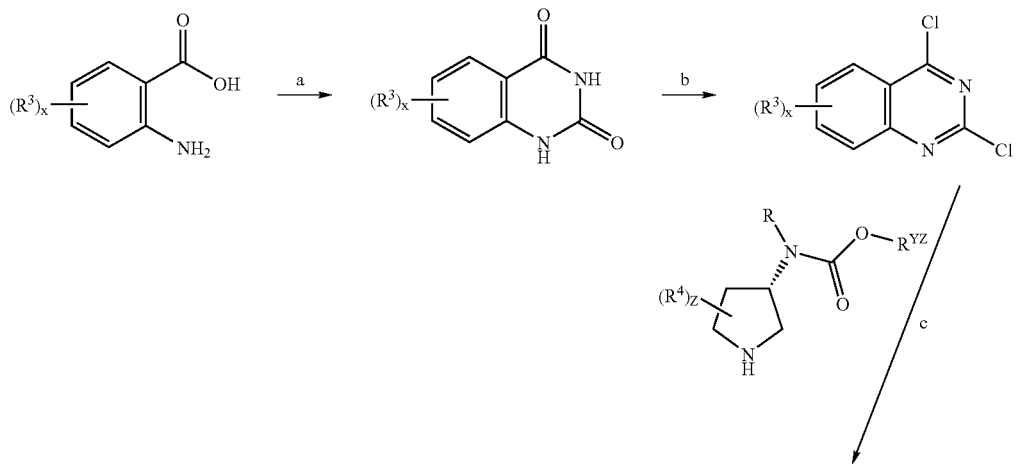

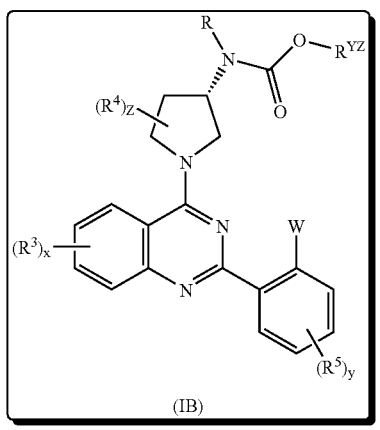

(IB)

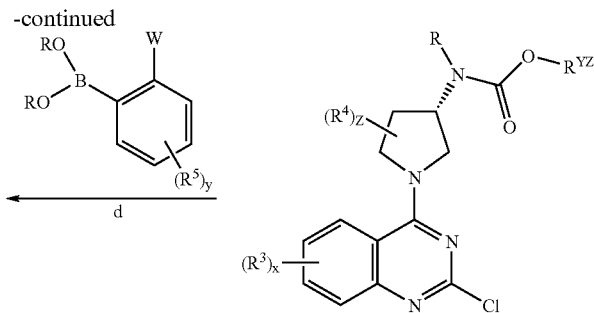

Conditions: a) AcOH, KOCN; b) POCl$_3$; c) Et$_3$N, DCM; d) Pd(PPh$_3$)$_4$, K$_2$CO$_3$, CH$_3$CN, H$_2$O.

Schemes A though C above are also useful for the preparation of compounds of formula IIA, IIA-1, IIIA, and IIIA-1. Schemes D through F are also useful for the preparation of compounds of formula IIB, IIB-1, IIIB, and IIIB-1.

5. Uses of Compounds, Pharmaceutically Acceptable Compositions, Formulation and Administration WO 2004/078733 discloses a genus of sodium channel blockers that encompasses the compounds of the present invention. However, the compounds of the present invention exhibit unexpected properties set forth below that render them therapeutically more useful.

In one embodiment, certain compounds of the present invention are useful as improved inhibitors of sodium channels.

In another embodiment, certain compounds of the present invention possess improved selectivity in inhibiting one sodium channel, e.g., NaV 1.8, over one or more of the other sodium channels. Particularly useful are compounds that have a desirably low activity against NaV 1.2 or NaV 1.5.

In another embodiment, certain compounds of the present invention are improved inhibitors of NaV 1.8.

In another embodiment, certain compounds of the present invention have improved aqueous solubility, e.g., at physiologically relevant pH.

In yet another embodiment, certain compounds of the present invention have improved pharmacokinetic and/or pharmacodynamic properties and, therefore, are better suited for in-vivo administration for therapeutic purposes. Such properties include oral bioavailability, clearance kinetics, efficacy, etc.

In another embodiment, certain compounds of the present invention have desirably low activity against the hERG channel.

In another embodiment, certain compounds of the present invention have desirably low activity against the key isoforms of the cytochrome P450 enzyme family, including isozymes CYP3A4, CYP2C9, CYP1A2, CYP2C19, or CYP2D6.

In another embodiment, certain compounds of the present invention have desirably low activity against the CaV 1.2 channel and/or Kv 1.5.

Thus, in one embodiment of the present invention, the compounds have one or more of the following unexpected and therapeutically beneficial features: potent inhibition of NaV 1.8 channel, selectivity for one sodium channel, e.g., NaV 1.8 over one or more of the other sodium channels, improved aqueous solubility, improved pharmacokinetic and/or pharmacodynamic properties, desirably low activity against the hERG channel, desirably low activity against the key isoforms of the cytochrome P450 enzyme family, or desirably low activity against L-type CaV 1.2 and/or Kv1.5. The presence of such features, individually or in combination, renders the compounds more suitable for administration to humans to treat one or more of the various diseases set forth below.

The phrase "desirably low activity" as used herein means a level of activity of a compound against a target/enzyme that is low enough such that said activity would be considered advantageous (e.g., mitigating a risk factor), when evaluating the suitability of said compound for administration in humans.

The present compounds are useful for the treatment of diseases, disorders, and conditions including, but not limited to acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, and incontinence. Accordingly, in another aspect of the present invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

According to one embodiment, the compounds of the present invention are useful for treating a disease selected from femur cancer pain; non-malignant chronic bone pain; rheumatoid arthritis; osteoarthritis; spinal stenosis; neuropathic low back pain; neuropathic low back pain; myofascial pain syndrome; fibromyalgia; temporomandibular joint pain; chronic visceral pain, including, abdominal; pancreatic; IBS pain; chronic headache pain; migraine; tension headache, including, cluster headaches; chronic neuropathic pain, including, post-herpetic neuralgia; diabetic neuropathy; HIV-associated neuropathy; trigeminal neuralgia; Charcot-Marie Tooth neuropathy; hereditary sensory neuropathies; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury/exercise pain; acute visceral pain, including, abdominal pain; pyelonephritis; appendicitis; cholecystitis; intestinal obstruction; hernias; etc; chest pain, including, cardiac pain; pelvic pain, renal colic pain, acute obstetric pain, including, labor pain; cesarean section pain; acute inflammatory, burn and trauma pain; acute intermittent pain, including, endometriosis; acute herpes zoster pain; sickle cell anemia; acute pancreatitis; breakthrough pain; orofacial pain, including, sinusitis pain, dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease, including, urinary incontinence; hyperactivity bladder; painful bladder syndrome; interstitial cystitis (IC); and prostatitis.

In another embodiment, the compounds of the present invention are useful in treating lower urinary tract disorders. See, e.g., International Patent Publication No. WO 2004/066990, the contents of which are incorporated herein by reference.

It will also be appreciated that certain of the compounds of present invention can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or any other adduct or derivative which upon administration to a patient in need is capable of providing, directly or indirectly, a compound as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. A "pharmaceutically acceptable salt" means any non-toxic salt or salt of an ester of a compound of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of the targeted channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In yet another aspect, a method for the treatment or lessening the severity of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain is provided comprising administering an effective amount of a compound, or a pharmaceutically acceptable composition comprising a compound to a subject in need thereof. In certain embodiments, a method for the treatment or lessening the severity of acute, chronic, neuropathic, or inflammatory pain is provided comprising administering an effective amount of a compound or a pharmaceutically acceptable composition to a subject in need thereof. In certain other embodiments, a method for the treatment or lessening the severity of radicular pain, sciatica, back pain, head pain, or neck pain is provided comprising administering an effective amount of a compound or a pharmaceutically acceptable composition to a subject in need thereof. In still other embodiments, a method for the treatment or lessening the severity of severe or intractable pain, acute pain, postsurgical pain, back pain, or cancer pain is provided comprising administering an effective amount of a compound or a pharmaceutically acceptable composition to a subject in need thereof.

In certain embodiments of the present invention an "effective amount" of the compound or pharmaceutically acceptable composition is that amount effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain.

The compounds and compositions, according to the method of the present invention, may be administered using any amount and any route of administration effective for treating or lessening the severity of one or more of acute, chronic, neuropathic, or inflammatory pain, arthritis, migraine, cluster headaches, trigeminal neuralgia, herpetic neuralgia, general neuralgias, epilepsy or epilepsy conditions, neurodegenerative disorders, psychiatric disorders such as anxiety and depression, myotonia, arrhythmia, movement disorders, neuroendocrine disorders, ataxia, multiple sclerosis, irritable bowel syndrome, incontinence, visceral pain, osteoarthritis pain, postherpetic neuralgia, diabetic neuropathy, radicular pain, sciatica, back pain, head or neck pain, severe or intractable pain, nociceptive pain, breakthrough pain, postsurgical pain, or cancer pain. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

It will also be appreciated that the compounds and pharmaceutically acceptable compositions of the present invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated". For example, exemplary additional therapeutic agents include, but are not limited to: nonopioid analgesics (indoles such as Etodolac, Indomethacin, Sulindac, Tolmetin; naphthylalkanones such as Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Aspirin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Seventeenth Edition, Ed. Mark H. Beers and Robert Berkow, Merck Research Laboratories, 1999, The Merck Manual, Eighteenth Edition, Ed. Mark H. Beers and Robert Porter, Merck Research Laboratories, 2006, The Merck Manual, and the Food and Drug Administration website, www.fda.gov, the entire contents of which are hereby incorporated by reference.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the present invention, in another aspect, includes a composition for coating an implantable device comprising a compound of the present invention as described generally above, and in classes and subclasses herein, and a carrier suitable for coating said implantable device. In still another aspect, the present invention includes an implantable device coated with a composition comprising a compound of the present invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting NaV1.8 activity in a biological sample or a patient, which method comprises administering to the patient, or contacting said biological sample with a compound of the present invention or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of NaV1.8 activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

In order that the invention described herein may be more fully understood, the following examples are set forth. It should be understood that these examples are for illustrative purposes only and are not to be construed as limiting this invention in any manner.

EXAMPLES

Reagents, solvents, etc. and their abbreviations that may be useful for the preparation of compounds of formula IA, IB, IIA, IIB, IIIA, and IIIB using general methods known to those skilled in the art include but are not limited to the following:

THF: tetrahydrofuran

DMF: N,N-dimethylformamide

EtOAc: ethyl acetate

DCM or $CH_2Cl_2$: methylene chloride

DMSO: dimethyl sulfoxide $CH_3CN$: acetonitrile $Et_3N$: triethylamine

DIPEA: diisopropylethylamine

TFA: trifluoroacetic acid

HOBt: 1-hydroxybenzotriazole hydrate

EDC: 1-(3-dimethylaminopropyl)-3-ethylcarbodiimide hydrochloride

4-DMAP: 4-dimethylaminopyridine $K_2CO_3$: potassium carbonate $Na_2CO_3$: sodium carbonate $Li_2CO_3$: lithium carbonate $Cs_2CO_3$: cesium carbonate $NaHCO_3$: sodium bicarbonate NaOH: sodium hydroxide KOH: potassium hydroxide LiOH: lithium hydroxide General LC/MS Methods LC/MS data were acquired using a PESciex API-150-EX LC/MS, Shimadzu LC-8A pumps, Gilson 215 autosampler, Gilson 819 injection module, 3.0 mL/min flow rate, 10-99% $CH_3CN$ (0.035% TFA)/$H_2O$ (0.05% TFA) gradient, Phenomenex Luna 5u C18 column (50×4.60 mm), Shimadzu SPD-10A UV/Vis detector, Cedex 75 ELSD detector.

Example 1

(R)-2-Methoxyethyl 1-(2-(2-fluoro-6-hydroxyphenyl)-7-methylquinazolin-4-yl)pyrrolidin-3-ylcarbamate (compound 1)

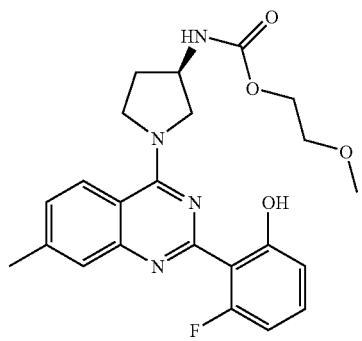

N-(2-Cyano-5-methyl-phenyl)-2-fluoro-6-methoxy-benzamide

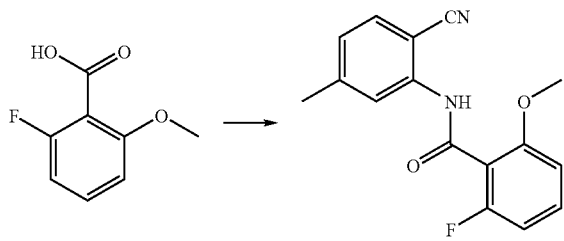

6-Fluoro-2-anisoic acid (110 g, 0.70 mol) was added in portions over 15 minutes to a mixture of thionyl chloride (230 ml, 3.2 mol), toluene (200 mL), and DMF (1 mL). The resulting mixture was stirred overnight at room temperature. The solution was evaporated to dryness and added dropwise to an ice-bath cooled solution of 2-amino-4-methylbenzonitrile (92.5 g, 0.70 mol) in pyridine (200 mL). The dropping funnel was rinsed with a minimal amount of acetonitrile. The resulting mixture was stirred overnight at room temperature under a nitrogen atmosphere and was subsequently poured into 2 L ice water. The resulting slurry was stirred vigorously for 1 hour. The formed solid was collected by filtration and was washed twice with water. The filter cake was dissolved in 2 L dichloromethane, and this solution was washed with 1 N aq. HCl (400 mL) and with saturated aq. NaCl (400 mL), dried over sodium sulfate, filtered, and evaporated to dryness to give N-(2-cyano-5-methylphenyl)-2-fluoro-6-methoxybenzamide (186 g, 93%) as a brownish solid. $^1$H-NMR (CDCl$_3$, 200 MHz): δ9.09 (s, 1H), 8.58 (s, 1H), 7.59-7.42 (m, 2H), 7.09-7.02 (m, 1H), 6.94-6.83 (m, 2H), 4.11 (s, 3H), 2.57 (s, 3H) ppm.

2-(2-Fluoro-6-methoxy-phenyl)-7-methyl-3H-quinazolin-4-one

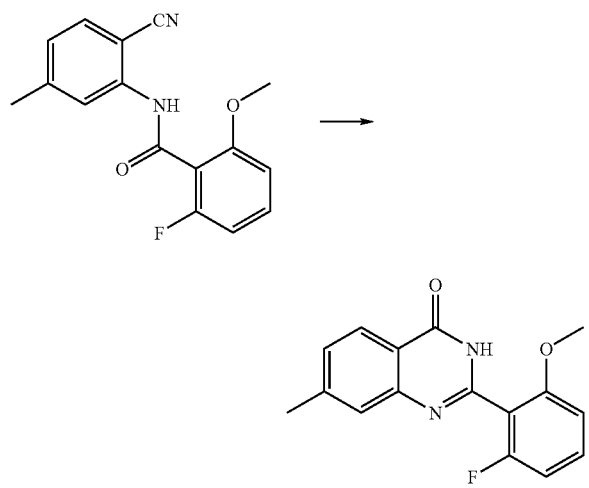

To a suspension of N-(2-cyano-5-methylphenyl)-2-fluoro-6-methoxybenzamide (31.5 g, 111 mmol) in ethanol (626 mL) was added 6 M aqueous NaOH solution (205 mL). After 10 minutes, 30% aqueous H$_2$O$_2$ (60 mL) was added, forming a slurry. The reaction was heated to reflux for 18 h and cooled to room temperature. NaOH (22.2 g, 0.56 mol) and 30% aqueous H$_2$O$_2$ (26 mL) were added, and the reaction was heated to reflux for six hours. The reaction cooled to room temperature, 30% aqueous H$_2$O$_2$ (45 mL) was added, and the reaction was heated to reflux for 18 h. The reaction was cooled to room temperature, NaOH (10 g, 0.25 mol) and 30% aqueous H$_2$O$_2$ (70 mL) were added, and the reaction was heated to reflux for six hours. The reaction was cooled to room temperature and poured over ice (800 mL). The pH was adjusted to 3-4 by addition of conc. HCl solution, and the precipitated off-white solid was filtered and washed with water (3×40 mL). The solid was dried under vacuum to provide 2-(2-fluoro-6-methoxy-phenyl)-7-methyl-3H-quinazolin-4-one (28 g, 89%).

4-Chloro-2-(2-fluoro-6-methoxyphenyl)-7-methylquinazoline

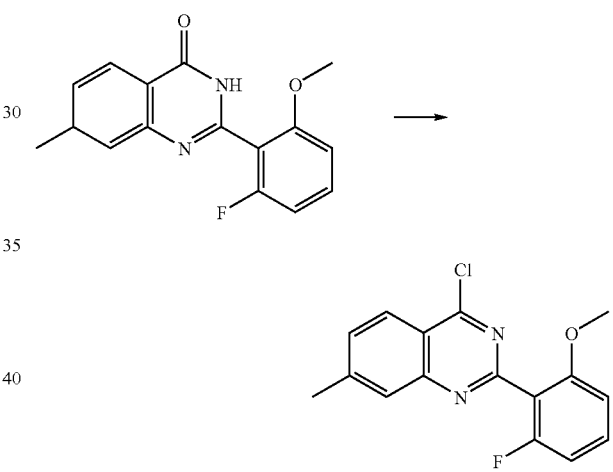

Under an N$_2$ atmosphere, 2-(2-fluoro-6-methoxyphenyl)-7-methylquinazolin-4(3H)-one (20 g, 70.35 mmol) was suspended in benzene (300 mL), followed by the addition of N,N-dimethylaniline (26.8 µL, 211.05 mmol), then POCl$_3$ (13.11 mL, 140.7 mmol). The reaction was heated at reflux, and completion of product formation was observed after 1.5 h. After cooling to room temperature, the mixture was slowly poured over 1 liter of ice. The solution was then diluted with CH$_2$Cl$_2$, and the pH was adjusted to 7 using a saturated aqueous NaHCO$_3$ solution. The layers were partitioned, separated and extracted with CH$_2$Cl$_2$. All organic layers were combined, dried over Na$_2$SO$_4$, filtered, and concentrated to a dark oil. The crude material was purified by silica gel chromatography using 75% CH$_2$Cl$_2$/25% hexanes to obtain 4-chloro-2-(2-fluoro-6-methoxyphenyl)-7-methylquinazoline as a yellow solid (18.82 g, 88%). LC/MS: m/z 302.9 (M+H)$^+$ at 3.28 min (10%-99% CH$_3$CN (0.035% TFA)/H$_2$O (0.05% TFA)). $^1$H NMR (400 MHz, CDCl$_3$) δ 8.22 (d, J=8.5 Hz, 1H), 7.95 (s, 1H), 7.60 (dd, J=8.6, 1.5 Hz, 1H), 7.42-7.40 (m, 1H), 6.86-6.84 (m, 2H), 3.81 (s, 3H), 2.64 (s, 3H) ppm.

2-(4-Chloro-7-methylquinazolin-2-yl)-3-fluorophenol

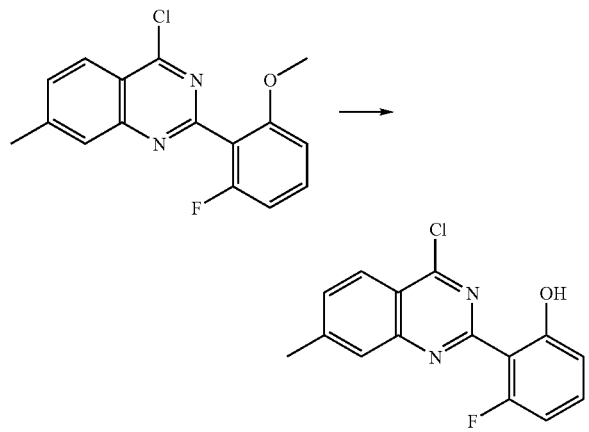

Under an N₂ atmosphere, 4-chloro-2-(2-fluoro-6-methoxyphenyl)-7-methylquinazolin (7.0 g, 23.12 mmol) was dissolved in CH₂Cl₂ (110 mL) and cooled to −50° C. internal temperature using a dry ice/acetone bath. A 1.0 M solution of BBr₃ in CH₂Cl₂ (115.6 mL, 115.6 mmol) was added dropwise via an addition funnel while maintaining the internal temperature at −50° C. The reaction mixture was warmed to 0° C., and the reaction was complete after 1.5 h. It was then slowly quenched with saturated aqueous NaHCO₃ solution to pH 7. After partitioning between CH₂Cl₂ and H₂O, the mixture was separated and the aqueous layer was twice extracted with CH₂Cl₂. The combined organic layers were dried over Na₂SO₄, filtered, and concentrated to a brown solid. Purification via silica gel chromatography using 75% CH₂Cl₂/25% hexanes gave 2-(4-chloro-7-methylquinazolin-2-yl)-3-fluorophenol as a yellow solid (4.37 g, 66%). LC/MS: m/z 289.1 (M+H)⁺ at 3.71 min (10%-99% CH₃CN (0.035% TFA)/H₂O (0.05% TFA)).

(R)-Benzyl 1-(2-(2-fluoro-6-hydroxyphenyl)-7-methylquinazolin-4-yl)pyrrolidin-3-ylcarbamate

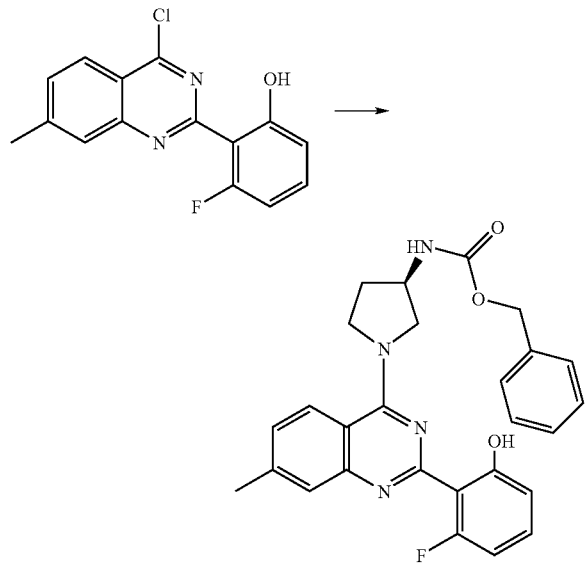

Under an N₂ atmosphere, a solution of 2-(4-chloro-7-methylquinazolin-2-yl)-3-fluorophenol (1.4 g, 4.85 mmol) in anhydrous CH₂Cl₂ (15 mL) was cooled in an ice bath. (R)-Benzyl pyrrolidin-3-yl carbamate (1.81 g, 5.82 mmol) was added in portions, followed by the addition of triethylamine (2.0 mL, 14.55 mmol). The reaction was warmed to RT and stirred for 1.5 h. The mixture was partitioned between CH₂Cl₂ and H₂O, the layers were separated, and the aqueous phase was extracted with CH₂Cl₂. The combined organic extracts were dried over Na₂SO₄, filtered, and concentrated under reduced pressure. Purification via silica gel chromatography using 0-20% EtOAc in a 1:1 mixture of CH₂Cl₂ and hexanes gave (R)-benzyl 1-(2-(2-fluoro-6-hydroxyphenyl)-7-methylquinazolin-4-yl)pyrrolidin-3-ylcarbamate (2.1 g, 92%). LC/MS: m/z 473.3 (M+H)⁺ at 2.51 min (10%-99% CH₃CN (0.035% TFA)/H₂O (0.05% TFA)).

(R)-2-(4-(3-Aminopyrrolidin-1-yl)-7-methylquinazolin-2-yl)-3-fluorophenol

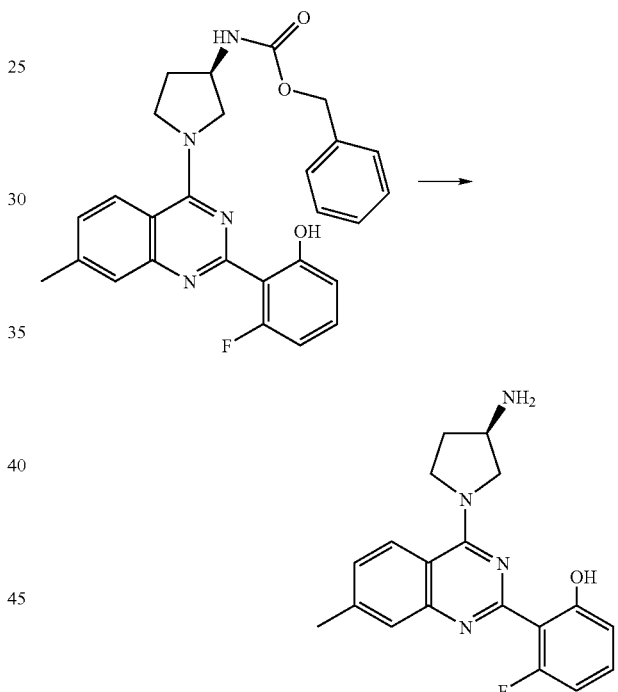

Under an N₂ atmosphere, Pd/C (10% weight, 210 mg) was added to a solution of (R)-benzyl 1-(2-(2-fluoro-6-hydroxyphenyl)-7-methylquinazolin-4-yl)pyrrolidin-3-ylcarbamate (2.1 g, 4.44 mmol) in MeOH (60 mL). After purging 2 times with N₂ and evacuating the atmosphere in the flask containing the reaction mixture, the reaction was stirred under an H₂ atmosphere for 16 h. Since the reaction was not complete, an additional 200 mg Pd/C was added, and the reaction was stirred for an additional 4 h. The mixture was filtered through a pad of Celite (150 mL) using 1.8 mL MeOH, and the filtrate was concentrated under reduced pressure to obtain (R)-2-(4-(3-aminopyrrolidin-1-yl)-7-methylquinazolin-2-yl)-3-fluorophenol as a yellow solid (1.4 g, 93%). LC/MS: m/z 339.1 (M+H)⁺ at 1.05 min (10%-99% CH₃CN (0.035% TFA)/H₂O (0.05% TFA)).

65

(R)-2-Methoxyethyl 1-(2-(2-fluoro-6-hydroxyphenyl)-7-methylquinazolin-4-yl)pyrrolidin-3-ylcarbamate (compound 1)

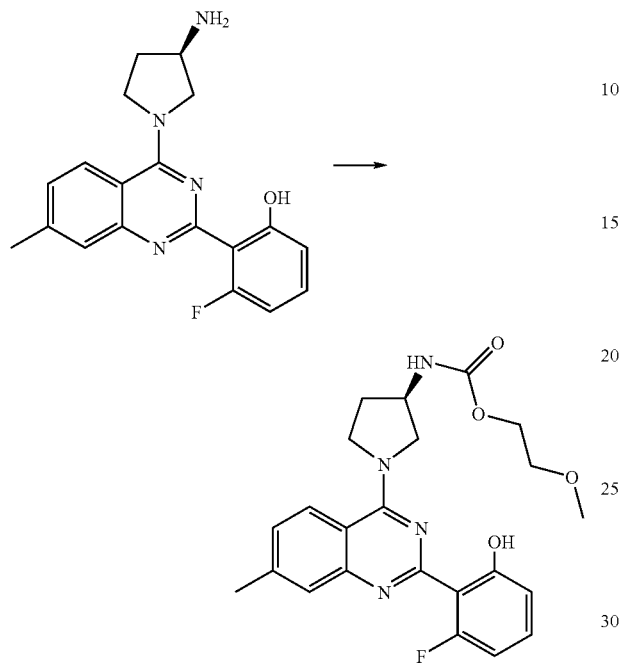

Method A. At 0° C., 2-methoxyethyl chloroformate (15 µL, 0.13 mmol) was added to a stirring mixture of (R)-2-(4-(3-aminopyrrolidin-1-yl)-7-methylquinazolin-2-yl)-3-fluorophenol (40 mg, 0.12 mmol), triethylamine (33 µL, 0.24 mmol), and DMF (0.8 mL). After allowing the reaction to warm to RT, purification via reverse phase HPLC (10%-99% CH$_3$CN (0.035% TFA)/H$_2$O (0.05% TFA)) gave (R)-2-methoxyethyl 1-(2-(2-fluoro-6-hydroxyphenyl)-7-methylquinazolin-4-yl)pyrrolidin-3-ylcarbamate (compound 1) as the TFA salt. LC/MS: m/z 441.5 (M+H)$^+$ at 2.04 min (10%-99% CH$_3$CN (0.035% TFA)/H$_2$O (0.05% TFA)).

Method B. To a mixture of (R)-2-(4-(3-aminopyrrolidin-1-yl)-7-methylquinazolin-2-yl)-3-fluorophenol (200 mg, 0.59 mmol) and THF (6 mL) was added triethylamine (165 µL, 1.18 mmol) to form a clear solution. The mixture was cooled to –50° C. external temperature, and a 1:1 mixture of 2-methoxyethyl chloroformate (65 µL) and THF (65 µL) was added dropwise. After complete addition, the reaction was quenched with H$_2$O and extracted with CH$_2$Cl$_2$. The combined organic extracts were dried over MgSO$_4$, filtered, and concentrated. Purification via silica gel chromatography using 0-10% EtOAc in a 1:1 mixture of hexanes and CH$_2$Cl$_2$ gave (R)-2-methoxyethyl 1-(2-(2-fluoro-6-hydroxyphenyl)-7-methylquinazolin-4-yl)pyrrolidin-3-ylcarbamate (compound 1) (130 mg, 50%). $^1$H NMR (400 MHz, DMSO-d6) δ 8.19 (d, J=8.7 Hz, 1H), 7.71 (d, J=6.1 Hz, 1H), 7.58 (s, 1H), 7.33 (m, 2H), 6.76 (d, J=8.3 Hz, 1H), 6.69 (m, 1H), 4.22 (m, 1H), 4.04 (m, 5H), 3.84 (m, 1H), 3.48 (t, J=4.6 Hz, 2H), 3.23 (s, 3H), 2.52 (s, 3H), 2.20 (m, 1H), 2.02 (m, 1H) ppm. LC/MS: m/z 441.5 (M+H)$^+$ at 2.10 min (10%-99% CH$_3$CN (0.035% TFA)/H$_2$O (0.05% TFA)).

66

(R)-2-Methoxyethyl 1-(2-(2-fluoro-6-hydroxyphenyl)-7-methylquinazolin-4-yl)pyrrolidin-3-ylcarbamate hydrochloride (HCl salt of compound 1)

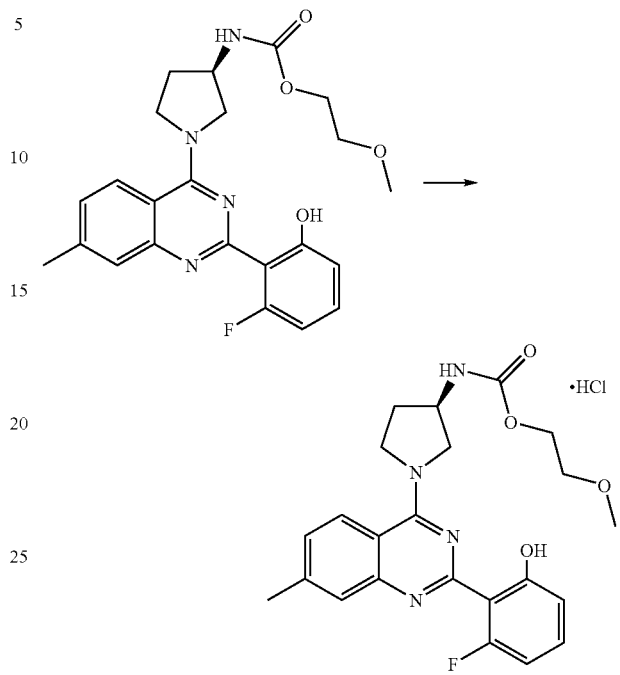

A 2.0 M solution of HCl in ether (0.15 mL) was added to solution of (R)-2-methoxyethyl 1-(2-(2-fluoro-6-hydroxyphenyl)-7-methylquinazolin-4-yl)pyrrolidin-3-ylcarbamate (130 mg, 0.3 mmol) in CH$_2$Cl$_2$ (2 mL) and ether (10 mL). After addition of ether (10 mL), a precipitate formed which was filtered and dried. The material was dissolved in MeOH and dried under reduced pressure to give (R)-2-methoxyethyl 1-(2-(2-fluoro-6-hydroxyphenyl)-7-methylquinazolin-4-yl)pyrrolidin-3-ylcarbamate hydrochloride (HCl salt of compound 1) as a solid. $^1$H NMR (400 MHz, DMSO-d6) δ 8.35 (s, 1H), 7.76 (d, J=5.5 Hz, 1H), 7.67 (s, 1H), 7.59 (d, J=8.6 Hz, 1H), 7.47 (m, 1H), 6.99 (d, J=8.3 Hz, 1H), 6.87 (t, J=9.0 Hz, 1H), 4.29 (m, 3H), 3.77-3.36 (m, 5H), 3.23 (s, 3H), 3.06 (m, 1H), 2.56 (s, 3H), 2.23 (s, 1H), 2.06 (s, 1H) ppm. LC/MS: m/z 441.3 (M+H)$^+$ at 2.11 min (10%-99% CH$_3$CN (0.035% TFA)/H$_2$O (0.05% TFA)).

Example 2

(S)-{1-[2-(2-Hydroxy-phenyl)-7-methyl-quinazolin-4-yl]-pyrrolidin-3-yl}-carbamic acid tert-butyl ester

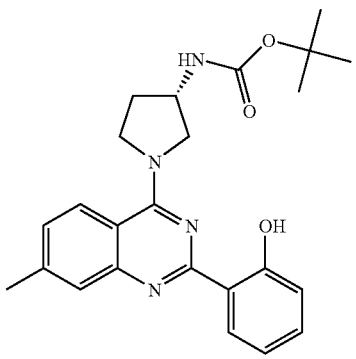

N-(2-Cyano-5-methyl-phenyl)-2-methoxy-benzamide

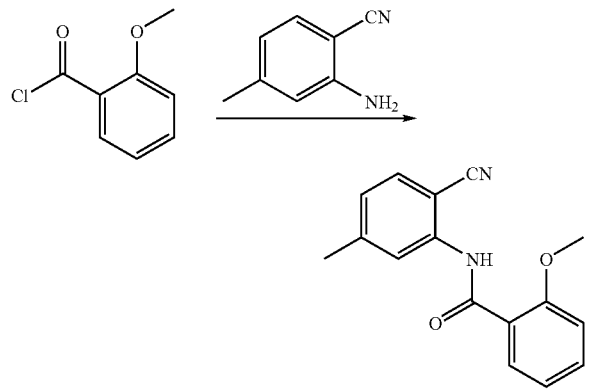

To a stirred solution of 4-methyl-2-aminobenzonitrile (100 g, 0.75 mol) in 800 mL CH$_2$Cl$_2$ was added triethylamine (77.4 g, 0.76 mol) and dimethylaminopyridine (4.62 g, 0.037 mol). The solution was cooled to 0-5° C., and o-anisoyl chloride (129 g, 0.75 mol) was added over 1 h while maintaining the reaction temperature at 0-5° C. The reaction was then stirred at 30-40° C. for 3 h. Water (400 mL) was added, and the mixture was stirred for 15 minutes. The organic layer was separated, and the aqueous solution was extracted with CH$_2$Cl$_2$ (600 mL). The combined organic layers were dried over sodium sulfate, filtered, and concentrated in vacuo to yield a solid residue, to which 800 mL hexane were added. The slurry was stirred and filtered to give N-(2-cyano-5-methyl-phenyl)-2-methoxy-benzamide as a yellow powder (180 g, 90%). mp 147-149° C. $^1$H NMR (CDCl$_3$) δ 2.429 (s, 3H), 4.2 (s, 3H), 6.8-7.2 (m, 3H), 7.4-7.6 (m, 2H), 8.2-8.4 (d, 1H), 8.6 (s, 1H), 10.8 (bs, 1H) ppm; $^{13}$C NMR (CDCl$_3$) δ 22.68, 55.7, 99, 111.27, 116.7, 120.3, 121.1, 124.15, 131.7, 132.25, 133.67, 141.32, 141.1, 157.2, 163. M/z (obs., [m+H]$^+$)=268.

2-(2-Methoxyphenyl)-7-methyl-3H-quinazolin-4-one

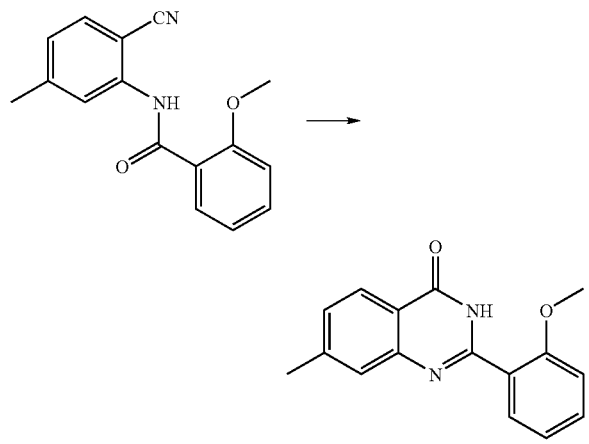

To a mechanically stirred suspension of N-(2-cyano-5-methylphenyl)-2-methoxybenzamide (180 g, 0.67 mol) in 1.8 L ethanol under an N$_2$ atmosphere was added 6 N sodium hydroxide solution (310 g in 1.25 L water). To the above mixture, 30% hydrogen peroxide (350 mL, 3.64 mol) was slowly added. The solution was then slowly heated to 80° C. and maintained at this temperature for 4 h. The reaction mixture was concentrated under reduced pressure to remove ethanol, giving a suspension which was quenched with ice cold water (1.8 L) and acidified with acetic acid to pH 5-6 to give a solid residue. The solid was filtered and washed with water, then dissolved in 5.5 L CH$_2$Cl$_2$ and washed with water (2×18 L). The organic layer was dried over sodium sulfate, and the solvent was removed under reduced pressure to give a light yellow solid (100 g, 54%). mp 165-170° C. $^1$H NMR (CDCl$_3$) δ 2.429 (s, 3H), 4.2 (s, 3), 6.8-7.2 (m, 3H), 7.4-7.6 (m, 2H), 8.2-8.4 (d, 1H), 8.6 (s, 1H), 10.8 (bs, 1H) ppm; $^{13}$CNMR (CDCl$_3$) δ21.68, 55.6, 111.3, 118.2, 119.6, 121.1, 125.7, 127.14, 127.64, 130.96, 132.56, 144.9, 149.06, 150.42, 157.25, 161.52. M/z (obs., [m+H]$^+$)=268.

4-Chloro-2-(2-methoxy-phenyl)-7-methyl-quinazoline

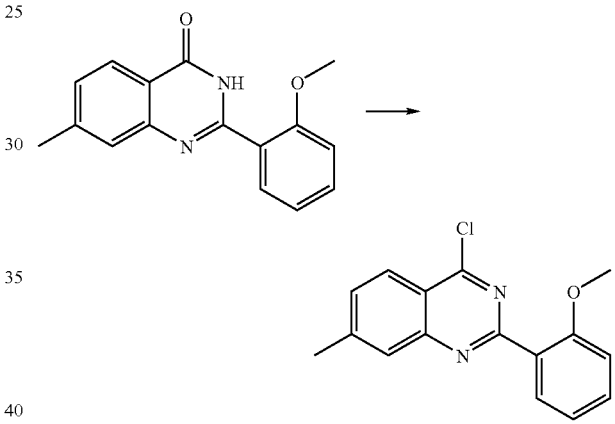

To a mechanically stirred suspension of 2-(2-methoxyphenyl)-7-methyl-3H-quinazolin-4-one (100 g, 0.37 mol) in 1 L toluene was added diisopropyl ethylamine (100 mL), followed by phosphorus oxychloride (69 g, 0.45 mol). The reaction was then heated to 80° C. for 4 h. The reaction mixture was distilled under reduced pressure to remove toluene, and the resulting residue was dissolved in 2.2 L CH$_2$Cl$_2$. Ice water was added, and the pH was adjusted to 8-9 with saturated aqueous sodium bicarbonate solution while maintaining the temperature below 20° C. The resulting organic layer was separated and the aqueous solution extracted with CH$_2$Cl$_2$, then the combined the organic layers were dried over sodium sulfate and distilled under reduced pressure. The crude product was dissolved 2:1 CH$_2$Cl$_2$/hexane, and the solution was passed through silica gel (2.5 kg, 60-120 mesh), followed by washing the silica bed with 2:1 CH$_2$Cl$_2$/hexane until the product eluted. The pure fractions were collected and combined, and the solvent was removed under reduced pressure. Hexane (500 mL) was added, and the mixture was stirred and filtered to give 4-chloro-2-(2-methoxy-phenyl)-7-methyl-quinazoline as a white to off-white solid (77 g, 72%). mp 161-164° C. $^1$H NMR (CDCl$_3$) δ 2.6 (s, 3H), 3.9 (s, 3H), 6.9-7.2 (m, 2H), 7.4-7.6 (m, 2H), 7.7-8 (d, 2H), 8.2 (d, 1H) ppm; M/z (obs., [m+H]$^+$)=285.

2-(4-Chloro-7-methylquinazolin-2-yl)phenol

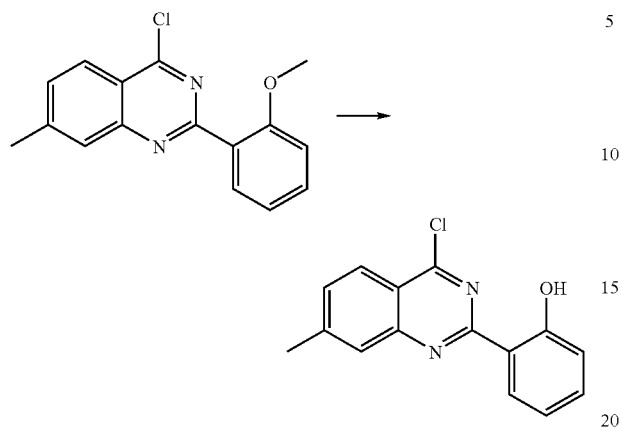

Boron tribromide in dichloromethane (1 M, 900 mL, 900 mmol) was added drop wise to a cooled (−30—40° C.) solution of 4-chloro-2-(2-methoxyphenyl)-7-methylquinazoline (93.2 g, 328 mmol) in dichloromethane (2 L) under nitrogen atmosphere. The resulting mixture was left warming to room temperature in about four hours and was slowly poured in 4 L sat. aq. NaHCO$_3$. Stirring was continued until no more CO$_2$ was produced. The layers were separated and the organic layer was dried over sodium sulfate, filtered, and evaporated to dryness under reduced pressure, yield: 90 g. The residue was filtered over a short plug of silica with dichloromethane as the eluent. Yield: 57.9 g (65%) of 2-(4-chloro-7-methylquinazolin-2-yl)phenol ($^1$H-NMR, LC-MS: >90% purity). It was found that the only impurity still present was the corresponding bromo quinazoline (LC-MS, M$^+_{found}$=271 [M$^+$1]; 315, 317 [M-Cl+Br], Br-isotope patterns present).

(S)-{1-[2-(2-Hydroxy-phenyl)-7-methyl-quinazolin-4-yl]-pyrrolidin-3-yl}-carbamic acid tert-butyl ester

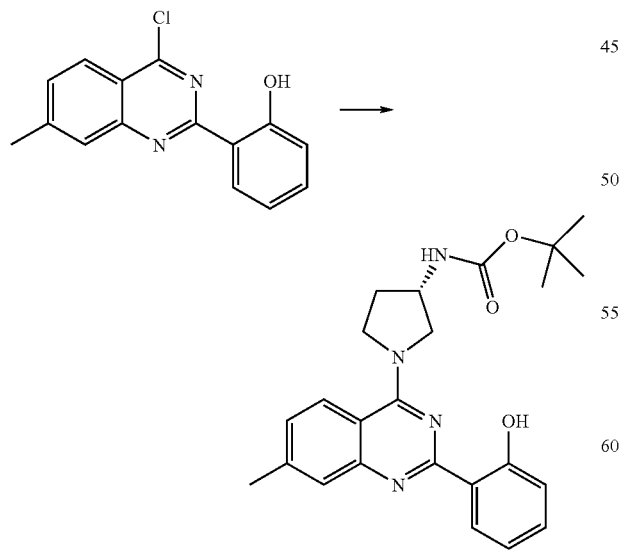

To 2-(4-chloro-7-methyl-quinazolin-2-yl)-phenol (551 mg, 2.03 mmol) in 2.5 mL of DMF at room temperature were added sequentially (S)-pyrrolidin-3-yl-carbamic acid tert-butyl ester (740 mg, 3.9 mmol) and triethylamine (567 μL, 4.0 mmol), and the reaction mixture was stirred for 12 h. The reaction mixture was diluted with water (10 mL) and CH$_2$Cl$_2$ (10 mL). The organic layer was separated and dried (Na$_2$SO$_4$), and the solvent was removed under reduced pressure. The residue was purified via silica gel chromatography with 25%-85% ethyl acetate/hexanes to give (S)-{1-[2-(2-hydroxy-phenyl)-7-methyl-quinazolin-4-yl]-pyrrolidin-3-yl}-carbamic acid tert-butyl ester (694 mg, 81%). LC/MS: m/z 421 (M+H)$^+$ at 2.79 min (10%-99% CH$_3$CN (0.035% TFA)/H$_2$O (0.05% TFA)).

Example 3

(R)-Ethyl 1-(2-(2-hydroxyphenyl)-7-methylquinazolin-4-yl)pyrrolidin-3-ylcarbamate (compound 2)

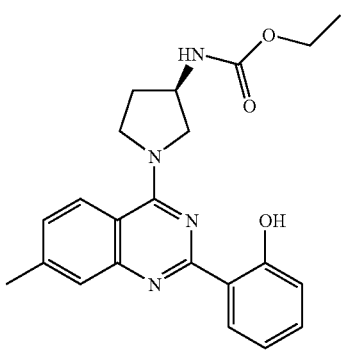

tert-Butyl (R)-1-(2-(2-hydroxyphenyl)-7-methylquinazolin-4-yl)pyrrolidin-3-ylcarbamate

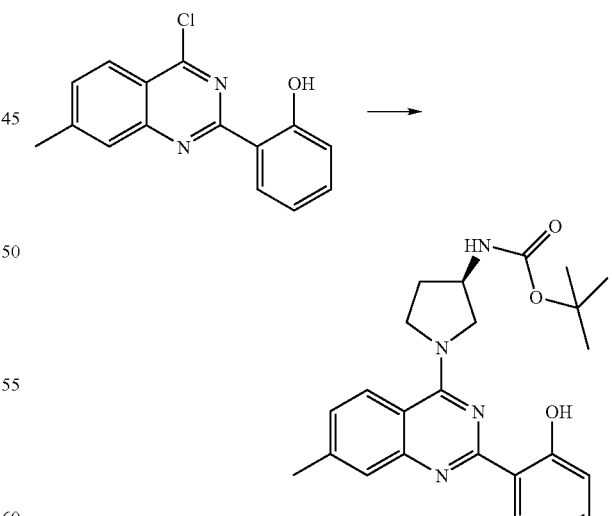

To a cooled (0-5° C.) solution of (3R)-(+)-3-Boc-aminopyrrolidine (12.0 g, 65 mmol) and triethylamine (19 mL, 129 mmol) in DMF (100 mL) was added a solution of 2-(4-chloro-7-methylquinazolin-2-yl)phenol (17.4 g, 64 mmol) in CH$_2$Cl$_2$ (500 mL) and DMF (100 mL). After stirring the mixture for 5 hours at room temperature, water (900 mL) was added. The aqueous layer was extracted with dichloromethane (3×300 mL), and the combined organic layers were washed with saturated aqueous NaCl solution (300 mL), dried over sodium sulfate, filtered, and evaporated to dryness under reduced pressure. The yellow residue (21 g) was treated with 100 mL methanol at room temperature. The solid was collected by filtration and was washed with methanol to yield tert-butyl (R)-1-(2-(2-hydroxyphenyl)-7-methylquinazolin-4-yl)pyrrolidin-3-ylcarbamate (15.1 g, 55%) as a yellow solid.

2-(4-((R)-3-Aminopyrrolidin-1-yl)-7-methylquinazolin-2-yl)phenol

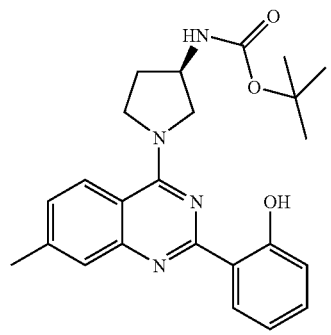

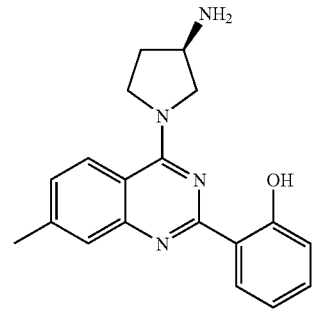

tert-Butyl (R)-1-(2-(2-hydroxyphenyl)-7-methylquinazolin-4-yl)pyrrolidin-3-ylcarbamate (15.1 g, 36 mmol) was treated with trifluoroacetic acid (50 mL) in dichloromethane (100 mL) at room temperature for about three hours. The solution was evaporated to dryness and the residue was stripped with toluene (100 mL). 10% aq. sodium carbonate solution (300 mL), CH$_2$Cl$_2$ (400 mL), and methanol (100 mL) [methanol is added because 2-(4-((R)-3-aminopyrrolidin-1-yl)-7-methylquinazolin-2-yl)phenol is not very soluble in pure CH$_2$Cl$_2$] were added to the residue and stirring was continued until all solids were dissolved. The layers were separated and the aqueous layer was extracted with a mixture of CH$_2$Cl$_2$ (400 mL) and methanol (100 mL). The combined organic layers were washed with saturated aqueous NaCl solution (200 mL), dried over sodium sulfate, filtered, and evaporated to dryness to give 2-(4-((R)-3-aminopyrrolidin-1-yl)-7-methylquinazolin-2-yl)phenol (11.0 g, 95%) as a yellow solid with 98+% purity.

(R)-Ethyl 1-(2-(2-hydroxyphenyl)-7-methylquinazolin-4-yl)pyrrolidin-3-ylcarbamate (compound 2)

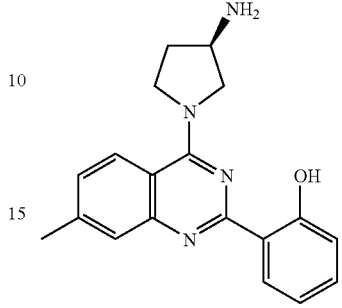

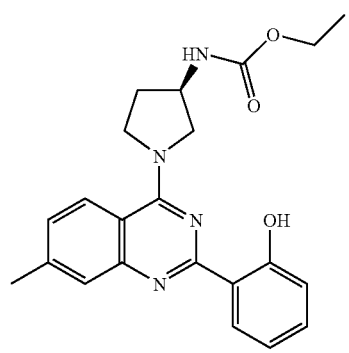

Method A At −50° C., ethyl chloroformate (12 µL, 0.12 mmol) was added rapidly to a solution of (R)-2-(4-(3-aminopyrrolidin-1-yl)-7-methylquinazolin-2-yl)phenol (40 mg, 0.12 mmol) and triethylamine (34 µL, 0.24 mmol) in DMF (0.8 mL). The reaction was warmed to RT over a period of 1 h. Purification via reverse phase HPLC (10%-99% CH$_3$CN (0.035% TFA)/H$_2$O (0.05% TFA)) gave (R)-ethyl 1-(2-(2-hydroxyphenyl)-7-methylquinazolin-4-yl)pyrrolidin-3-ylcarbamate (compound 2) as the TFA salt. LC/MS: m/z 393.3 (M+H)$^+$ at 2.04 min (10%-99% CH$_3$CN (0.035% TFA)/H$_2$O (0.05% TFA)).

Method B. Under an N$_2$ atmosphere at RT, triethylamine (174 µL, 1.25 mmol) was added to a solution of (R)-2-(4-(3-aminopyrrolidin-1-yl)-7-methylquinazolin-2-yl)phenol (200 mg, 0.62 mmol) in THF (6.0 mL). After cooling the mixture to −55° C., ethyl chloroformate (59 µL in 600 µL THF, 0.62 mmol) was slowly added, and the reaction was warmed to RT over a period of 30 minutes. The mixture was quenched with H$_2$O and extracted with CH$_2$Cl$_2$. The combined organic layers were dried over MgSO$_4$, filtered, and concentrated. Purification via silica gel chromatography using 0-20% EtOAc in a 1:1 mixture of CH$_2$Cl$_2$ and hexanes gave (R)-ethyl 1-(2-(2-hydroxyphenyl)-7-methylquinazolin-4-yl)pyrrolidin-3-ylcarbamate (compound 2) (210 mg, 86%). $^1$H NMR (400 MHz, DMSO-d6) δ 8.42 (dd, J=7.8, 1.5 Hz, 1H), 8.18 (d, J=8.7 Hz, 1H), 7.59-7.58 (m, 2H), 7.38-7.33 (m, 2H), 6.94-6.90 (m, 2H), 4.27-4.12 (m, 3H), 4.04-3.98 (m, 3H), 3.87-3.86 (m, 1H), 2.50 (s, 3H), 2.26-2.18 (m, 1H), 2.05-1.99 (m, 1H), 1.16 (t, J=7.3 Hz, 3H) ppm. LC/MS: m/z 393.3 (M+H)$^+$ at 2.31 min (10%-99% CH$_3$CN (0.035% TFA)/H$_2$O (0.05% TFA)).

73

(R)-Ethyl 1-(2-(2-hydroxyphenyl)-7-methylquinazo-lin-4-yl)pyrrolidin-3-ylcarbamate hydrochloride (HCl salt of compound 2)

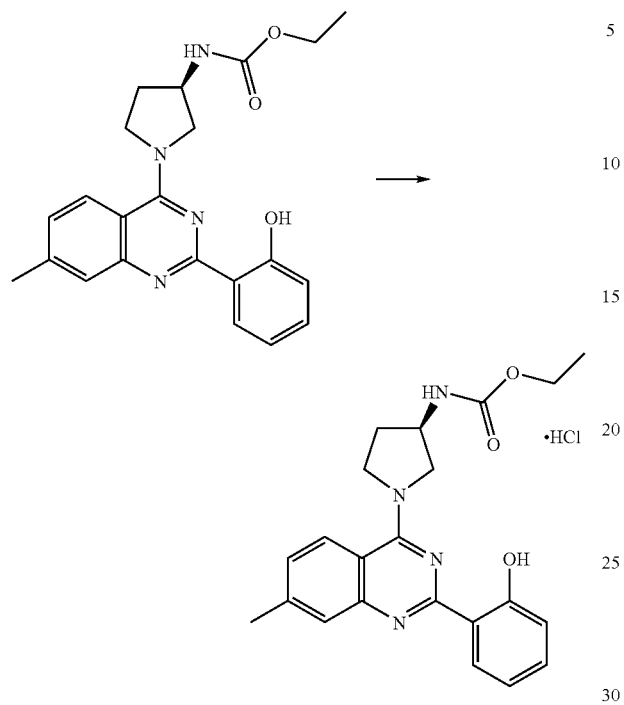

Under an $N_2$ atmosphere, a 1.0 M solution of HCl in ether (0.53 mL, 0.53 mmol) was added dropwise to a solution of (R)-ethyl 1-(2-(2-hydroxyphenyl)-7-methylquinazolin-4-yl) pyrrolidin-3-ylcarbamate (208 mg, 0.53 mmol) in $CH_2Cl_2$ (13 mL). After stirring the reaction for 10 minutes, ether (30 mL) was added, and a precipitate formed which was filtered and dried to give (R)-ethyl 1-(2-(2-hydroxyphenyl)-7-methylquinazolin-4-yl)pyrrolidin-3-ylcarbamate hydrochloride (HCl salt of compound 2). $^1$H NMR (400 MHz, DMSO-d6) δ 8.29-8.23 (m, 2H), 7.78 (s, 1H), 7.61 (d, J=5.1 Hz, 1H), 7.52-7.48 (m, 2H), 7.10 (d, J=8.1 Hz, 1H), 7.06-7.02 (m, 2H), 4.29-4.13 (m, 4H), 4.03-3.94 (m, 3H), 2.54 (s, 3H), 2.27-2.22 (m, 1H), 2.08-2.06 (m, 1H), 1.16 (t, J=7.0 Hz, 3H) ppm. LC/MS: m/z 393.3 (M+H)$^+$ at 2.36 min (10%-99% $CH_3CN$ (0.035% TFA)/$H_2O$ (0.05% TFA)).

Example 4

(R)-Propyl 1-(2-(2-hydroxyphenyl)-7-meth-ylquinazolin-4-yl)pyrrolidin-3-ylcarbamate (compound 3)

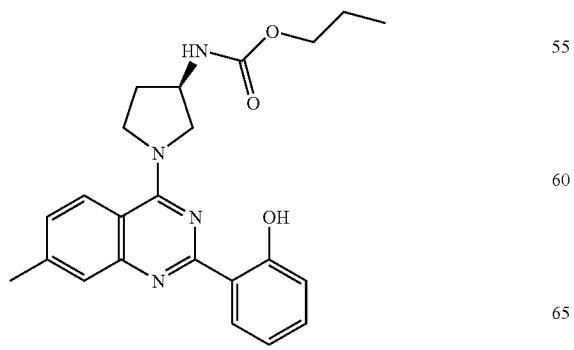

74

(R)-Propyl 1-(2-(2-hydroxyphenyl)-7-meth-ylquinazolin-4-yl)pyrrolidin-3-ylcarbamate (compound 3)

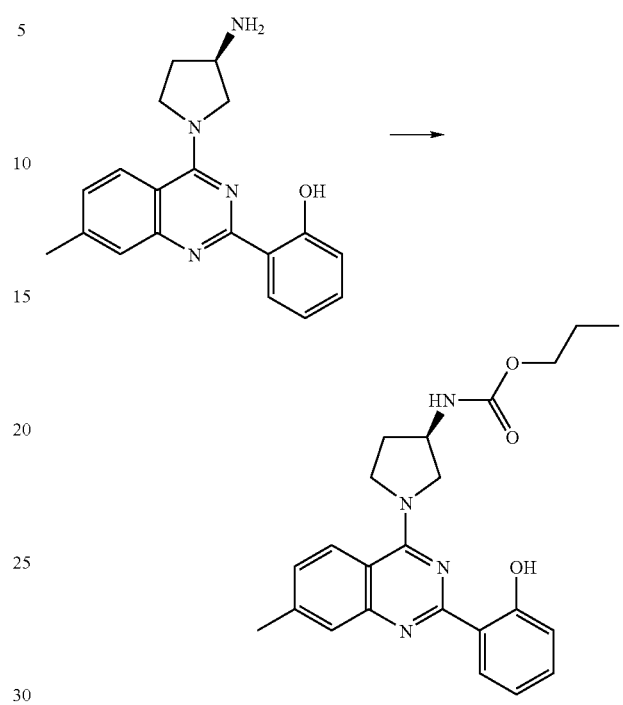

At −50° C., n-propyl chloroformate (14 µL, 0.12 mmol) was added rapidly to a solution of (R)-2-(4-(3-aminopyrroli-din-1-yl)-7-methylquinazolin-2-yl)phenol (40 mg, 0.12 mmol) and triethylamine (34 µL, 0.24 mmol) in DMF (0.8 mL). The reaction was warmed to RT over a period of 1 h. Purification via reverse phase HPLC (10%-99% $CH_3CN$ (0.035% TFA)/$H_2O$ (0.05% TFA)) gave (R)-propyl 1-(2-(2-hydroxyphenyl)-7-methylquinazolin-4-yl)pyrrolidin-3-yl-carbamate (compound 3) as the TFA salt. LC/MS: m/z 407.5 (M+H)$^+$ at 2.42 min (10%-99% $CH_3CN$ (0.035% TFA)/$H_2O$ (0.05% TFA)).

Example 5

(R)-Neopentyl 1-(6-fluoro-2-(2-hydroxyphenyl) quinazolin-4-yl)pyrrolidin-3-ylcarbamate (compound 4)

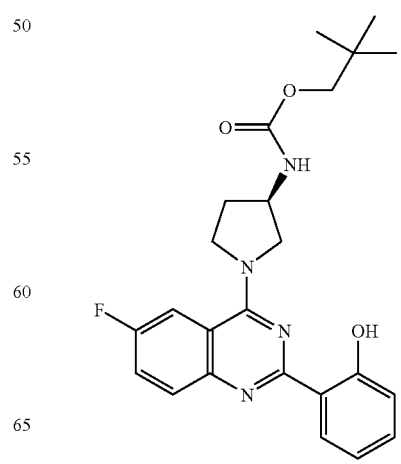

(E)-N-(4-Fluorophenyl)-2-(hydroxyimino)acetamide

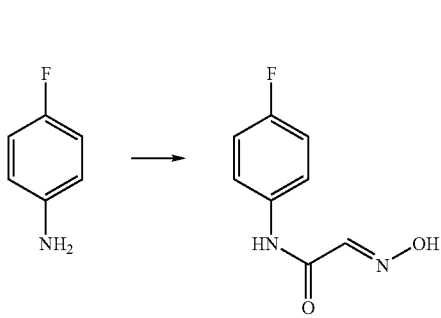

4-Fluoroaniline (58.2 g, 0.50 mol) was added slowly to 10% aqueous HCl solution. This suspension was added to a mixture of chloral hydrate (95 g, 0.55 mol) and sodium sulfate (0.5 kg) in 750 mL water with mechanical stirring. Hydroxylamine hydrochloride (116 g, 1.63 mol) dissolved in water (250 mL) was added, and the resulting slurry was heated at 100° C. After this temperature was reached, the heating mantle was removed immediately, and the solution was cooled to room temperature. The formed precipitate was collected by filtration, washed with water (2×300 mL), and dried in a vacuum oven at 60° C. Yield: 78.2 g of N-(4-fluorophenyl)-2-hydroxyiminoacetamide as an off-white solid.

5-Fluoroindoline-2,3-dione

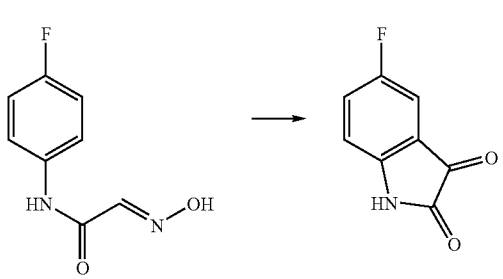

Concentrated sulfuric acid (200 mL) was heated at 50° C., and N-(4-fluorophenyl)-2-hydroxyiminoacetamide was slowly added. The black solution was carefully heated at 90° C. At this temperature, some slight cooling was necessary to keep the temperature at 90° C. When no more heat had developed, the reaction mixture was heated at 90° C. for an additional half hour. The dark-red solution was cooled to room temperature and poured onto 3 L ice water and 1 L ethyl acetate with vigorous stirring. The layers were separated, and the aqueous layer was extracted with ethyl acetate (1×1 L, 1×0.5 L). The combined organic extracts were dried over sodium sulfate, filtered, and evaporated to dryness. Yield: 35.3 g (52%) of a dark red solid, 5-fluoro-1H-indole-2,3-dione.

2-Amino-5-fluorobenzamide

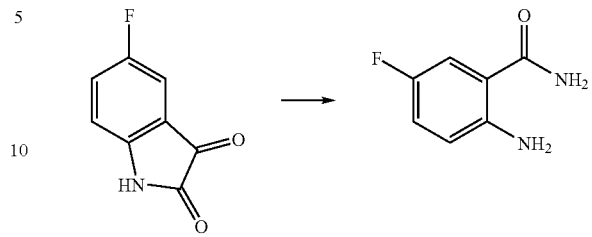

5-Fluoro-1H-indole-2,3-dione (35.3 g, 213 mmol) was heated in acetic acid (300 mL), 1 mL concentrated sulfuric acid, and 22 mL 35% aq. hydrogen peroxide at 70° C. The solution was kept at that temperature one and a half hours during which time a solid formed in the reaction mixture. After cooling to room temperature this solid was collected by filtration and was washed three times with water. The wet solid was suspended in 150 mL water, and 40 mL of a 25% aq. ammonia solution was added. This mixture was stirred at room temperature 3 days. The formed solid was collected by filtration and was washed twice with water. The solid was dried by azeotropic distillation with toluene (3×100 mL) to yield 2-amino-5-fluorobenzamide (9.5 g). The combined filtrates were extracted with ethyl acetate (2×100 mL). The combined extracts were dried over sodium sulfate, filtered, and evaporated to dryness to yield 2-amino-5-fluorobenzamide (3.5 g) as an off-white solid. Both fractions were combined for use in the next reaction step.

6-Fluoro-2-(2-methoxyphenyl)-3H-quinazolin-4-one

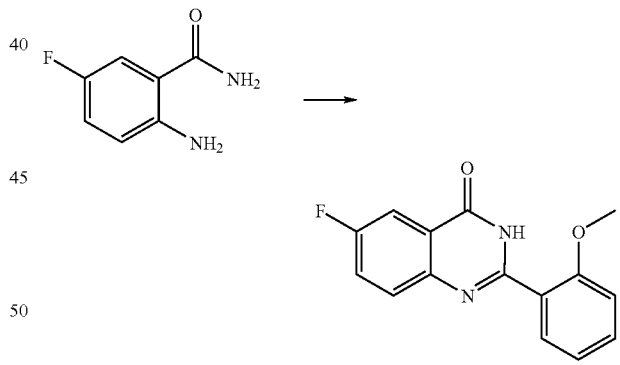

o-Anisoyl chloride (15.7 g, 92 mmol) was added dropwise to a solution of 2-amino-5-fluorobenzamide (13.0 g, 84 mmol) and triethylamine (16 mL, 110 mmol) in tetrahydrofuran (100 mL) cooled in an ice bath. Immediately a precipitate started forming. Stirring of the solution was continued for 5 hours at room temperature. The formed precipitate was collected by filtration and was washed twice with diethyl ether and dried at 50° C. in vacuo. The dried solid was suspended in 2 N aqueous sodium hydroxide solution (250 mL) and heated at reflux until a clear solution was obtained (3 hours). The reaction mixture was cooled to room temperature and filtered. The filtrate was acidified to pH<1 with concentrated aqueous HCl. The formed precipitate was collected by filtration and washed twice with water, twice with methanol, and twice with diethyl ether. The solid was dried in an oven at 45° C. to yield 6-fluoro-2-(2-methoxyphenyl)-3H-quinazolin-4-one (18.2 g, 80%) as a white solid.

4-Chloro-6-fluoro-2-(2-methoxyphenyl)quinazoline

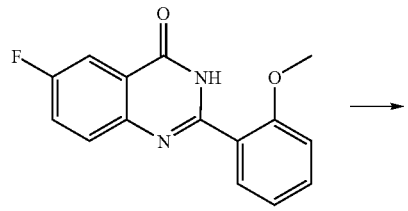

A suspension of 6-fluoro-2-(2-methoxyphenyl)-3H-quinazolin-4-one (14.0 g, 52 mmol), N,N-dimethylaniline (6.6 mL, 52 mmol), and phosphorus oxychloride (4.8 mL, 52 mmol) in benzene (100 mL) was heated at reflux until a clear, dark solution was obtained (1 hour). The reaction mixture was cooled to room temperature, and the volume was reduced under reduced pressure. The black, oily residue was poured into 300 g of ice. Dichloromethane (600 mL) was added with vigorous stirring, and the temperature was kept below 5° C. at all times. The pH was monitored, and aqueous 1 N sodium hydroxide was added until the pH was 10-11. The mixture was stirred for one hour at a temperature below 5° C., and the pH was kept between 10-11 by addition of 1 N aqueous sodium hydroxide. The layers were separated, and the organic layer was washed with ice cold 1 N aqueous sodium hydroxide (2×200 mL). Heptanes (300 mL) were added to the organic layer. This mixture was filtered through a short plug of silica gel and eluted with dichloromethane/heptanes (2:1). All fractions containing product were combined and evaporated to dryness. The residue was triturated with heptanes to yield 4-chloro-6-fluoro-2-(2-methoxyphenyl)-quinazoline (11.5 g, 76%) as a white solid.

2-(4-Chloro-6-fluoroquinazolin-2-yl)phenol

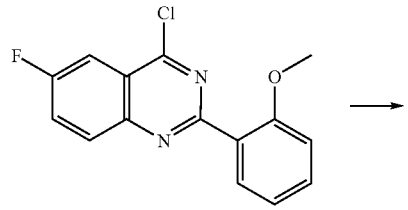

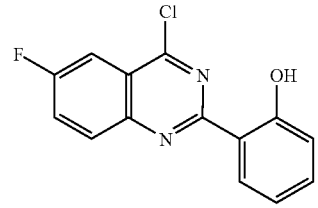

A solution of 4-chloro-6-fluoro-2-(2-methoxyphenyl)quinazoline (3.0 g, 10.3 mmol) in CH$_2$Cl$_2$ (15 mL) was cooled to −78° C. Then, 1 M BBr$_3$ (51.95 mL, 59.95 mmol) was added dropwise. The reaction was warmed to room temperature and was quenched with NaHCO$_3$ and extracted twice with CH$_2$Cl$_2$. The organic layer was dried over MgSO$_4$, filtered, and concentrated. Purification via silica gel chromatography using 5-20% CH$_2$Cl$_2$ in hexanes gave 2-(4-chloro-6-fluoroquinazolin-2-yl)phenol (1.61 g, 57%). LC/MS: m/z 275.1 (M+H)$^+$ at 3.8 min (10%-99% CH$_3$CN (0.035% TFA)/H$_2$O (0.05% TFA)).

(R)-Benzyl 1-(6-fluoro-2-(2-hydroxyphenyl)quinazolin-4-yl)pyrrolidin-3-ylcarbamate

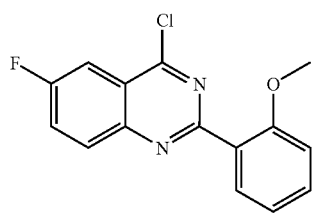

A solution of (R)-benzyl pyrrolidin-3-ylcarbamate oxalate (1.35 g, 4.38 mmol) in CH$_2$Cl$_2$ (5 mL) was added dropwise to a solution of 2-(4-chloro-6-fluoroquinazolin-2-yl)phenol (1.0 g, 3.6 mmol) and triethylamine (1.22 mL, 8.76 mmol) in CH$_2$Cl$_2$ (10 mL). After stirring the mixture for 2 h, the reaction was quenched with H$_2$O, the layers were separated, and the aqueous layer was extracted with CH$_2$Cl$_2$. The combined organic extracts were dried over MgSO$_4$, filtered, and concentrated. The residue was purified via silica gel chromatography using 5-10% EtOAc in CH$_2$Cl$_2$ to give (R)-benzyl 1-(6-fluoro-2-(2-hydroxyphenyl)quinazolin-4-yl)pyrrolidin-3-ylcarbamate (1.37 g, 82%). $^1$H NMR (400 MHz, CDCl$_3$) δ 8.39 (d, J=6.9 Hz, 1H), 7.80 (s, 1H), 7.68 (d, J=8.5 Hz, 1H), 7.46 (m, 1H), 7.37 (m, 6H), 7.01 (d, J=7.8 Hz, 1H), 6.90 (t, J=7.5 Hz, 1H), 5.17 (m, 2H), 4.51 (s, 1H), 4.25 (m, 1H), 4.10 (m, 2H), 3.91 (m, 1H), 2.37 (m, 1H), 2.12 (m, 1H). LC/MS: m/z 459.5 (M+H)$^+$ at 2.80 min (10%-99% CH$_3$CN (0.035% TFA)/H$_2$O (0.05% TFA)).

(R)-2-(4-(3-Aminopyrrolidin-1-yl)-6-fluoroquinazolin-2-yl)phenol

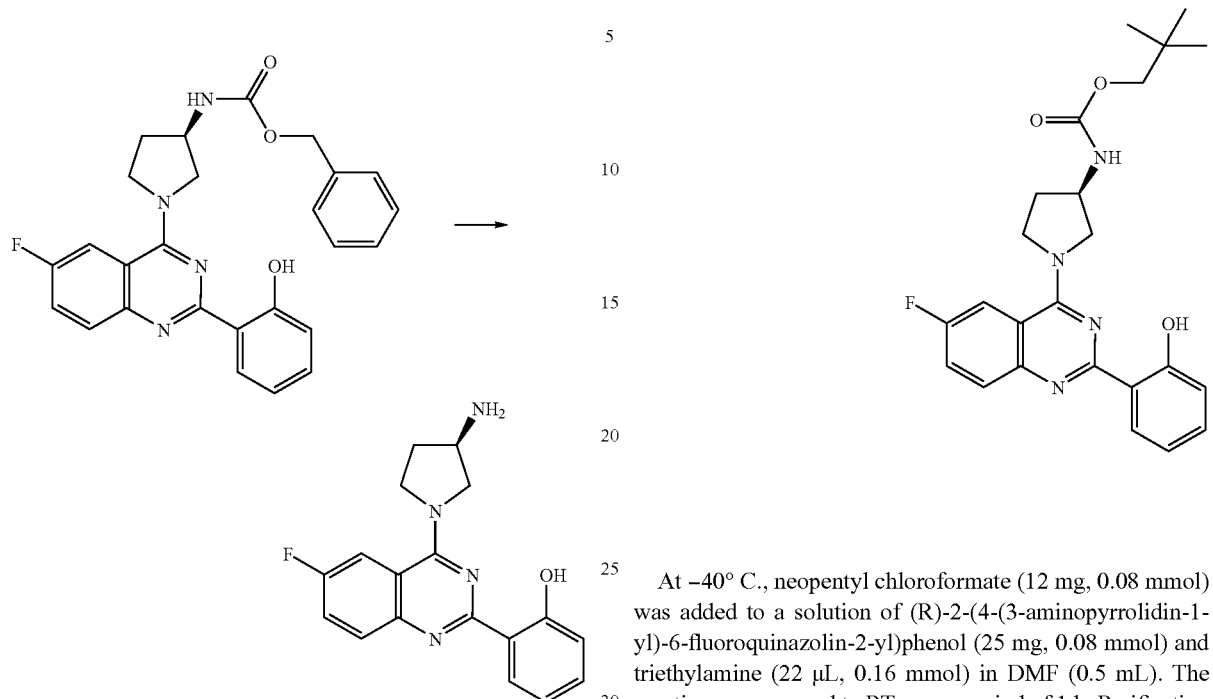

Under an $N_2$ atmosphere, Pd/C (10% weight, 140 mg) was added to a solution of (R)-benzyl 1-(6-fluoro-2-(2-hydroxyphenyl)quinazolin-4-yl)pyrrolidin-3-ylcarbamate (1.37 g, 5.3 mmol) in MeOH (10 mL). After purging twice with $N_2$ and evacuating the atmosphere in the flask containing the reaction mixture, the reaction was stirred under an $H_2$ atmosphere overnight. The mixture was filtered through a pad of Celite, and the filtrate was concentrated under reduced pressure to obtain (R)-2-(4-(3-aminopyrrolidin-1-yl)-6-fluoroquinazolin-2-yl)phenol (940 mg, 98%). $^1$H NMR (400 MHz, $CDCl_3$) δ 8.41 (m, 1H), 7.73 (m, 2H), 7.40 (m, 1H), 7.28 (m, 1H), 6.94 (m, 1H), 6.85 (m, 1H), 4.15 (m, 2H), 3.99 (m, 1H), 3.77 (m, 1H), 3.68 (m, 1H), 2.20 (m, 1H), 1.86 (m, 1H) ppm. LC/MS: m/z 325.3 $(M+H)^+$ at 1.68 min (10%-99% $CH_3CN$ (0.035% TFA)/$H_2O$ (0.05% TFA)).

(R)-Neopentyl 1-(6-fluoro-2-(2-hydroxyphenyl)quinazolin-4-yl)pyrrolidin-3-ylcarbamate (compound 4)

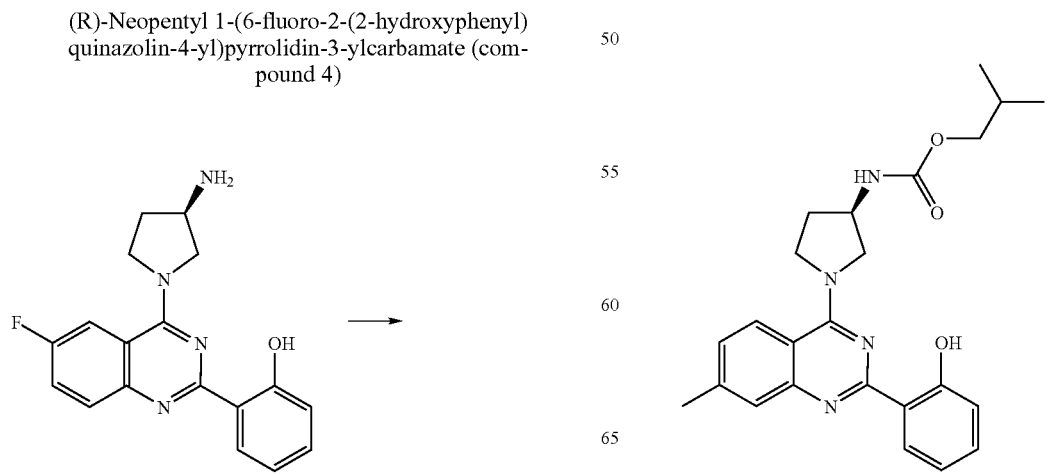

At −40° C., neopentyl chloroformate (12 mg, 0.08 mmol) was added to a solution of (R)-2-(4-(3-aminopyrrolidin-1-yl)-6-fluoroquinazolin-2-yl)phenol (25 mg, 0.08 mmol) and triethylamine (22 μL, 0.16 mmol) in DMF (0.5 mL). The reaction was warmed to RT over a period of 1 h. Purification via reverse phase HPLC (10%-99% $CH_3CN$ (0.035% TFA)/$H_2O$ (0.05% TFA)) gave (R)-neopentyl 1-(6-fluoro-2-(2-hydroxyphenyl)quinazolin-4-yl)pyrrolidin-3-ylcarbamate (compound 4) as the TFA salt. LC/MS: m/z 439.5 $(M+H)^+$ at 2.87 min (10%-99% $CH_3CN$ (0.035% TFA)/$H_2O$ (0.05% TFA)).

Example 6

(R)-Isobutyl 1-(2-(2-hydroxyphenyl)-7-methylquinazolin-4-yl)pyrrolidin-3-ylcarbamate (compound 5)

(R)-Isobutyl 1-(2-(2-hydroxyphenyl)-7-methylquinazolin-4-yl)pyrrolidin-3-ylcarbamate (compound 5)

Method A.

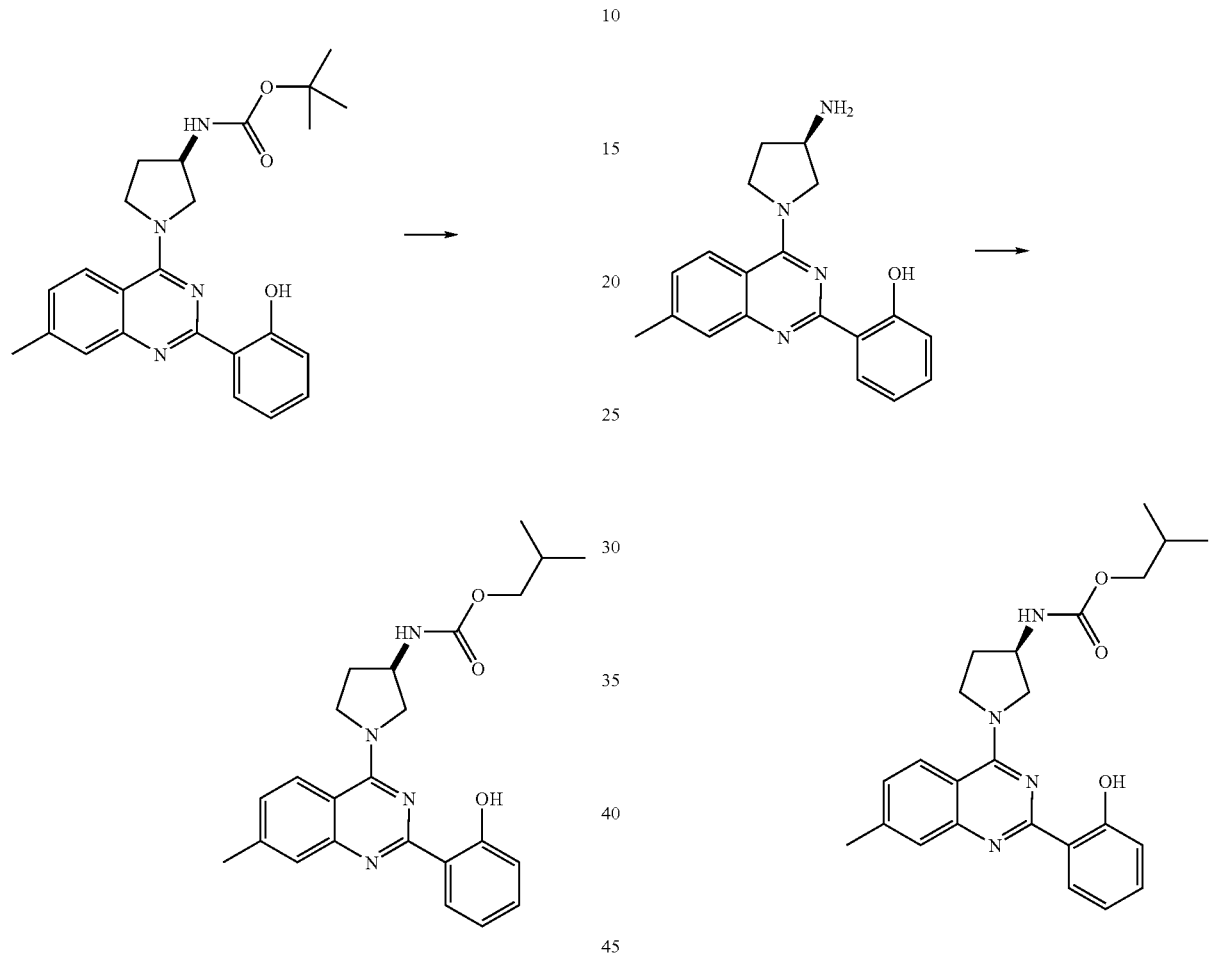

To (R)-{1-[2-(2-hydroxy-phenyl)-7-methyl-quinazolin-4-yl]-pyrrolidin-3-yl}-carbamic acid tert-butyl ester (1.54 g, 3.67 mmol) at room temperature was added 10 mL of a 1:1 TFA:CH$_2$Cl$_2$ solution. The reaction mixture was stirred for 30 min and diluted with 10 mL of saturated NaHCO$_3$ and 15 mL of CH$_2$Cl$_2$. The resulting emulsion was filtered, and the organic layer was separated and dried over Na$_2$SO$_4$. The solvent was removed under reduced pressure to give (R)-2-[4-(3-amino-pyrrolidin-1-yl)-7-methyl-quinazolin-2-yl]-phenol. LC/MS: m/z 321.2 (M+H)$^+$ at 1.91 min (10%-99% CH$_3$CN (0.035% TFA)/H$_2$O (0.05% TFA)).

To (R)-2-[4-(3-amino-pyrrolidin-1-yl)-7-methyl-quinazolin-2-yl]-phenol (52.3 mg, 0.16 mmol) in 500 μL of DMF at 0° C. was added sequentially isobutyl chloroformate (21.4 mg, 0.16 mmol) and 23 μL of triethylamine. The reaction mixture was stirred for 25 min and diluted with water and CH$_2$Cl$_2$. The organic layer was separated, dried over Na$_2$SO$_4$, and solvent removed under reduced pressure to give an oil which was purified via reverse phase HPLC (10%-99% CH$_3$CN (0.035% TFA)/H$_2$O (0.05% TFA)) to give (R)-isobutyl 1-(2-(2-hydroxyphenyl)-7-methylquinazolin-4-yl)pyrrolidin-3-ylcarbamate (compound 5) as the TFA salt. LC/MS: m/z 421 (M+H)$^+$ at 2.83 min (10%-99% CH$_3$CN (0.035% TFA)/H$_2$O (0.05% TFA)).

Method B.

Under an N$_2$ atmosphere, triethylamine (0.35 mL, 2.5 mmol) was added to a solution of (R)-2-(4-(3-aminopyrrolidin-1-yl)-7-methylquinazolin-2-yl)phenol (0.40 g, 1.25 mmol) in DMF (6.0 mL). The reaction mixture was cooled to −20° C. external temperature, and isobutyl chloroformate (180 μL, 1.38 mmol) was added dropwise. The reaction was stirred for 10 minutes at −20° C. and 15 minutes at RT. The mixture was quenched with H$_2$O, and partitioned between CH$_2$Cl$_2$ and H$_2$O, and the aqueous layer was extracted once more with CH$_2$Cl$_2$. The organic phase was dried over Na$_2$SO$_4$, filtered and purified via silica gel chromatography using 6% EtOAc in a 1:1 mixture of hexanes and CH$_2$Cl$_2$ to yield (R)-isobutyl 1-(2-(2-hydroxyphenyl)-7-methylquinazolin-4-yl)pyrrolidin-3-ylcarbamate (compound 5) (306 mg, 58%). $^1$H NMR (400 MHz, DMSO-d6) δ 8.43 (m, 1H), 8.18 (d, J=8.6 Hz, 1H), 7.59 (s, 2H), 7.35 (m, 2H), 6.92 (m, 2H), 4.06 (m, 5H), 3.75 (d, J=4.4 Hz, 2H), 2.49 (s, 3H), 2.23 (m, 1H), 2.03 (m, 1H), 1.83 (m, 1H), 0.87 (d, J=6.5 Hz, 6H) ppm. LC/MS: m/z 421.3 (M+H)$^+$ at 2.54 min (10%-99% CH$_3$CN (0.035% TFA)/H$_2$O (0.05% TFA)).

83

(R)-Isobutyl 1-(2-(2-hydroxyphenyl)-7-methylquinazolin-4-yl)pyrrolidin-3-ylcarbamate hydrochloride (HCl salt of compound 5)

84

(R)-Isobutyl 1-(2-(2-hydroxyphenyl)-7-methylquinazolin-4-yl)pyrrolidin-3-ylcarbamate sulfate (H₂SO₄ salt of compound 5)

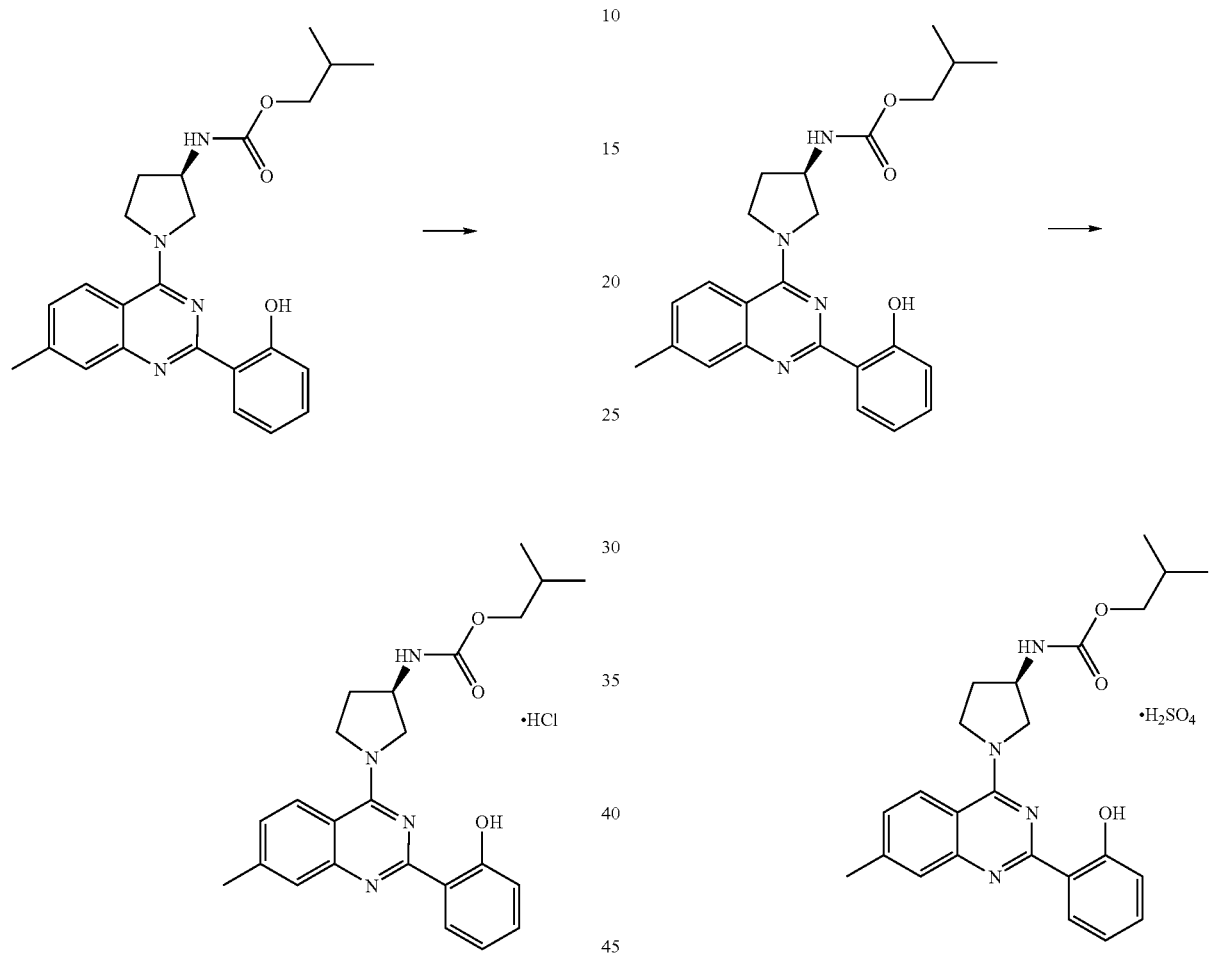

Under an $N_2$ atmosphere, anhydrous ether (12 mL) was added to a solution of (R)-isobutyl 1-(2-(2-hydroxyphenyl)-7-methylquinazolin-4-yl)pyrrolidin-3-ylcarbamate (306 mg, 0.73 mmol). A 2.0 M HCl solution in ether (0.365 mL, 0.73 mmol) was added over a period of 45 seconds, upon which a precipitate formed. The reaction was stirred for 10 additional minutes, before the solid was obtained by vacuum filtration and dried under high vacuum to give (R)-isobutyl 1-(2-(2-hydroxyphenyl)-7-methylquinazolin-4-yl)pyrrolidin-3-ylcarbamate hydrochloride (HCl salt of compound 5) (300 mg, 90%). $^1$H NMR (400 MHz, acetic acid-d4) δ 8.28 (d, J=8.3 Hz, 1H), 8.20 (m, 1H), 7.75 (s, 1H), 7.53 (m, 2H), 7.08 (m, 2H), 4.00 (m, 7H), 2.54 (s, 3H), 2.27 (m, 1H), 2.01 (m, 1H), 1.82 (m, 1H), 0.87 (d, J=6.5 Hz, 6H) ppm. LC/MS: m/z 421.0 (M+H)$^+$ at 2.54 min (10%-99% CH$_3$CN (0.035% TFA)/H$_2$O (0.05% TFA)).

A 0.5 M solution of H$_2$SO$_4$ in acetonitrile (2.38 mL) was added to a solution of ((R)-isobutyl 1-(2-(2-hydroxyphenyl)-7-methylquinazolin-4-yl)pyrrolidin-3-ylcarbamate (0.5 g, 1.19 mmol) in dry THF (2.0 mL), and the reaction was stirred at RT for 2 h. The formed gelatinous white slurry was filtered, washed with THF, and dried under vacuum to give (R)-isobutyl 1-(2-(2-hydroxyphenyl)-7-methylquinazolin-4-yl)pyrrolidin-3-ylcarbamate sulfate as a yellow solid. $^1$H NMR (400 MHz, DMSO-d6) δ 8.29 (d, J=8.2 Hz, 1H), 8.15 (d, J=7.1 Hz, 1H), 7.76 (s, 1H), 7.61 (s, 1H), 7.55-7.51 (m, 2H), 7.12-7.04 (m, 2H), 4.40-4.02 (m, 4H), 3.98 (d, J=9.0 Hz, 1H), 3.84-3.75 (m, 2H), 2.54 (s, 3H), 2.27-2.22 (m, 1H), 2.10-2.08 (m, 1H), 1.98-1.79 (m, 1H), 0.88 (d, J=6.4 Hz, 6H) ppm. LC/MS: m/z 421.1 (M+H)$^+$ at 2.71 min (10%-99% CH$_3$CN (0.035% TFA)/H$_2$O (0.05% TFA)).

Example 7

(S)-{1-[2-(2-Hydroxy-phenyl)-7-methyl-quinazolin-4-yl]-pyrrolidin-3-yl}-carbamic acid 2-methoxy-ethyl ester (compound 6)

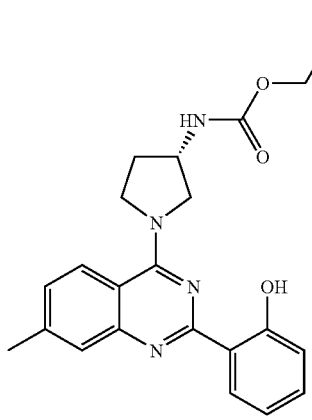

(S)-{1-[2-(2-Hydroxy-phenyl)-7-methyl-quinazolin-4-yl]-pyrrolidin-3-yl}-carbamic acid tert-butyl ester

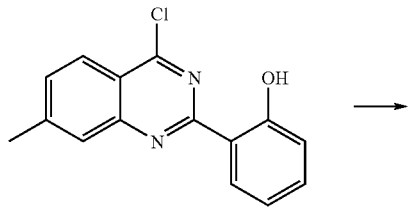

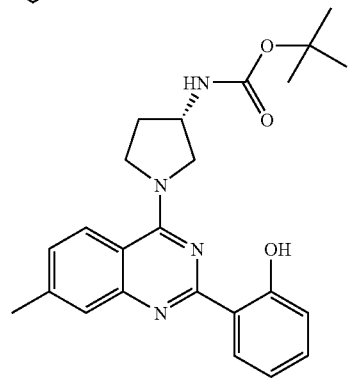

To 2-(4-chloro-7-methyl-quinazolin-2-yl)-phenol (300 mg, 1.1 mmol) in 1.8 mL of CH$_2$Cl$_2$ at 0° C. was added (S)-pyrrolidin-3-yl-carbamic acid tert-butyl ester (246 mg, 1.32 mmol) in 1.8 mL of CH$_2$Cl$_2$, followed by triethylamine (184 μL, 1.32 mmol). The reaction mixture was stirred from 0° C. to room temperature over 16 h. The reaction mixture was diluted with 10 mL of CH$_2$Cl$_2$ and 10 mL of water, and the organic layer was separated and dried over Na$_2$SO$_4$. The solvent was removed under reduced pressure, and the residue was purified via silica gel chromatography using 10-100% EtOAc in hexanes to give of (S)-{1-[2-(2-hydroxy-phenyl)-7-methyl-quinazolin-4-yl]-pyrrolidin-3-yl}-carbamic acid tert-butyl ester (352 mg, 70%). LC/MS: m/z 421 (M+H)$^+$ at 2.84 min (10%-99% CH$_3$CN (0.035% TFA)/H$_2$O (0.05% TFA)).

(S)-{1-[2-(2-Hydroxy-phenyl)-7-methyl-quinazolin-4-yl]-pyrrolidin-3-yl}-carbamic acid 2-methoxy-ethyl ester (compound 6)

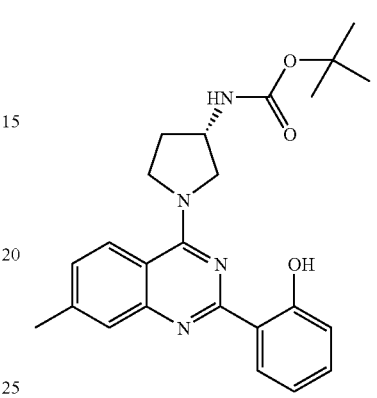

To (S)-{1-[2-(2-hydroxy-phenyl)-7-methyl-quinazolin-4-yl]-pyrrolidin-3-yl}-carbamic acid tert-butyl ester (174 mg, 0.41 mmol) at room temperature was added 1.4 mL of a 1:1 TFA:CH$_2$Cl$_2$ solution. The reaction mixture was stirred for 30 min and diluted with 10 mL of saturated NaHCO$_3$ and 10 mL of CH$_2$Cl$_2$. The organic layer was separated and dried over Na$_2$SO$_4$. The solvent was removed under reduced pressure to give (S)-2-[4-(3-amino-pyrrolidin-1-yl)-7-methyl-quinazolin-2-yl]-phenol. LC/MS: m/z 321.2 (M+H)$^+$ at 1.89 min (10%-99% CH$_3$CN (0.035% TFA)/H$_2$O (0.05% TFA)) which was used for the next step.

To (S)-2-[4-(3-amino-pyrrolidin-1-yl)-7-methyl-quinazolin-2-yl]-phenol (50 mg, 0.16 mmol) in 600 μL of DMF at 0° C. was added sequentially (2-methoxy-ethyl) chloroformate (21.6 mg, 0.16 mmol) and triethylamine (26 μL, 0.19 mmol). The reaction mixture was stirred for 25 min and diluted with water and CH$_2$Cl$_2$. The organic layer was separated, dried over Na$_2$SO$_4$, and concentrated under reduced pressure to give an oil which was purified via reverse phase HPLC (10%-99% CH$_3$CN (0.035% TFA)/H$_2$O (0.05% TFA)) to give (S)-{1-[2-(2-hydroxy-phenyl)-7-methyl-quinazolin-4-yl]-pyrrolidin-3-yl}-carbamic acid 2-methoxy-ethyl ester (compound 6) as the TFA salt. LC/MS: m/z 423.3 (M+H)$^+$ at 2.54 min (10%-99% CH$_3$CN (0.035% TFA)/H$_2$O (0.05% TFA)).

Example 8

(S)-{1-[2-(2-Hydroxy-phenyl)-7-methyl-quinazolin-4-yl]-pyrrolidin-3-yl}-carbamic acid isobutyl ester (compound 7)

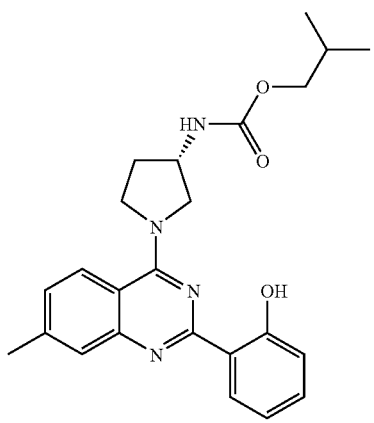

(S)-{1-[2-(2-Hydroxy-phenyl)-7-methyl-quinazolin-4-yl]-pyrrolidin-3-yl}-carbamic acid isobutyl ester (compound 7)

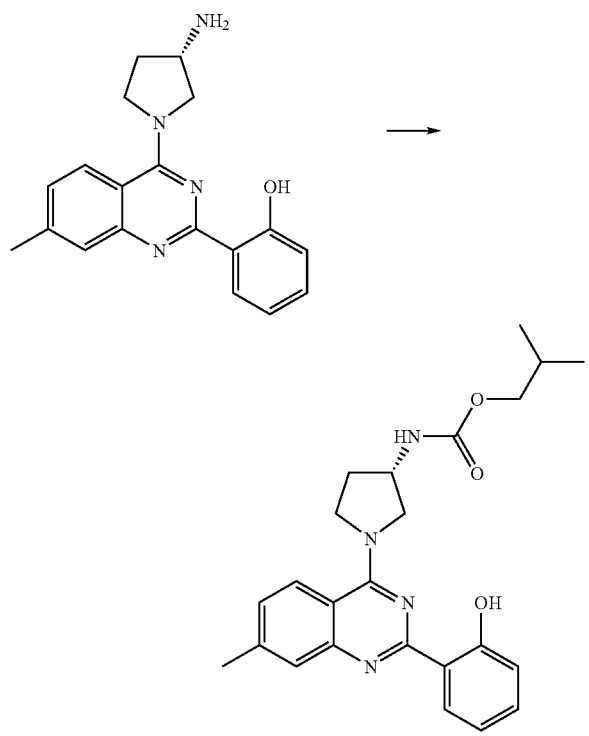

To (S)-2-[4-(3-amino-pyrrolidin-1-yl)-7-methyl-quinazolin-2-yl]-phenol (48 mg, 0.15 mmol) in 600 μL of CH$_2$Cl$_2$ at −50° C. was added sequentially iso-butyl chloroformate (20 mg, 0.15 mmol) and triethylamine (21 μL, 0.15 mmol). The reaction mixture was stirred for 15 min and diluted with saturated NaHCO$_3$ and CH$_2$Cl$_2$. The organic layer was separated, dried over Na$_2$SO$_4$, and concentrated under reduced pressure to give an oil which was purified via reverse phase HPLC (10%-99% CH$_3$CN (0.035% TFA)/H$_2$O (0.05% TFA)) to give (S)-{1-[2-(2-hydroxy-phenyl)-7-methyl-quinazolin-4-yl]-pyrrolidin-3-yl}-carbarnic acid isobutyl ester (compound 7) as the TFA salt. LC/MS: m/z 421 (M+H)$^+$ at 2.83 min (10%-99% CH$_3$CN (0.035% TFA)/H$_2$O (0.05% TFA)).

Example 9

(R)-Isobutyl 1-(2-(2-fluoro-6-hydroxyphenyl)-7-methylquinazolin-4-yl)pyrrolidin-3-ylcarbamate (compound 8)

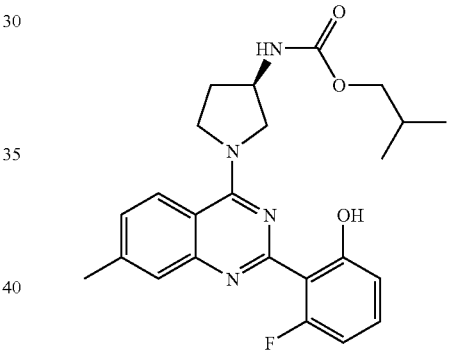

(R)-Isobutyl 1-(2-(2-fluoro-6-hydroxyphenyl)-7-methylquinazolin-4-yl)pyrrolidin-3-ylcarbamate (compound 8)

At 0° C., isobutyl chloroformate (17 μL, 0.13 mmol) was added to a stirring mixture of (R)-2-(4-(3-aminopyrrolidin-1-yl)-7-methylquinazolin-2-yl)-3-fluorophenol (40 mg, 0.12 mmol), triethylamine (33 μL, 0.24 mmol), and DMF (0.8 mL). After allowing the reaction to warm to RT, the mixture was diluted with saturated NaHCO$_3$ and CH$_2$Cl$_2$. The organic layer was separated, dried over Na$_2$SO$_4$ and concentrated under reduced pressure to give an oil which was purified via reverse phase HPLC (10%-99% CH$_3$CN (0.035% TFA)/H$_2$O (0.05% TFA)) which gave (R)-isobutyl 1-(2-(2-fluoro-6-hydroxyphenyl)-7-methylquinazolin-4-yl)pyrrolidin-3-ylcarbamate (compound 8) as the TFA salt. LC/MS: m/z 439.5 (M+H)$^+$ at 2.41 min (10%-99% CH$_3$CN (0.035% TFA)/H$_2$O (0.05% TFA)).

Example 10

(R)-Neopentyl 1-(2-(2-hydroxyphenyl)-7-methylquinazolin-4-yl)pyrrolidin-3-ylcarbamate (compound 9)

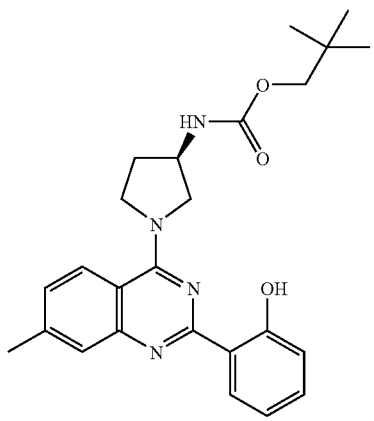

(R)-Neopentyl 1-(2-(2-hydroxyphenyl)-7-methylquinazolin-4-yl)pyrrolidin-3-ylcarbamate (compound 9)

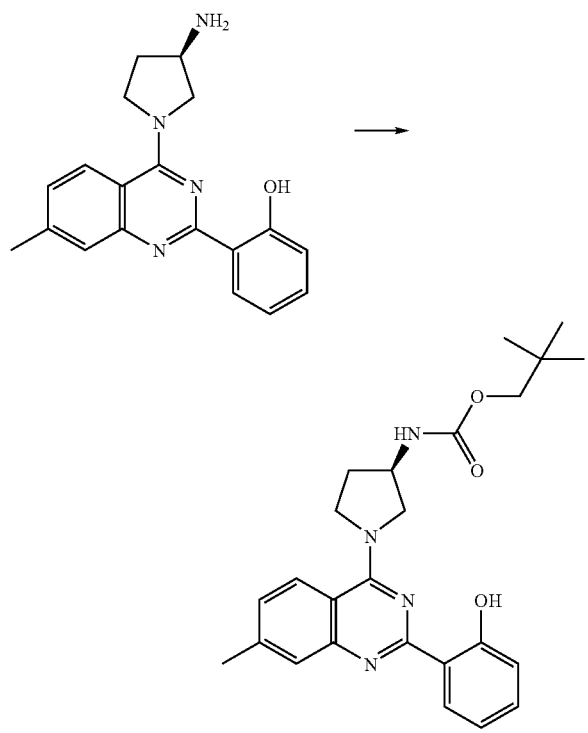

Method A. At −50° C., neopentyl chloroformate (19 µL, 0.12 mmol) was added rapidly to a solution of (R)-2-(4-(3-aminopyrrolidin-1-yl)-7-methylquinazolin-2-yl)phenol (40 mg, 0.12 mmol) and triethylamine (34 µL, 0.24 mmol) in DMF (0.8 mL). The reaction was warmed to RT over a period of 1 h. Purification via reverse phase HPLC (10%-99% CH$_3$CN (0.035% TFA)/H$_2$O (0.05% TFA)) gave (R)-neopentyl 1-(2-(2-hydroxyphenyl)-7-methylquinazolin-4-yl)pyrrolidin-3-ylcarbamate (compound 9) as the TFA salt. LC/MS: m/z 435.5 (M+H)$^+$ at 2.69 min (10%-99% CH$_3$CN (0.035% TFA)/H$_2$O (0.05% TFA)).

Method B. At RT, triethylamine (260 µL, 1.86 mmol) was added to a solution of (R)-2-(4-(3-aminopyrrolidin-1-yl)-7-methylquinazolin-2-yl)phenol (300 mg, 0.93 mmol) in THF (6 mL), and the reaction was cooled to 40° C. external temperature. Neopentyl chloroformate (132 µL in 1.0 mL THF, 0.89 mmol) was added dropwise over a period of 5 minutes. Once the addition of the chloroformate was complete, the reaction mixture was warmed to RT, quenched with H$_2$O, and extracted with CH$_2$Cl$_2$. The organic phase was dried over MgSO$_4$, filtered, and concentrated. The residue was purified via silica gel chromatography using 0-10% EtOAc in CH$_2$Cl$_2$ to give (R)-neopentyl 1-(2-(2-hydroxyphenyl)-7-methylquinazolin-4-yl)pyrrolidin-3-ylcarbamate (compound 9) (345 mg, 85%). $^1$H NMR (400 MHz, DMSO-d6) δ 8.44-8.42 (m, 1H), 8.18 (d, J=8.6 Hz, 1H), 7.59 (d, J=0.5 Hz, 2H), 7.38-7.32 (m, 2H), 6.94-6.90 (m, 2H), 4.28-4.19 (m, 3H), 4.12-4.01 (m, 1H), 3.89 (d, J=9.0 Hz, 1H), 3.71-3.64 (m, 2H), 2.49 (s, 3H), 2.25-2.20 (m, 1H), 2.06-2.00 (m, 1H), 0.89 (s, 9H) ppm. LC/MS: m/z 435.5 (M+H)$^+$ at 2.73 min (10%-99% CH$_3$CN (0.035% TFA)/H$_2$O (0.05% TFA)).

(R)-Neopentyl 1-(2-(2-hydroxyphenyl)-7-methylquinazolin-4-yl)pyrrolidin-3-ylcarbamate hydrochloride (HCl salt of compound 9)

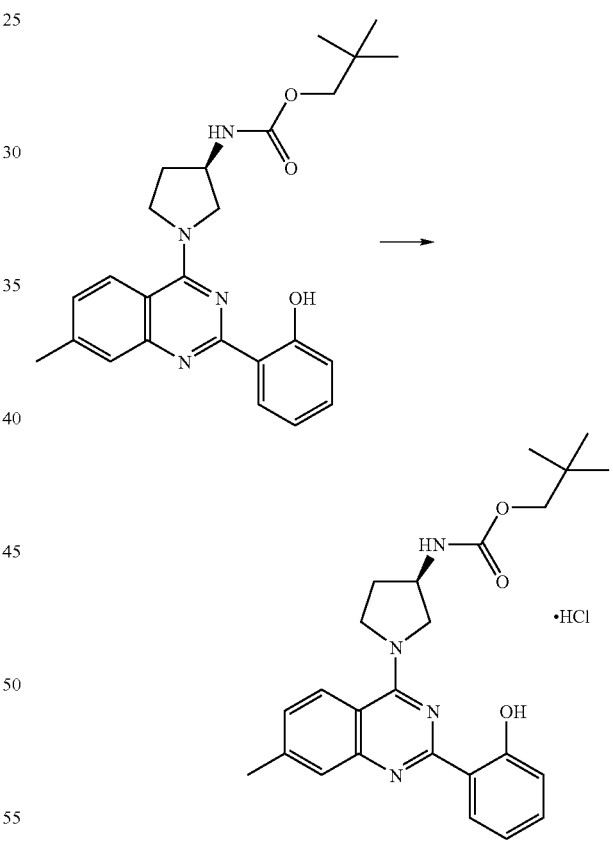

To a solution of (R)-neopentyl 1-(2-(2-hydroxyphenyl)-7-methylquinazolin-4-yl)pyrrolidin-3-ylcarbamate (343 mg, 0.79 mmol) in CH$_2$Cl$_2$ (3 mL) was added a 2.0 M solution of HCl in ether (0.395 mL, 0.79 mmol). After the addition of ether (12 mL), a precipitate formed, and the mixture was stirred for 30 minutes. The solid was filtered and dried under vacuum to give (R)-neopentyl 1-(2-(2-hydroxyphenyl)-7-methylquinazolin-4-yl)pyrrolidin-3-ylcarbamate hydrochloride (HCl salt of compound 9) (325 mg, 87%). $^1$H NMR (400 MHz, DMSO-d6) δ 8.27 (t, J=8.5 Hz, 2H), 7.75 (s, 1H), 7.61

(d, J=5.4 Hz, 1H), 7.51-7.47 (m, 2H), 7.09-7.01 (m, 2H), 4.29 (d, J=4.8 Hz, 2H), 4.14-3.82 (m, 3H), 3.72-3.62 (m, 2H, broad due to water), 2.53 (s, 3H), 2.25 (d, J=5.7 Hz, 1H), 2.08 (d, J=5.3 Hz, 1H), 0.89 (s, 9H) ppm. LC/MS: m/z 435.5 (M+H)$^+$ at 2.66 min (10%-99% CH$_3$CN (0.035% TFA)/H$_2$O (0.05% TFA)).

Example 11

(R)-Ethyl 1-(2-(2-fluoro-6-hydroxyphenyl)-7-methylquinazolin-4-yl)pyrrolidin-3-ylcarbamate (compound 10)

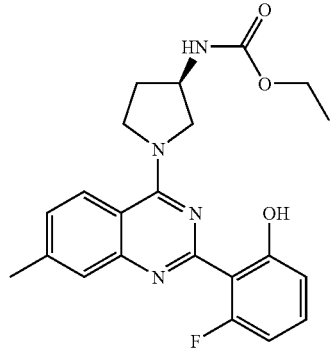

(R)-Ethyl 1-(2-(2-fluoro-6-hydroxyphenyl)-7-methylquinazolin-4-yl)pyrrolidin-3-ylcarbamate (compound 10)

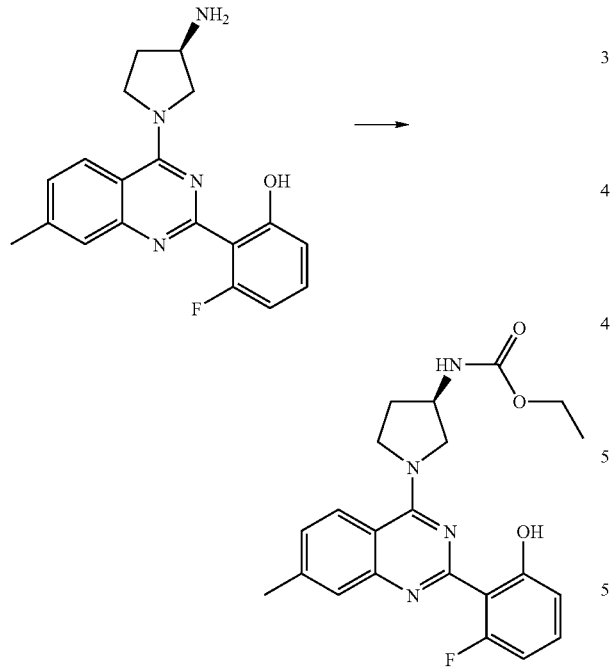

Method A. At 0° C., ethyl chloroformate (12 μL, 0.13 mmol) was added to a stirring mixture of (R)-2-(4-(3-aminopyrrolidin-1-yl)-7-methylquinazolin-2-yl)-3-fluorophenol (40 mg, 0.12 mmol), triethylamine (33 μL, 0.24 mmol), and DMF (0.8 μL). After allowing the reaction to warm to RT, purification via reverse phase HPLC (10%-99% CH$_3$CN (0.035% TFA)/H$_2$O (0.05% TFA)) gave (R)-ethyl 1-(2-(2-fluoro-6-hydroxyphenyl)-7-methylquinazolin-4-yl)pyrrolidin-3-ylcarbamate (compound 10) as the TFA salt. LC/MS: m/z 411.3 (M+H)$^+$ at 2.15 min (10%-99% CH$_3$CN (0.035% TFA)/H$_2$O (0.05% TFA)).

Method B. At RT, diisopropyl ethylamine (130 μL, 0.74 mmol) was added to a solution of (R)-2-(4-(3-aminopyrrolidin-1-yl)-7-methylquinazolin-2-yl)-3-fluorophenol (125 mg, 0.37 mmol) in THF (10 mL), and the reaction was cooled to −40° C. Ethyl chloroformate (33 μL in 0.33 mL THF, 0.34 mmol) was added dropwise over a period of 10 minutes. After addition of the chloroformate was complete, the reaction mixture was warmed to RT, quenched with H$_2$O, and extracted with CH$_2$Cl$_2$. The organic phase was dried over MgSO$_4$, filtered, and concentrated. The residue was purified via silica gel chromatography using 0-10% EtOAc in a 1:1 mixture of hexanes and CH$_2$Cl$_2$ to give (R)-ethyl 1-(2-(2-fluoro-6-hydroxyphenyl)-7-methylquinazolin-4-yl)pyrrolidin-3-ylcarbamate (compound 10) (130 mg, 85%). $^1$H NMR (400 MHz, DMSO-d6) δ 8.19 (d, J=8.6 Hz, 1H), 7.58-7.57 (m, 2H), 7.38-7.29 (m, 2H), 6.76 (d, J=8.3 Hz, 1H), 6.72-6.67 (m, 1H), 4.25-4.21 (m, 1H), 4.16-4.13 (m, 2H), 4.07-3.97 (m, 3H), 3.84-3.82 (m, 1H), 2.52 (s, 3H), 2.24-2.16 (m, 1H), 2.04-2.00 (m, 1H), 1.16 (t, J=7.1 Hz, 3H) ppm. LC/MS: m/z 411.3 (M+H)$^+$ at 2.24 min (10%-99% CH$_3$CN (0.035% TFA)/H$_2$O (0.05% TFA)).

(R)-Ethyl 1-(2-(2-fluoro-6-hydroxyphenyl)-7-methylquinazolin-4-yl)pyrrolidin-3-ylcarbamate hydrochloride (HCl salt of compound 10)

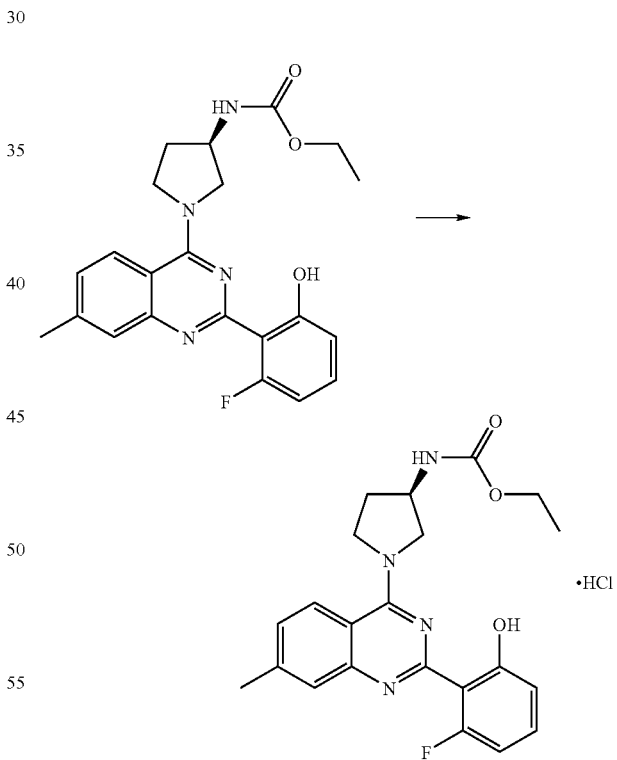

To a solution of (R)-ethyl 1-(2-(2-fluoro-6-hydroxyphenyl)-7-methylquinazolin-4-yl)pyrrolidin-3-ylcarbamate (129 mg, 0.31 mmol) in CH$_2$Cl$_2$ (10 mL) was added a 2.0 M solution of HCl in ether (0.155 mL). After the addition of ether (28 mL), a precipitate formed, and the mixture was stirred for 30 minutes. The solid was filtered and dried under high vacuum to give (R)-ethyl 1-(2-(2-fluoro-6-hydroxyphenyl)-7-methylquinazolin-4-yl)pyrrolidin-3-ylcarbamate hydrochloride (HCl salt of compound 10) (140 mg, 100%). ¹H NMR (400 MHz, DMSO-d6) δ 8.36 (s, 1H), 7.64-7.58 (m, 3H), 7.47 (q, J=7.8 Hz, 1H), 6.96 (d, J=8.3 Hz, 1H), 6.87 (t, J=9.1 Hz, 1H), 4.26 (s, 2H), 4.03-3.98 (m, 4H), 3.38-3.36 (m, 1H, broad due to water), 2.56 (s, 3H), 2.23 (s, 1H), 2.04 (s, 1H), 1.16 (t, J=7.1 Hz, 3H) ppm. LC/MS: m/z 411.1 (M+H)⁺ at 2.25 min (10%-99% CH₃CN (0.035% TFA)/H₂O (0.05% TFA)).

Example 12

(R)-Neopentyl 1-(2-(2-fluoro-6-hydroxyphenyl)-7-methylquinazolin-4-yl)pyrrolidin-3-ylcarbamate (compound 11)

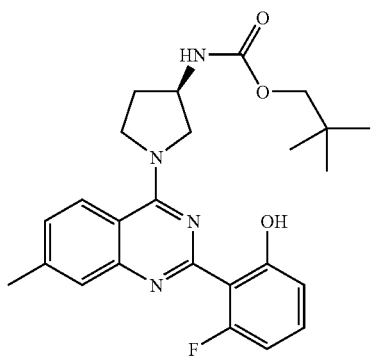

(R)-Neopentyl 1-(2-(2-fluoro-6-hydroxyphenyl)-7-methylquinazolin-4-yl)pyrrolidin-3-ylcarbamate (compound 11)

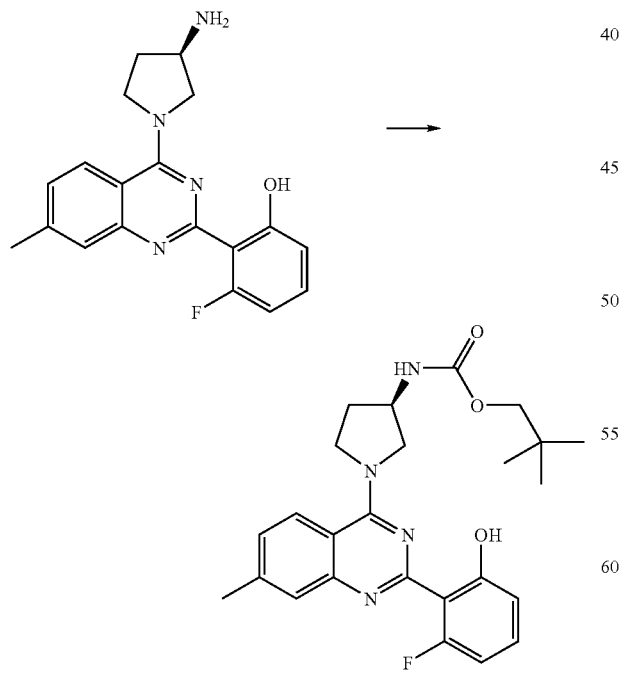

Method A. At 0° C., neopentyl chloroformate (19 μL, 0.13 mmol) was added to a stirring mixture of (R)-2-(4-(3-aminopyrrolidin-1-yl)-7-methylquinazolin-2-yl)-3-fluorophenol (40 mg, 0.12 mmol), triethylamine (33 μL, 0.24 mmol), and DMF (0.8 mL). After allowing the reaction to warm to RT, purification via reverse phase HPLC (10%-99% CH₃CN (0.035% TFA)/H₂O (0.05% TFA)) gave (R)-neopentyl 1-(2-(2-fluoro-6-hydroxyphenyl)-7-methylquinazolin-4-yl)pyrrolidin-3-ylcarbamate (compound 11) as the TFA salt. LC/MS: m/z 453.3 (M+H)⁺ at 2.53 min (10%-99% CH₃CN (0.035% TFA)/H₂O (0.05% TFA)).

Method B. At RT, diisopropyl ethylamine (273 μL, 1.57 mmol) was added to a solution of (R)-2-(4-(3-aminopyrrolidin-1-yl)-7-methylquinazolin-2-yl)-3-fluorophenol (266 mg, 0.79 mmol) in THF (15 mL), and the reaction was cooled to −60° C. Neopentyl chloroformate (116 μL in 2.0 μL THF, 0.79 mmol) was added dropwise over a period of 10 minutes. After addition of the chloroformate was complete, the reaction mixture was warmed to RT, quenched with H₂O, and extracted with CH₂Cl₂. The organic phase was dried over MgSO₄, filtered, and concentrated. The residue was purified via silica gel chromatography using 0-10% EtOAc in a 1:1 mixture of hexanes and CH₂Cl₂ to give (R)-neopentyl 1-(2-(2-fluoro-6-hydroxyphenyl)-7-methylquinazolin-4-yl)pyrrolidin-3-ylcarbamate (compound 11) (340 mg, 94%). ¹H NMR (400 MHz, DMSO-d6) δ 8.37 (s, 1H), 7.64-7.58 (m, 3H), 7.47 (q, J=7.8 Hz, 1H), 6.95 (d, J=8.3 Hz, 1H), 6.87 (t, J=9.2 Hz, 1H), 4.28-3.99 (m, 5H), 3.71-3.64 (m, 2H), 2.56 (s, 3H), 2.23-2.14 (m, 1H), 2.07-1.92 (m, 1H), 0.89 (s, 9H) ppm. LC/MS: m/z 453.5 (M+H)⁺ at 2.66 min (10%-99% CH₃CN (0.035% TFA)/H₂O (0.05% TFA)).

(R)-Neopentyl 1-(2-(2-fluoro-6-hydroxyphenyl)-7-methylquinazolin-4-yl)pyrrolidin-3-ylcarbamate hydrochloride (HCl salt of compound 11)

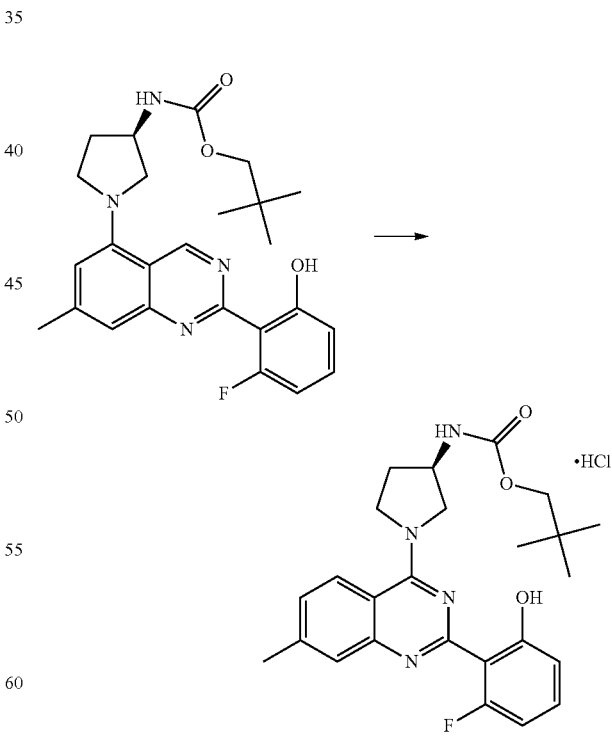

To a solution of (R)-neopentyl 1-(2-(2-fluoro-6-hydroxyphenyl)-7-methylquinazolin-4-yl)pyrrolidin-3-ylcarbamate (224 mg, 0.49 mmol) in CH₂Cl₂ (5 mL) was added a 2.0 M solution of HCl in ether (0.24 mL, 0.49 mmol). After the addition of ether (20 mL), a precipitate formed, which was filtered and dried under vacuum to give (R)-neopentyl 1-(2-(2-fluoro-6-hydroxyphenyl)-7-methylquinazolin-4-yl)pyrrolidin-3-ylcarbamate hydrochloride (HCl salt of compound 13) (225 mg, 94%). $^1$H NMR (400 MHz, DMSO-d6). LC/MS: m/z 453.3 (M+H)$^+$ at 2.73 min (10%-99% CH$_3$CN (0.035% TFA)/H$_2$O (0.05% TFA)).

Example 13

(R)-Isopropyl 1-(2-(2-hydroxyphenyl)-7-methylquinazolin-4-yl)pyrrolidin-3-ylcarbamate (compound 12)

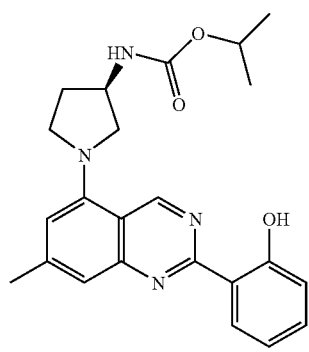

(R)-Isopropyl 1-(2-(2-hydroxyphenyl)-7-methylquinazolin-4-yl)pyrrolidin-3-ylcarbamate (compound 12)

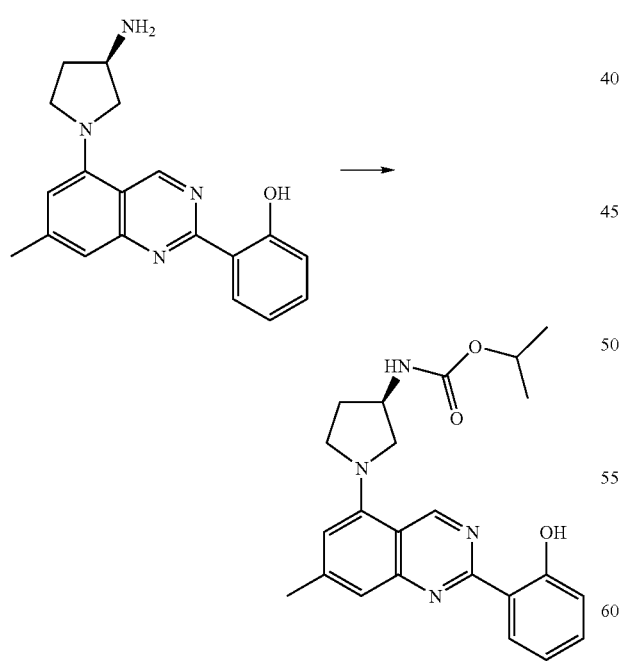

Method A. At −50° C., isopropyl chloroformate (17 μL, 0.12 mmol) was added rapidly to a solution of (R)-2-(4-(3-aminopyrrolidin-1-yl)-7-methylquinazolin-2-yl)phenol (40 mg, 0.12 mmol) and triethylamine (34 μL, 0.24 mmol) in DMF (0.8 mL). The reaction was warmed to RT over a period of 1 h. Purification via reverse phase HPLC (10%-99% CH$_3$CN (0.035% TFA)/H$_2$O (0.05% TFA)) gave (R)-isopropyl 1-(2-(2-hydroxyphenyl)-7-methylquinazolin-4-yl)pyrrolidin-3-ylcarbamate (compound 12) as the TFA salt. LC/MS: m/z 407.7 (M+H)$^+$ at 2.42 min (10%-99% CH$_3$CN (0.035% TFA)/H$_2$O (0.05% TFA)).

Method B. At RT under an N$_2$ atmosphere, triethylamine (23 mL, 0.31 mmol) was added to a solution of (R)-2-(4-(3-aminopyrrolidin-1-yl)-7-methylquinazolin-2-yl)phenol (50 mg, 0.16 mmol) in THF (1.5 mL), and the reaction was cooled to −70° C. A 1.0 M solution of isopropyl chloroformate in toluene (133 μL, 0.15 mmol) was added, and the mixture was warmed to RT. The reaction was quenched with H$_2$O and extracted with CH$_2$Cl$_2$. The combined organic extracts were washed twice with H$_2$O, dried over Na$_2$SO$_4$, and concentrated. Purification via silica gel chromatography using 0-20% EtOAc in a 1:1 mixture of CH$_2$Cl$_2$ and hexanes gave (R)-isopropyl 1-(2-(2-hydroxyphenyl)-7-methylquinazolin-4-yl)pyrrolidin-3-ylcarbamate (compound 12) (23 mg, 38%). $^1$H NMR (400 MHz, DMSO-d6) δ 8.42 (dd, J=8.1, 1.6 Hz, 1H), 8.17 (d, J=8.6 Hz, 1H), 7.59 (s, 1H), 7.52 (d, J=5.9 Hz, 1H), 7.38-7.32 (m, 2H), 6.94-6.90 (m, 2H), 4.81-4.74 (m, 1H), 4.25-4.11 (m, 3H), 4.06-4.01 (m, 1H), 3.85 (dd, J=11.1, 3.5 Hz, 1H), 2.49 (s, 3H), 2.25-2.17 (m, 1H), 2.05-1.99 (m, 1H), 1.20-1.15 (m, 6H) ppm. LC/MS: m/z 407.5 (M+H)$^+$ at 2.44 min (10%-99% CH$_3$CN (0.035% TFA)/H$_2$O (0.05% TFA)).

(R)-Isopropyl 1-(2-(2-hydroxyphenyl)-7-methylquinazolin-4-yl)pyrrolidin-3-ylcarbamate hydrochloride (HCl salt of compound 12)

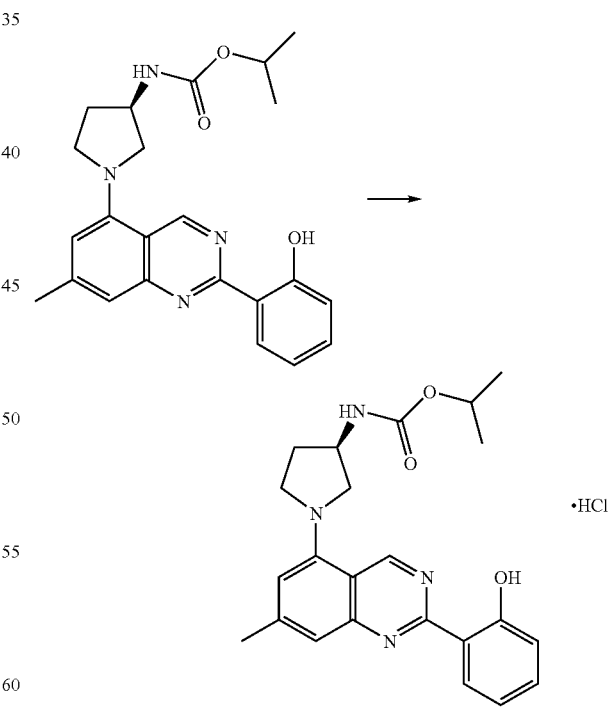

Under an N$_2$ atmosphere, a 2.0 M HCl solution in ether (0.30 mL, 0.60 mmol) was added to a solution of (R)-isopropyl 1-(2-(2-hydroxyphenyl)-7-methylquinazolin-4-yl)pyrrolidin-3-ylcarbamate (246 mg, 0.6 mmol) in a mixture of CH$_2$Cl$_2$ (10 mL) and MeOH (1 mL). After the addition of ether (15 mL), a precipitate formed, and the mixture was stirred for an additional 20 minutes. The solid was collected by vacuum filtration and dried to obtain (R)-isopropyl 1-(2-(2-hydroxyphenyl)-7-methylquinazolin-4-yl)pyrrolidin-3-ylcarbamate hydrochloride (HCl salt of compound 12) (215 mg, 80%). $^1$H NMR (400 MHz, DMSO-d6) δ 8.22 (d, J=8.1 Hz, 1H), 8.14 (dd, J=7.9, 1.4 Hz, 1H), 7.69 (s, 1H), 7.54-7.48 (m, 2H), 7.08-7.03 (m, 2H), 4.77-4.71 (m, 1H), 4.25-4.12 (m, 4H), 3.93-3.91 (m, 1H), 2.50 (s, 3H), 2.25-2.23 (m, 1H), 2.06-2.03 (m, 1H), 1.16-1.12 (m, 6H) ppm. LC/MS: m/z 407.5 (M+H)$^+$ at 2.43 min (10%-99% CH$_3$CN (0.035% TFA)/H$_2$O (0.05% TFA)).

Example 14

(R)-Propyl 1-(2-(2-fluoro-6-hydroxyphenyl)-7-methylquinazolin-4-yl)pyrrolidin-3-ylcarbamate (compound 13)

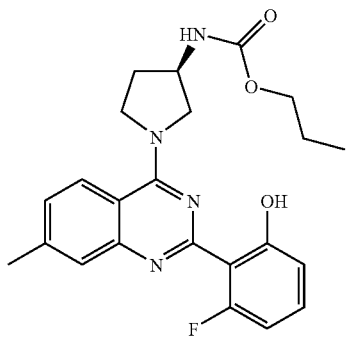

(R)-Propyl 1-(2-(2-fluoro-6-hydroxyphenyl)-7-methylquinazolin-4-yl)pyrrolidin-3-ylcarbamate (compound 13)

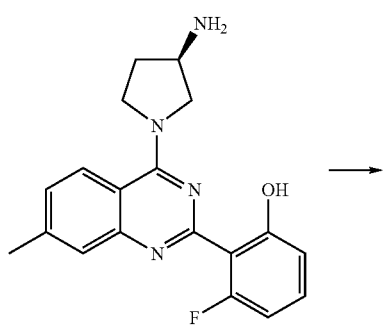

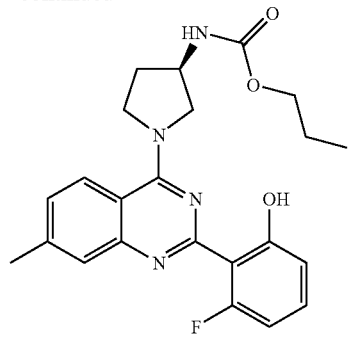

Method A. At 0° C., propyl chloroformate (15 μL, 0.13 mmol) was added to a stirring mixture of (R)-2-(4-(3-aminopyrrolidin-1-yl)-7-methylquinazolin-2-yl)-3-fluorophenol (40 mg, 0.12 mmol), triethylamine (33 μL, 0.24 mmol), and DMF (0.8 mL). After allowing the reaction to warm to RT, purification via reverse phase HPLC (10%-99% CH$_3$CN (0.035% TFA)/H$_2$O (0.05% TFA)) gave (R)-propyl 1-(2-(2-fluoro-6-hydroxyphenyl)-7-methylquinazolin-4-yl)pyrrolidin-3-ylcarbamate (compound 13) as the TFA salt. LC/MS: m/z 425.1 (M+H)$^+$ at 2.29 min (10%-99% CH$_3$CN (0.035% TFA)/H$_2$O (0.05% TFA)).

Method B. At RT, diisopropyl ethylamine (174 μL, 1 mmol) was added to a solution of (R)-2-(4-(3-aminopyrrolidin-1-yl)-7-methylquinazolin-2-yl)-3-fluorophenol (170 mg, 0.5 mmol) in THF (12 mL), and the reaction was cooled to −60° C. Propyl chloroformate (55 μL in 0.55 mL THF, 0.5 mmol) was added dropwise over a period of 10 minutes. After addition of the chloroformate was complete, the reaction mixture was warmed to RT, quenched with H$_2$O, and extracted with CH$_2$Cl$_2$. The organic phase was dried over MgSO$_4$, filtered, and concentrated. The residue was purified via silica gel chromatography using 0-10% EtOAc in a 1:1 mixture of hexanes and CH$_2$Cl$_2$ to give (R)-propyl 1-(2-(2-fluoro-6-hydroxyphenyl)-7-methylquinazolin-4-yl)pyrrolidin-3-ylcarbamate (compound 13) (196 mg, 92%). $^1$H NMR (400 MHz, DMSO-d6) δ 8.19 (d, J=8.6 Hz, 1H), 7.58 (s, 1H), 7.34 (m, 2H), 6.76 (d, J=8.2 Hz, 1H), 6.70 (m, 1H), 4.03 (m, 7H), 2.50 (s, 3H), 2.20 (m, 1H), 2.02 (m, 1H), 1.55 (m, 2H), 0.87 (t, J=7.4 Hz, 3H) ppm. LC/MS: m/z 425.5 (M+H)$^+$ at 2.38 min (10%-99% CH$_3$CN (0.035% TFA)/H$_2$O (0.05% TFA)).

(R)-Propyl 1-(2-(2-fluoro-6-hydroxyphenyl)-7-methylquinazolin-4-yl)pyrrolidin-3-ylcarbamate hydrochloride (HCl salt of compound 13)

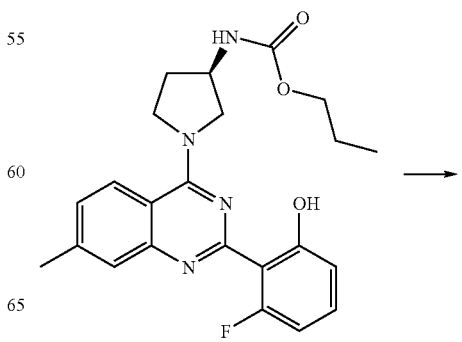

(R)-2-Methoxyethyl 1-(2-(2-hydroxyphenyl)-7-methylquinazolin-4-yl)pyrrolidin-3-ylcarbamate (compound 14)

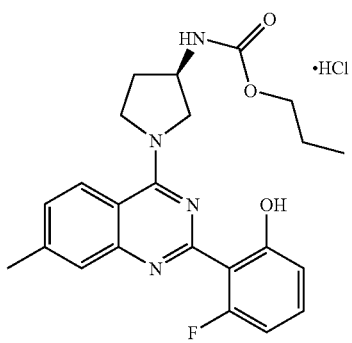

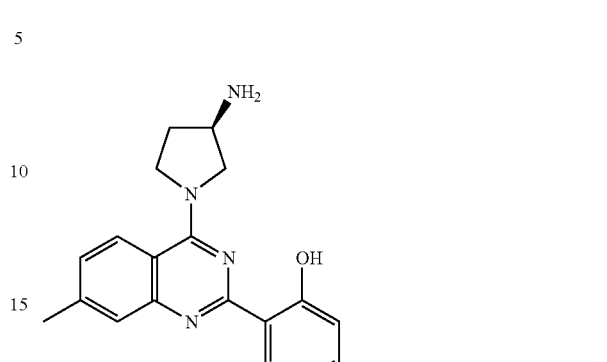

To a solution of (R)-propyl 1-(2-(2-fluoro-6-hydroxyphenyl)-7-methylquinazolin-4-yl)pyrrolidin-3-ylcarbamate (195 mg, 0.46 mmol) in CH$_2$Cl$_2$ (2 mL) was added a 2.0 M solution of HCl in ether (0.23 mL, 0.46 mmol). After the addition of ether (20 mL), a precipitate formed, and the mixture was stirred for 30 minutes. The solid was filtered and dried under vacuum to give (R)-propyl 1-(2-(2-fluoro-6-hydroxyphenyl)-7-methylquinazolin-4-yl)pyrrolidin-3-ylcarbamate hydrochloride (HCl salt of compound 13) (130 mg, 61%). $^1$H NMR (400 MHz, DMSO-d6) δ 8.36 (s, 1H), 7.63-7.58 (m, 3H), 7.47 (q, J=7.8 Hz, 1H), 6.94 (d, J=8.5 Hz, 1H), 6.87 (t, J=9.3 Hz, 3H), 4.26 (s, 1H), 3.93-3.91 (m, 4H), 2.56 (s, 3H), 2.23 (s, 1H), 2.05 (s, 1H), 1.58-1.53 (m, 2H), 0.88 (t, J=7.2 Hz, 3H) ppm. LC/MS: m/z 425.5 (M+H)$^+$ at 2.40 min (10%-99% CH$_3$CN (0.035% TFA)/H$_2$O (0.05% TFA)).

Example 15

(R)-2-Methoxyethyl 1-(2-(2-hydroxyphenyl)-7-methylquinazolin-4-yl)pyrrolidin-3-ylcarbamate (compound 14)

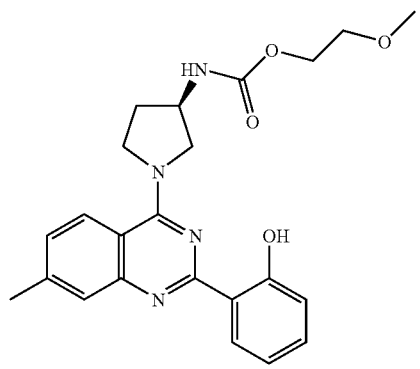

Method A. At –40° C., 2-methoxyethyl chloroformate (11 mg, 0.08 mmol) was added to a solution of (R)-2-(4-(3-aminopyrrolidin-1-yl)-7-methylquinazolin-2-yl)phenol (25 mg, 0.08 mmol) and triethylamine (21 µL, 0.16 mmol) in DMF (0.5 mL). After addition of the chloroformate was complete, the reaction was slowly warmed to RT. Purification via reverse phase HPLC (10%-99% CH$_3$CN (0.035% TFA)/H$_2$O (0.05% TFA)) gave (R)-2-methoxyethyl 1-(2-(2-hydroxyphenyl)-7-methylquinazolin-4-yl)pyrrolidin-3-ylcarbamate (compound 14) as the TFA salt. LC/MS: m/z 423.5 (M+H)$^+$ at 2.17 min (10%-99% CH$_3$CN (0.035% TFA)/H$_2$O (0.05% TFA)).

Method B. At RT, triethylamine (260 mL, 1.87 mmol) was added to a mixture of (R)-2-(4-(3-aminopyrrolidin-1-yl)-7-methylquinazolin-2-yl)phenol (300 mg, 0.94 mmol) in THF (9 mL). The mixture was cooled to –70° C. external temperature and 2-methoxyethyl chloroformate (0.1 mL, 0.89 mmol) was added dropwise. Once the addition of the chloroformate was complete, the reaction was quenched with H$_2$O, and extracted three times with CH$_2$Cl$_2$. The combined organic extracts were dried over MgSO$_4$, filtered, and concentrated. Purification via silica gel chromatography using 2-10% EtOAc in a 1:1 mixture of CH$_2$Cl$_2$ and hexanes gave (R)-2-methoxyethyl 1-(2-(2-hydroxyphenyl)-7-methylquinazolin-4-yl)pyrrolidin-3-ylcarbamate (compound 14) (205 mg, 52%). $^1$H NMR (400 MHz, DMSO-d6) δ 8.43-8.41 (m, 1H), 8.17 (d, J=8.6 Hz, 1H), 7.72 (d, J=6.0 Hz, 1H), 7.58 (s, 1H), 7.38-7.32 (m, 2H), 6.94-6.90 (m, 2H), 4.25-4.01 (m, 6H), 3.88-3.85 (m, 1H), 3.49-3.47 (m, 2H), 3.23 (s, 3H), 2.49 (s, 3H), 2.26-2.17 (m, 1H), 2.07-2.01 (m, 1H) ppm. LC/MS: m/z 423.3 (M+H)$^+$ at 2.20 min (10%-99% CH$_3$CN (0.035% TFA)/H$_2$O (0.05% TFA)).

101

(R)-2-Methoxyethyl 1-(2-(2-hydroxyphenyl)-7-methylquinazolin-4-yl)pyrrolidin-3-ylcarbamate hydrochloride (HCl salt of compound 14)

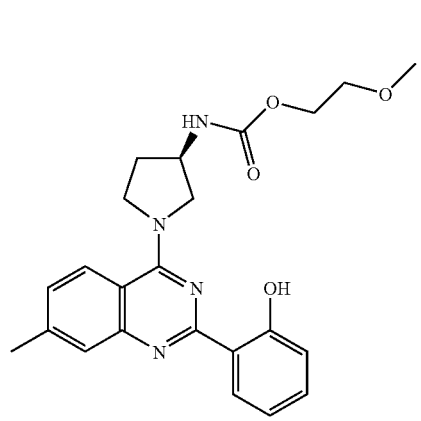

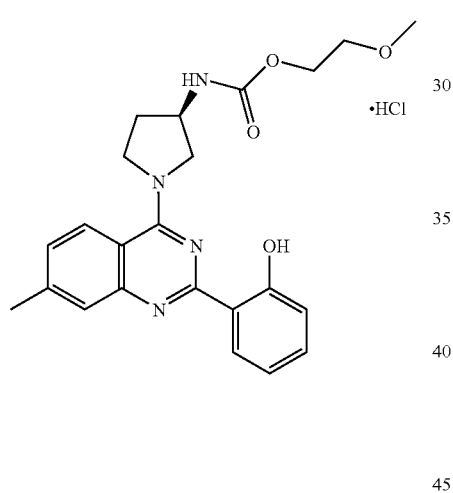

Under an N₂ atmosphere, ether (5 mL) was added to a solution of (R)-2-methoxyethyl 1-(2-(2-hydroxyphenyl)-7-methylquinazolin-4-yl)pyrrolidin-3-ylcarbamate (200 mg, 0.47 mmol) in CH$_2$Cl$_2$ (1 mL). A 2.0 M HCl solution in ether (0.236 mL, 0.47 mmol) was added, upon which a precipitate formed. Additional ether was added (5 mL), and the mixture was stirred for 30 minutes. The solid was filtered and dried under vacuum to obtain (R)-2-methoxyethyl 1-(2-(2-hydroxyphenyl)-7-methylquinazolin-4-yl)pyrrolidin-3-ylcarbamate hydrochloride (HCl salt of compound 14) (160 mg, 80%). $^1$H NMR (400 MHz, DMSO-d6) δ 8.29-8.24 (m, 2H), 7.82 (s, 1H), 7.75 (d, J=5.5 Hz, 1H), 7.53-7.49 (m, 2H), 7.14 (d, J=8.2 Hz, 1H), 7.06-7.02 (m, 1H), 4.29-3.95 (m, 7H, water in this region), 3.50-3.47 (m, 2H), 3.23 (s, 3H), 2.54 (s, 3H), 2.26-2.23 (m, 1H), 2.08-2.07 (m, 1H) ppm. LC/MS: m/z 423.3 (M+H)$^+$ at 2.22 min (10%-99% CH$_3$CN (0.035% TFA)/H$_2$O (0.05% TFA)).

102

Example 16

(R)-Isobutyl 1-(6-fluoro-2-(2-hydroxyphenyl)quinazolin-4-yl)pyrrolidin-3-ylcarbamate (compound 15)

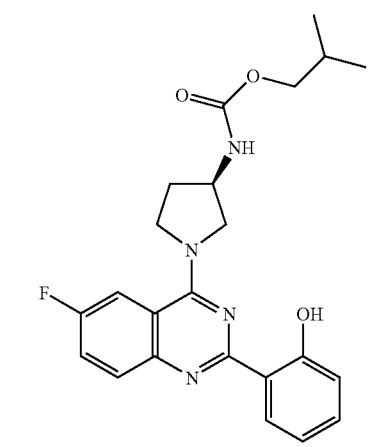

(R)-Isobutyl 1-(6-fluoro-2-(2-hydroxyphenyl)quinazolin-4-yl)pyrrolidin-3-ylcarbamate (compound 15)

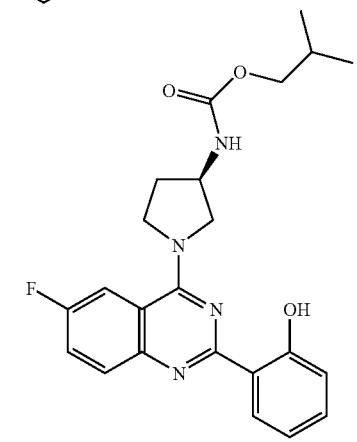

Method A. At −40° C., isobutyl chloroformate (11 mg, 0.08 mmol) was added to a solution of (R)-2-(4-(3-aminopyrrolidin-1-yl)-6-fluoroquinazolin-2-yl)phenol (25 mg, 0.08 mmol) and triethylamine (22 μL, 0.16 mmol) in DMF (0.5 mL). The reaction was warmed to RT over a period of 1 h.

Purification via reverse phase HPLC (10%-99% CH₃CN (0.035% TFA)/H₂O (0.05% TFA)) gave (R)-isobutyl 1-(6-fluoro-2-(2-hydroxyphenyl)quinazolin-4-yl)pyrrolidin-3-ylcarbamate (compound 15) as the TFA salt. LC/MS: m/z 425.3 (M+H)⁺ at 2.75 min (10%-99% CH₃CN (0.035% TFA)/H₂O (0.05% TFA)).

Method B. At −70° C., triethylamine (215 μL, 1.54 mmol) was added to a solution of (R)-2-(4-(3-aminopyrrolidin-1-yl)-6-fluoroquinazolin-2-yl)phenol (250 mg, 0.77 mmol) in CH₂Cl₂ (2.5 mL), followed by the dropwise addition of isobutyl chloroformate (100 μL, 0.77 mmol). The reaction was stirred for 30 minutes and warmed to RT. The mixture was quenched with H₂O and extracted with CH₂Cl₂. The combined organic extracts were dried over MgSO₄, filtered, and concentrated. Purification via silica gel chromatography using 2.5-10% EtOAc in a 1:1 mixture of CH₂Cl₂ and hexanes gave (R)-isobutyl 1-(6-fluoro-2-(2-hydroxyphenyl)quinazolin-4-yl)pyrrolidin-3-ylcarbamate (compound 15) (195 mg, 60%). ¹H NMR (400 MHz, acetic acid-d4) δ 8.43 (m, 1H), 8.01 (m, 1H), 7.90 (m, 1H), 7.76 (m, 1H), 7.58 (d, J=5.6 Hz, 1H), 7.37 (m, 1H), 6.93 (m, 2H), 4.07 (m, 5H), 3.75 (d, J=6.2 Hz, 2H), 2.23 (m, 1H), 2.03 (m, 1H), 1.83 (m, 1H), 0.88 (d, J=6.5 Hz, 6H) ppm. LC/MS: m/z 425.3 (M+H)⁺ at 2.77 min (10%-99% CH₃CN (0.035% TFA)/H₂O (0.05% TFA)).

(R)-Isobutyl 1-(6-fluoro-2-(2-hydroxyphenyl)quinazolin-4-yl)pyrrolidin-3-ylcarbamate hydrochloride (HCl salt of compound 15)

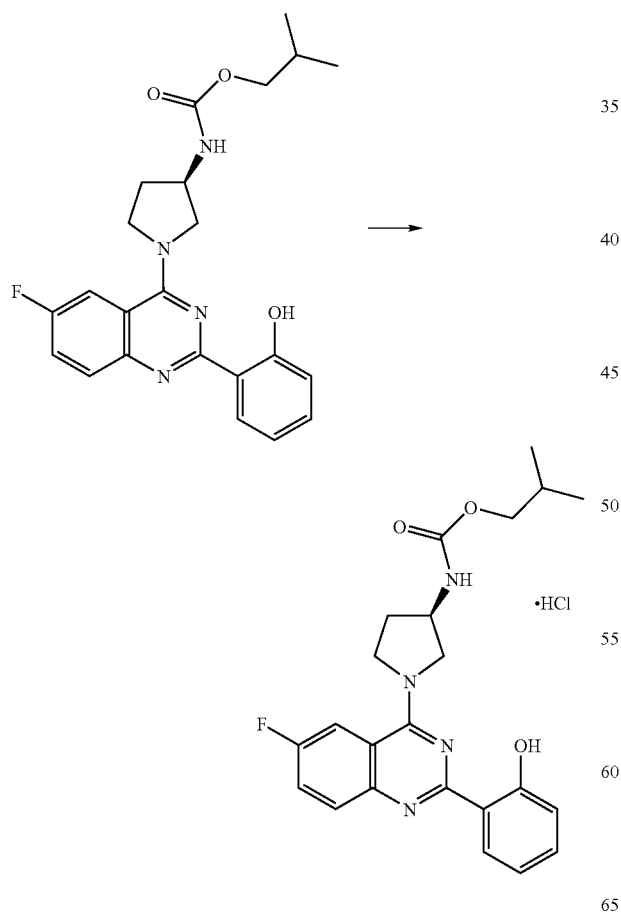

A 2.0 M HCl solution in ether (0.225 mL, 0.45 mmol) was added to a solution of (R)-isobutyl 1-(6-fluoro-2-(2-hydroxyphenyl)quinazolin-4-yl)pyrrolidin-3-ylcarbamate (191 mg, 0.45 mmol) in CH₂Cl₂ (3 mL). More CH₂Cl₂ (3 mL) was added to facilitate stirring. After letting the reaction stir for 20 minutes, ether (12 mL) was added, and stirring was continued for 10 more minutes. The formed precipitate was filtered and dried under vacuum to give (R)-isobutyl 1-(6-fluoro-2-(2-hydroxyphenyl)quinazolin-4-yl)pyrrolidin-3-ylcarbamate hydrochloride (HCl salt of compound 15) (quantitative yield). ¹H NMR (400 MHz, DMSO-d6) δ 8.30 (m, 1H), 8.06 (m, 2H), 7.87 (m, 1H), 7.60 (d, J=5.2 Hz, 1H), 7.46 (m, 1H), 7.02 (m, 2H), 3.91 (m, 7H), 2.23 (m, 1H), 2.06 (m, 1H), 1.83 (m, 1H), 0.88 (d, J=6.6 Hz, 6H) ppm. LC/MS: m/z 425.1 (M+H)⁺ at 2.78 min (10%-99% CH₃CN (0.035% TFA)/H₂O (0.05% TFA)).

Example 17

(R)-Isopropyl 1-(6-fluoro-2-(2-hydroxyphenyl)quinazolin-4-yl)pyrrolidin-3-ylcarbamate (compound 16)

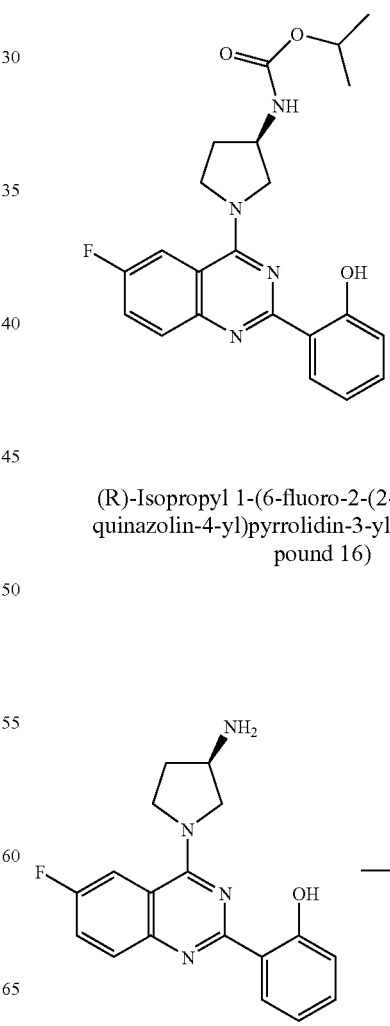

(R)-Isopropyl 1-(6-fluoro-2-(2-hydroxyphenyl)quinazolin-4-yl)pyrrolidin-3-ylcarbamate (compound 16)

-continued

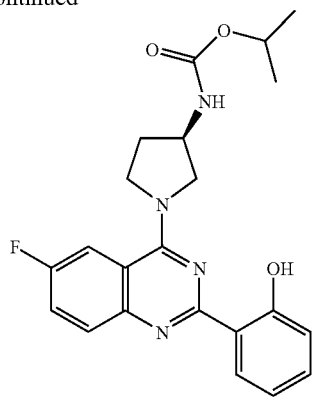

At −40° C., isopropyl chloroformate (9 mg, 0.08 mmol) was added to a solution of (R)-2-(4-(3-aminopyrrolidin-1-yl)-6-fluoroquinazolin-2-yl)phenol (25 mg, 0.08 mmol) and triethylamine (22 µL, 0.16 mmol) in DMF (0.5 mL). The reaction was warmed to RT over a period of 1 h. Purification via reverse phase HPLC (10%-99% $CH_3CN$ (0.035% TFA)/ $H_2O$ (0.05% TFA)) gave (R)-isopropyl 1-(6-fluoro-2-(2-hydroxyphenyl)quinazolin-4-yl)pyrrolidin-3-ylcarbamate (compound 16) as the TFA salt. LC/MS: m/z 411.5 $(M+H)^+$ at 2.75 min (10%-99% $CH_3CN$ (0.035% TFA)/$H_2O$ (0.05% TFA)).

Example 18

(R)-Isobutyl 1-(2-(2-(difluoromethyl)phenyl)-7-methylquinazolin-4-yl)pyrrolidin-3-ylcarbamate (compound 17)

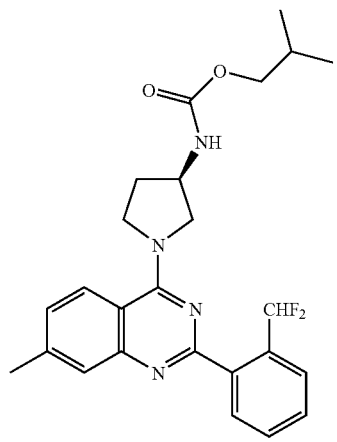

2,4-Dichloro-7-methylquinazoline

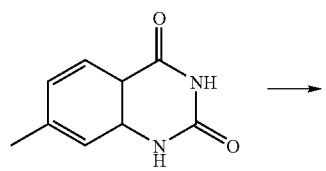

-continued

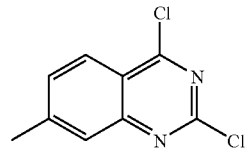

To a suspension of 7-methylquinazoline-2,4(1H,3H)-dione (233 g, 1.32 mol) in phosphoryl chloride (500 ml, 5.23 mol) in a flask equipped with a reflux condenser and a calcium chloride guard tube was added 25 ml N,N-dimethyl aniline. After the production of gas had ceased (about half an hour), the mixture was heated to reflux overnight. The dark solution was cooled to room temperature and slowly poured on 4 L ice and water. The temperature was carefully kept below 5° C. by slowly adding the solution to the vigorously stirred ice and water mixture and by addition of more ice. The cold suspension was extracted with dichloromethane (2×1 L). The dark organic solution was washed with water and saturated aqueous NaCl solution (0.5 L), dried over sodium sulfate, and filtered. The organic layer was filtered through a plug of silica gel. Two fractions were collected which were concentrated to half of the original volume, and 0.5 L heptanes was added to each fraction. Evaporation was continued until crystals started forming. The mixture was cooled to 5° C., and the formed solids were collected by filtration yielding two fractions of 2,4-dichloro-7-methyl-quinazoline: 123 g (44%) of an off-white material and 79 g (28%) of a yellow material.

(R)-tert-Butyl 1-(2-chloro-7-methylquinazolin-4-yl) pyrrolidin-3-ylcarbamate

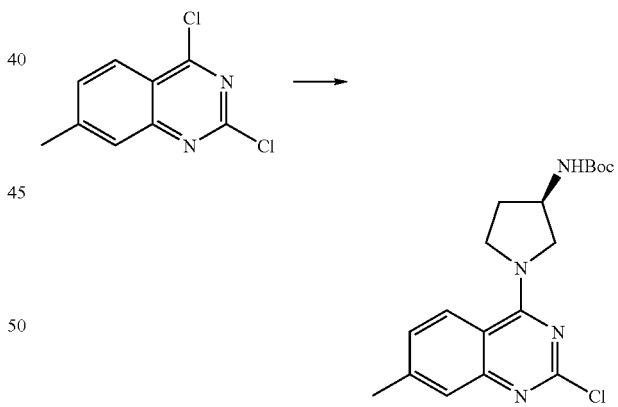

2,4-Dichloro-7-methylquinazoline (2.0 g, 9.4 mmol) was suspended in 40 mL of dichloromethane under an $N_2$ atmosphere and cooled to 0° C. (R)-tert-Butyl pyrrolidin-3-ylcarbamate (1.75 g, 9.4 mmol) was dissolved in a solution of 10 mL of dichloromethane and $Et_3N$ (2.62 mL, 18.8 mmol) and added dropwise to the above reaction mixture. The reaction was warmed to RT and stirred for 16 hours. The reaction was quenched with water, extracted with DCM, dried over $Na_2SO_4$, filtered, and concentrated under reduced pressure. Purification via silica gel chromatography using 0%-10% EtOAc in DCM gave (R)-tert-butyl 1-(2-chloro-7-methylquinazolin-4-yl)pyrrolidin-3-ylcarbamate (2.82 g, 83% yield). LC/MS: m/z 363.1 (M+H)+ at 3.26 min (10%-99% CH₃CN (0.035% TFA)/H₂O (0.05% TFA)).

(R)-1-(2-Chloro-7-methylquinazolin-4-yl)pyrrolidin-3-amine

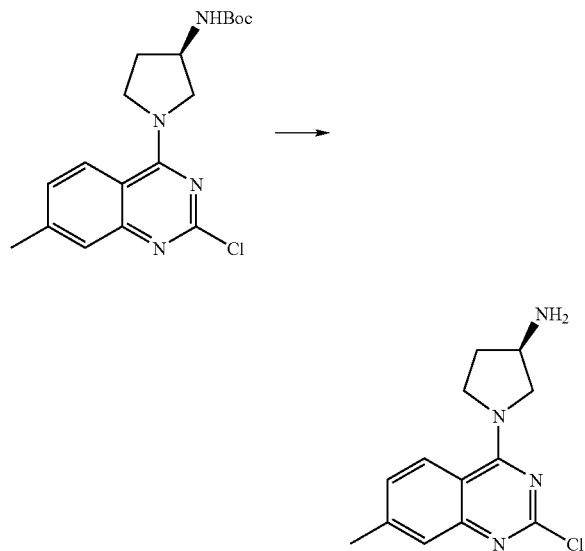

To a solution of (R)-tert-butyl 1-(2-chloro-7-methylquinazolin-4-yl)pyrrolidin-3-ylcarbamate (1.17 g, 3.22 mmol) in 50 mL of dichloromethane was added 10 mL of trifluoroacetic acid in portions. The reaction was stirred at RT for 1 hour. The solvent was evaporated, and the residue was dissolved in 20 mL of dichloromethane, cooled to 0° C., and quenched with 1 M NaOH until basic. After partitioning between CH₂Cl₂ and H₂O, the mixture was separated and the aqueous layer was twice extracted with CH₂Cl₂. The combined organic layers were dried over Na₂SO₄, filtered, and concentrated under reduced pressure. Purification via silica gel chromatography using 0%-10% EtOAc in DCM gave (R)-1-(2-chloro-7-methylquinazolin-4-yl)pyrrolidin-3-amine (800 mg, 94% yield). LC/MS: m/z 262.9 (M+H)+ at 0.79 min (10%-99% CH₃CN (0.035% TFA)/H₂O (0.05% TFA)).

(R)-Isobutyl 1-(2-chloro-7-methylquinazolin-4-yl)pyrrolidin-3-ylcarbamate

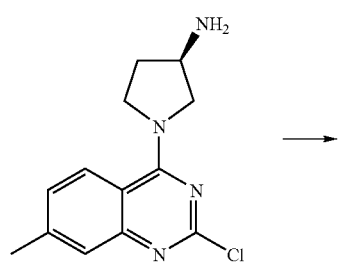

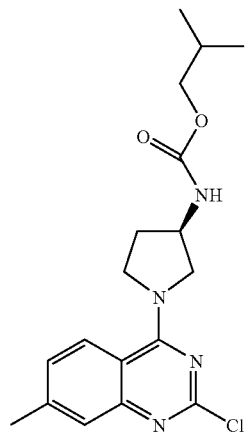

A solution of (R)-1-(2-chloro-7-methylquinazolin-4-yl)pyrrolidin-3-amine (100 mg, 0.38 mmol) in 2 mL of dichloromethane was cooled to −30° C. To it was added Et₃N followed by the addition of isobutyl chloroformate dropwise. The reaction was complete after 5 minutes. The reaction was quenched with water, the layers separated, and the aqueous layer was twice extracted with CH₂Cl₂. The combined organic layers were dried over Na₂SO₄, filtered, and concentrated. Purification via silica gel chromatography using 0%-10% EtOAc in DCM gave (R)-isobutyl 1-(2-chloro-7-methylquinazolin-4-yl)pyrrolidin-3-ylcarbamate (90 mg, 66% yield). LC/MS: m/z 363.3 (M+H)+ at 2.74 min (10%-99% CH₃CN (0.035% TFA)/H₂O (0.05% TFA)).

1-Bromo-2-difluoromethyl-benzene

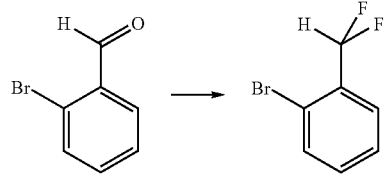

A solution of 2-bromobenzaldehyde (55.5 g, 300 mmol) and (diethylamino)sulfur trifluoride (75.0 g, 467 mmol) in 250 ml dichloromethane was refluxed under a nitrogen atmosphere overnight. The cooled solution was poured into 0.5 L aqueous 15% NaHCO₃ and stirred until no more CO₂ was produced. The layers were separated, and the aqueous layer was extracted with 250 ml dichloromethane. The combined organic layers were washed with 250 ml 5% aq. NaHCO₃ and saturated aq. NaCl, dried over Na₂SO₄, filtered, and evaporated to dryness under reduced pressure. The crude material was purified by vacuum distillation, and the fraction boiling at 62-63° C. at 12 mbar was collected, yielding 1-bromo-2-difluoromethyl-benzene (42.6 g, 69%) as a light-yellow oil.

2-(2-Difluoromethyl-phenyl)-4,4,5,5-tetramethyl-[1,3,2]dioxaborolane

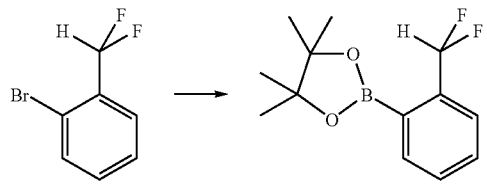

To a solution of 1-bromo-2-difluoromethyl-benzene (19.8 g, 95.7 mmol) in dry THF (200 ml) at −78° C. under a nitrogen atmosphere was added 2.5 M n-BuLi in hexanes (42 ml, 105 mmol) slowly. After completion of the addition, the resulting dark solution was stirred for an additional hour at −78° C. Subsequently, 2-isopropoxy-4,4,5,5-tetramethyl-1,3,2-dioxaborolane (25 ml, 123 mmol) was added, and the solution was slowly warmed to room temperature. After stirring overnight at room temperature under a nitrogen atmosphere the solution was poured into 400 ml water. Ethyl acetate (300 ml) was added and the layers were separated. The aqueous layer was extracted twice with ethyl acetate (150 ml and 50 ml respectively), and the combined organic layers were washed with water, dried over $Na_2SO_4$, filtered, and evaporated to dryness under reduced pressure. The resulting brown oil (21 g) was purified by bulb-to-bulb-distillation at $3 \times 10^{-3}$ mbar at 90-95° C. to yield 2-(2-difluoromethyl-phenyl)-4,4,5,5-tetramethyl-[1,3,2]dioxaborolane (14.4 g, 59%) as a slightly yellow oil.

(R)-Isobutyl 1-(2-(2-(difluoromethyl)phenyl)-7-methylquinazolin-4-yl)pyrrolidin-3-ylcarbamate (compound 17)

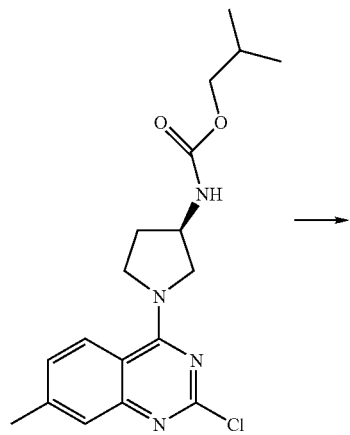

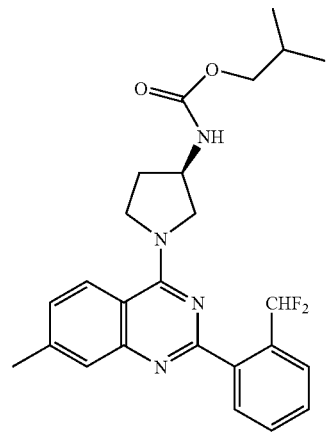

A solution of (R)-isobutyl 1-(2-chloro-7-methylquinazolin-4-yl)pyrrolidin-3-ylcarbamate (50 mg, 0.14 mmol), 2-(2-difluoromethyl-phenyl)-4,4,5,5-tetramethyl-[1,3,2]dioxaborolane (42 mg, 0.17 mmol), $PdCl_2$(dppf).$CH_2Cl_2$ (10 mg, 0.01 mmol), $K_2CO_3$ (38 mg, 0.28 mmol), and water (0.05 mL) in acetonitrile (0.5 mL) was heated by microwave irradiation at 150° C. for 15 minutes. The reaction mixture was filtered, and purification using preparative HPLC (10%-99% $CH_3CN$ (0.035% TFA)/$H_2O$ (0.05% TFA)) gave (R)-isobutyl 1-(2-(2-(difluoromethyl)phenyl)-7-methylquinazolin-4-yl)pyrrolidin-3-ylcarbamate as the TFA salt. LC/MS: m/z 455.5 $(M+H)^+$ at 2.58 min (10%-99% $CH_3CN$ (0.035% TFA)/$H_2O$ (0.05% TFA)).

(R)-Neopentyl 1-(2-(2-(difluoromethyl)phenyl)-7-methylquinazolin-4-yl)pyrrolidin-3-ylcarbamate (compound 18)

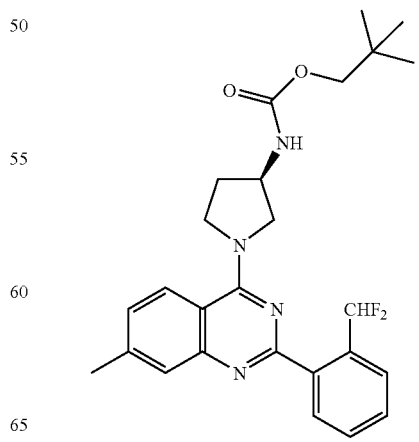

(R)-Neopentyl 1-(2-chloro-7-methylquinazolin-4-yl)pyrrolidin-3-ylcarbamate

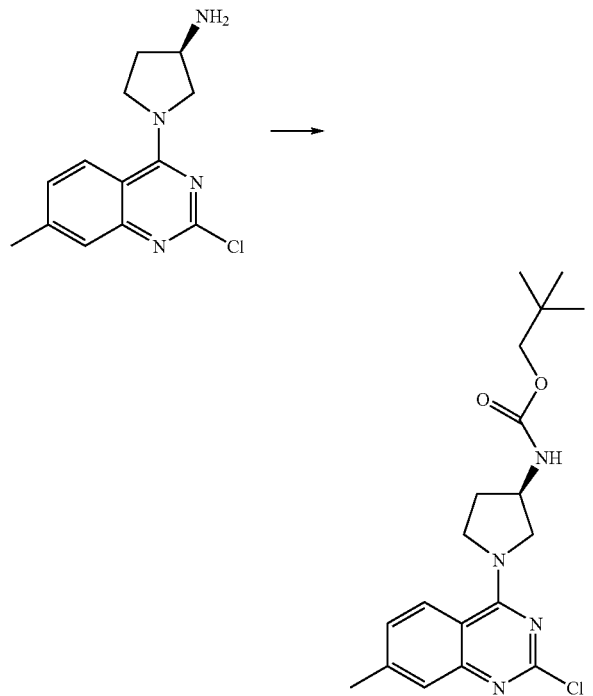

A solution of (R)-1-(2-chloro-7-methylquinazolin-4-yl)pyrrolidin-3-amine (100 mg, 0.38 mmol) in 2 mL of THF was cooled to −30° C. To it was added Et$_3$N followed by the addition of neopentyl chloroformate (53 μL, 0.38 mmol) dropwise. The reaction was complete after 5 minutes. The reaction was quenched with water, the layers separated, and the aqueous layer was twice extracted with CH$_2$Cl$_2$. The combined organic layers were dried over Na$_2$SO$_4$, filtered, and concentrated under reduced pressure. Purification via silica gel chromatography using 0%-10% EtOAc in DCM gave (R)-neopentyl 1-(2-chloro-7-methylquinazolin-4-yl)pyrrolidin-3-ylcarbamate (100 mg, 70% yield). LC/MS: m/z 377.5 (M+H)$^+$ at 2.90 min (10%-99% CH$_3$CN (0.035% TFA)/H$_2$O (0.05% TFA)).

(R)-Neopentyl 1-(2-(2-(difluoromethyl)phenyl)-7-methylquinazolin-4-yl)pyrrolidin-3-ylcarbamate (compound 18)

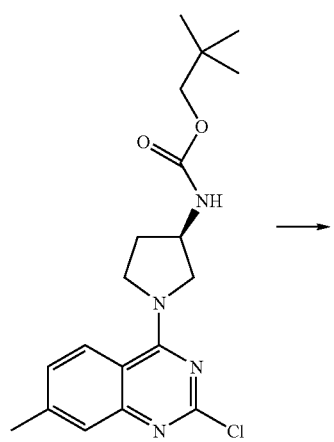

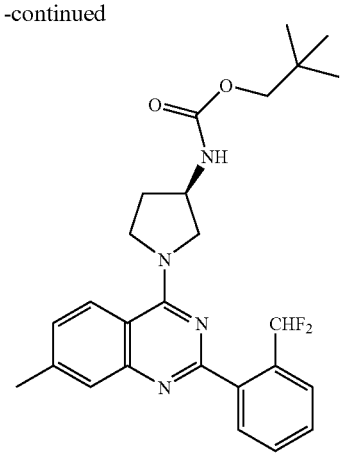

A solution of (R)-neopentyl 1-(2-chloro-7-methylquinazolin-4-yl)pyrrolidin-3-ylcarbamate (50 mg, 0.13 mmol), 2-(2-difluoromethyl-phenyl)-4,4,5,5-tetramethyl-[1,3,2]dioxaborolane (42 mg, 0.16 mmol), PdCl$_2$(dppf).CH$_2$Cl$_2$ (9.7 mg, 0.01 mmol), K$_2$CO$_3$ (37 mg, 0.28 mmol), and water (0.05 mL) in acetonitrile (0.5 mL) was heated by microwave irradiation at 150° C. for 15 minutes. The reaction mixture was filtered, and purification using preparative HPLC (10%-99% CH$_3$CN (0.035% TFA)/H$_2$O (0.05% TFA)) gave (R)-neopentyl 1-(2-(2-(difluoromethyl)phenyl)-7-methylquinazolin-4-yl)pyrrolidin-3-ylcarbamate as the TFA salt. LC/MS: m/z 468.54 (M+H)$^+$ at 2.69 min (10%-99% CH$_3$CN (0.035% TFA)/H$_2$O (0.05% TFA)).

Table 3 below recites analytical data for exemplary compounds of the present invention. "RT" means retention time in minutes.

TABLE 3

| Cmpd No. | LC/MS M + 1 | LC/RT min |
|---|---|---|
| 1 | 441.5 | 2.04 |
| 2 | 393.3 | 2.3 |
| 3 | 407.5 | 2.42 |
| 4 | 439.5 | 2.87 |
| 5 | 421 | 2.81 |
| 6 | 423.3 | 2.54 |
| 7 | 421 | 2.83 |
| 8 | 439.5 | 2.41 |
| 9 | 435.5 | 2.69 |
| 10 | 411.3 | 2.15 |
| 11 | 453.3 | 2.53 |
| 12 | 407.7 | 2.42 |
| 13 | 425.1 | 2.29 |
| 14 | 423.5 | 2.17 |
| 15 | 425.3 | 2.75 |
| 16 | 411.5 | 2.75 |
| 17 | 455.5 | 2.58 |
| 18 | 469.5 | 2.69 |

Methods:

(A) Micromass MUX LCT 4 channel LC/MS, Waters 60F pump, Gilson 215 4 probe autosampler, Gilson 849 injection module, 1.5 mL/min/column flow rate, 10-99% CH$_3$CN (0.035% TFA)/H$_2$O (0.05% TFA) gradient, Phenomenex Luna 5u C18 columns (50×4.60 mm), Waters MUX UV-2488 UV detector, Cedex 75 ELSD detectors.

(B) PESciex API-150-EX LC/MS, Shimadzu LC-8A pumps, Gilson 215 autosampler, Gilson 819 injection module, 3.0 mL/min flow rate, 10-99% CH$_3$CN (0.035% TFA)/

H$_2$O (0.05% TFA) gradient, Phenomenex Luna 5u C18 column (50×4.60 mm), Shimadzu SPD-10A UV/Vis detector, Cedex 75 ELSD detector.

(C)PESciex API-150-EX LC/MS, Shimadzu LC-8A pumps, Gilson 215 autosampler, Gilson 819 injection module, 3.0 mL/min flow rate, 40-99% CH$_3$CN (0.035% TFA)/H$_2$O (0.05% TFA) gradient, Phenomenex Luna 5u C18 column (50×4.60 mm), Shimadzu SPD-10A UV/Vis detector, Cedex 75 ELSD detector.

Assays for Detecting and Measuring NaV Inhibition Properties of Compounds

A) Optical Methods for Assaying NaV Inhibition Properties of Compounds:

Compounds of the invention are useful as antagonists of voltage-gated sodium ion channels. Antagonist properties of test compounds were assessed as follows. Cells expressing the NaV of interest were placed into microtiter plates. After an incubation period, the cells were stained with fluorescent dyes sensitive to the transmembrane potential. The test compounds were added to the microtiter plate. The cells were stimulated with either a chemical or electrical means to evoke a NaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

B) VIPR® Optical Membrane Potential Assay Method with Chemical Stimulation

Cell Handling and Dye Loading 24 hours before the assay on VIPR, CHO cells endogenously expressing a NaV1.2 type voltage-gated NaV are seeded in 96-well poly-lysine coated plates at 60,000 cells per well. Other subtypes are performed in an analogous mode in a cell line expressing the NaV of interest.

1) On the day of the assay, medium is aspirated and cells are washed twice with 225 µL of Bath Solution #2 (BS#2).
2) A 15 uM CC2-DMPE solution is prepared by mixing 5 mM coumarin stock solution with 10% Pluronic 127 1:1 and then dissolving the mix in the appropriate volume of BS#2.
3) After bath solution is removed from the 96-well plates, the cells were loaded with 80 µL of the CC2-DMPE solution. Plates are incubated in the dark for 30 minutes at room temperature.
4) While the cells are being stained with coumarin, a 15 µL oxonol solution in BS#2 is prepared. In addition to DiSBAC$_2$(3), this solution should contain 0.75 mM ABSC1 and 30 µL veratridine (prepared from 10 mM EtOH stock, Sigma #V-5754) and/or deltamethrin.
5) After 30 minutes, CC2-DMPE is removed and the cells are washed twice with 225 µL of BS#2. As before, the residual volume should be 40 µL.
6) Upon removing the bath, the cells are loaded with 80 µL of the DiSBAC$_2$(3) solution, after which test compound, dissolved in DMSO, is added to achieve the desired test concentration to each well from the drug addition plate and mixed thoroughly. The volume in the well should be roughly 121 µL. The cells are then incubated for 20-30 minutes.
7) Once the incubation is complete, the cells are ready to be assayed on VIPR® with a sodium add back protocol. 120 µL of Bath solution #1 is added to stimulate the NaV dependent depolarization. 200 µL tetracaine is used as an antagonist positive control for block of the NaV channel.

Analysis of VIPR® Data:

Data is analyzed and reported as normalized ratios of background-subtracted emission intensities measured in the 460 nm and 580 nm channels. Background intensities were then subtracted from each assay channel. Background intensities are obtained by measuring the emission intensities during the same time periods from identically treated assay wells in which there were no cells. The response as a function of time is then reported as the ratios obtained using the following formula:

$$R(t) = \frac{(intensity_{460\,nm} - background_{460\,nm})}{(intensity_{580\,nm} - background_{580\,nm})}$$

The data is further reduced by calculating the initial ($R_i$) and final ($R_f$) ratios. These are the average ratio values during part or all of the pre-stimulation period, and during sample points during the stimulation period. The response to the stimulus $R=R_f/R_i$ is then calculated. For the Na$^+$ add back analysis time windows, baseline is 2-7 sec and final response is sampled at 15-24 sec.

Control responses are obtained by performing assays in the presence of a compound with the desired properties (positive control), such as tetracaine, and in the absence of pharmacological agents (negative control). Responses to the negative (N) and positive (P) controls are calculated as above. The compound antagonist activity A was defined as:

$$A = \frac{R - P}{N - P} * 100.$$

where R was the ratio response of the test compound

Solutions [mM]

Bath Solution #1: NaCl 160, KCl 4.5, CaCl$_2$ 2, MgCl$_2$ 1, HEPES 10, pH 7.4 with NAOH Bath Solution #2 TMA-Cl 160, CaCl$_2$ 0.1, MgCl$_2$ 1, HEPES 10, pH 7.4 with KOH (final K concentration ~5 mM)

CC2-DMPE: prepared as a 5 mM stock solution in DMSO and stored at −20° C.

DiSBAC6(3): prepared as a 5 mM stock in DMSO and stored at −20° C.

ABSC1: prepared as a 200 mM stock in distilled H$_2$O and stored at room temperature Cell Culture CHO cells are grown in DMEM (Dulbecco's Modified Eagle Medium; GibcoBRL #10569-010) supplemented with 10% FBS (Fetal Bovine Serum, qualified; GibcoBRL #16140-071) and 1% Pen-Strep (Penicillin-Streptomycin; GibcoBRL #15140-122). Cells are grown in vented cap flasks, in 90% humidity and 10% CO$_2$, to 100% confluence. They are split by trypsinization 1:10 or 1:20, depending on scheduling needs, and then grown for 2-3 days before the next split.

C) VIPR® Optical Membrane Potential Assay Method with Electrical Stimulation

The following was an example of how NaV1.8 inhibition activity was measured using the optical membrane potential method #2. Other subtypes were performed in an analogous mode in a cell line expressing the NaV of interest.

HEK293 cells stably expressing NaV1.8 were plated into 96-well microtiter plates. After an appropriate incubation period, the cells were stained with the voltage sensitive dyes CC2-DMPE/DiSBAC6(3) as follows.

Reagents:
100 mg/mL Pluronic F-127 (Sigma #P2443), in dry DMSO
5 mM DiSBAC6(3) (Aurora #00-100-010) in dry DMSO
5 mM CC2-DMPE (Aurora #00-100-008) in dry DMSO
5 mM β-cyclodextrin
Bath Solution #1 (see above)
200 mM Aurora ABSC1

Loading Protocol:
2×CC2-DMPE/DiSBAC6(3)=8 µM CC2-DMPE/8 µM DiSBAC6(3): 10 mM CC2-DMPE and DiSBAC6(3) was vortexed with an equivalent volume of 10% pluronic, followed by vortexing in required amount of Bath Solution #1. Each cell plate required 5 mL of 2×CC2-DMPE/DiSBAC6(3). 50 µL of 2×CC2-DMPE/DiSBAC6(3) was added to wells containing washed cells, resulting in a 4 µM final staining concentration of both dyes. The cells were stained for 30 minutes in the dark at RT.

2×ABSC1=1 mM ABSC1: The required amount of 200 mM ABSC1 was added to a 50 ml conical tube and mixed with 1 µL 10% pluronic for each mL of solution made and vortexed together. Then Bath Solution #1 was added to make up a 2× solution. Finally, the ABSC1 was added.

The 2×ABSC1 solution was used to solvate compound plates. Note that compound plates were made at 2× drug concentration. The stained plate was washed again, leaving residual volume of 50 µL. Added 50 µL/well of the 2×ABSC1. The cells were stained for 30 minutes in the dark at RT.

The electrical stimulation instrument and methods of use are described in ION Channel Assay Methods PCT/US01/21652 and *Nat Biotech* 2006, 24(4), 439-446, both herein incorporated by reference. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passed user-programmed electrical stimulus protocols to cells within the wells of the microtiter plate.

Reagents
Assay buffer #1=Bath Solution #1
Pluronic stock (1000×): 100 mg/mL pluronic 127 in dry DMSO;
Oxonol stock (3333×): 5 mM DiSBAC6(3) in dry DMSO;
Coumarin stock (1000×): 5 mM CC2-DMPE in dry DMSO;
ABSC1 stock (400×): 200 mM ABSC1 in water.

Assay Protocol
1. Inserted or used electrodes into each well that was assayed.
2. Used the current-controlled amplifier to deliver stimulation wave pulses for 3 s. Two seconds of pre-stimulus recording was performed to obtain the un-stimulated intensities. Five seconds of post-stimulation recording was performed to examine the relaxation to the resting state.

Data Analysis

Data was analyzed and reported as normalized ratios of background-subtracted emission intensities measured in the 460 nm and 580 nm channels. Background intensities were then subtracted from each assay channel. Background intensities were obtained by measuring the emission intensities during the same time periods from identically treated assay wells in which there were no cells. The response as a function of time was then reported as the ratios obtained using the following formula:

$$R(t) = \frac{(intensity_{460\,nm} - background_{460\,nm})}{(intensity_{580\,nm} - background_{580\,nm})}$$

The data was further reduced by calculating the initial ($R_i$) and final ($R_f$) ratios. These were the average ratio values during part or all of the pre-stimulation period, and during sample points during the stimulation period. The response to the stimulus $R=R_f/R_i$ was then calculated.

Control responses were obtained by performing assays in the presence of a compound with the desired properties (positive control), such as tetracaine, and in the absence of pharmacological agents (negative control). Responses to the negative (N) and positive (P) controls were calculated as above. The compound antagonist activity A was defined as:

$$A = \frac{R - P}{N - P} * 100.$$

where R is the ratio response of the test compound.

Electrophysiology Assays for NaV Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 µm in diameter) were visually identified and probed with fine tip glass electrodes connected to an amplifier (Axon Instruments). The "voltage clamp" mode was used to assess the compound's IC50 holding the cells at −60 mV. In addition, the "current clamp" mode was employed to test the efficacy of the compounds in blocking action potential generation in response to current injections. The results of these experiments contributed to the definition of the efficacy profile of the compounds.

VOLTAGE-CLAMP Assay in DRG Neurons

TTX-resistant sodium currents were recorded from DRG somata using the whole-cell variation of the patch clamp technique. Recordings were made at room temperature (~22° C.) with thick walled borosilicate glass electrodes (WPI; resistance 3-4 MΩ) using an Axopatch 200B amplifier (Axon Instruments). After establishing the whole-cell configuration, approximately 15 minutes was allowed for the pipette solution to equilibrate within the cell before beginning recording. Currents were low pass filtered between 2-5 kHz and digitally sampled at 10 kHz. Series resistance was compensated 60-70% and was monitored continuously throughout the experiment. The liquid junction potential (−7 mV) between the intracellular pipette solution and the external recording solution was not accounted for in the data analysis. Test solutions were applied to the cells with a gravity driven fast perfusion system (SF-77; Warner Instruments).

Dose-response relationships were determined in voltage clamp mode by repeatedly depolarizing the cell from the experiment specific holding potential to a test potential of +10 mV once every 60 seconds. Blocking effects were allowed to plateau before proceeding to the next test concentration.

Solutions

Intracellular solution (in mM): Cs—F (130), NaCl (10), $MgCl_2$ (1), EGTA (1.5), $CaCl_2$ (0.1), HEPES (10), glucose (2), pH=7.42, 290 mOsm.

Extracellular solution (in mM): NaCl (138), $CaCl_2$ (1.26), KCl (5.33), $KH_2PO_4$ (0.44), $MgCl_2$ (0.5), $MgSO_4$ (0.41), $NaHCO_3$ (4), $Na_2HPO_4$ (0.3), glucose (5.6), HEPES (10), $CdCl_2$ (0.4), $NiCl_2$ (0.1), TTX ($0.25 \times 10^{-3}$).

CURRENT-CLAMP Assay for NaV Channel Inhibition Activity of Compounds

Cells were current-clamped in whole-cell configuration with a Multiplamp 700A amplifier (Axon Inst). Borosilicate pipettes (4-5 MOhm) were filled with (in mM):150 K-gluconate, 10 NaCl, 0.1 EGTA, 10 Hepes, 2 $MgCl_2$, (buffered to pH 7.34 with KOH). Cells were bathed in (in mM): 140 NaCl, 3 KCl, 1 MgCl, 1 CaCl, and 10 Hepes). Pipette potential was zeroed before seal formation; liquid junction potentials were not corrected during acquisition. Recordings were made at room temperature.

Following these procedures, representative compounds of the present invention were found to possess desired voltage gated sodium channel activity and selectivity.

Assays for Detecting and Measuring L-Type CaV 1.2 Inhibition Properties of Compounds A) Optical methods for assaying CaV inhibition properties of compounds:

Compounds of the invention are useful as antagonists of voltage-gated calcium ion channels. Antagonist properties of test compounds were assessed as follows. Cells expressing the CaV of interest were placed into microtiter plates. After an incubation period, the cells were stained with fluorescent dyes sensitive to the transmembrane potential. The test compounds were added to the microtiter plate. The cells were stimulated with electrical means to evoke a CaV dependent membrane potential change from unblocked channels, which was detected and measured with trans-membrane potential-sensitive dyes. Antagonists were detected as a decreased membrane potential response to the stimulus. The optical membrane potential assay utilized voltage-sensitive FRET sensors described by Gonzalez and Tsien (See, Gonzalez, J. E. and R. Y. Tsien (1995) "Voltage sensing by fluorescence resonance energy transfer in single cells" *Biophys J* 69(4): 1272-80, and Gonzalez, J. E. and R. Y. Tsien (1997) "Improved indicators of cell membrane potential that use fluorescence resonance energy transfer" *Chem Biol* 4(4): 269-77) in combination with instrumentation for measuring fluorescence changes such as the Voltage/Ion Probe Reader (VIPR®) (See, Gonzalez, J. E., K. Oades, et al. (1999) "Cell-based assays and instrumentation for screening ion-channel targets" *Drug Discov Today* 4(9): 431-439).

VIPR® optical membrane potential assay method with electrical stimulation

Positive Control (100% Block)

The positive control for this assay was 125 uM mibefradil, achieved by adding 25 uL of 250 uM solution to the assay plates containing 25 uL of assay buffer. Each assay plate included positive control wells.

Negative Control (No Block)

The negative (baseline) control for this assay was DMSO. This was achieved by adding 25 uL of 1% DMSO (in assay buffer) to the assay plates containing 25 uL of assay buffer. Each assay plate included negative control wells.

Background Subtraction

Fluorescence background from plastic in assay plates (or from the assay buffer) was assessed by running a cell-free plate through the EVIPR under the same optical configuration. The average background values for each row and each wavelength were subtracted in MOD 3 prior to ratio change and activity calculations.

Reagents

Assay Buffers:

Bath Y (Prepared by Vertex Lab Support)

140 mM TMA-Cl 4.5 mM KCl 1 mM $MgCl_2$ 10 mM HEPES, pH7.4

10 mM glucose

Osmolarity=295mOsm (280-310 acceptable range)

500 mM $BaCl_2$ (Sigma #B0750), in $H_2O$ 100 mg/mL Pluronic F-127 (Sigma #P2443), in dry DMSO 10 mM $DiSBAC_2(3)$ (Aurora #00-100-010) in dry DMSO 10 mM CC2-DMPE (Aurora #00-100-008) in dry DMSO 200 mM Acid Yellow 17 (Aurora #VABSC) in $H_2O$ Assay Volume 50 uL DMSO Conc in Assay 0.5% (1 uL of 75% DMSO/25% water, dilution factor of 160)

Incubation Time of Compounds 20-25 minutes

Instrumentation

This screen was conducted on the Allegro™ system. The system is diagrammed below:

The Allegro™ was equipped with a compound plate storage unit (stacker). The stacker holds a set of trays (each tray holds 12 compound plates). The libraries were received from Compound Management, as pre-spotted (1 µL/well of compound and controls) intermediate plates in 384-well format, as a 1.6 mM stock solution in 75% DMSO/25% de-ionized $H_2O$. The plates were diluted in 80 uL oxonol dye solution to create a 2× stock. Three EVIPR readers were integrated to the Allegro system by a Mitsubishi robotic arm. Only one EVIPR was used per run.

Instrumentation Settings

Optical:

Read Frequency: 10 Hz

Excitation Wavelength: 400 nm

Emission Wavelengths: 460 nm and 560 nm

Electrical Stimulation:

Pulse Width: 11.1ms

Stimulation Current: 0.8 amps

Stimulation Frequency: 90 Hz

Pre-stimulation time: 2 s

Stimulation time: 3 s

Post-stimulation time: 1 s

Waveform: Biphasic Square Wave

Plate Washer Settings:

Settings for ELx405washer will leave a residual volume of 25 uL.

Plate Type: 384 # of cycles: 3

Soak/shake: No

| Dispense: | dispense volume | 100 |
| --- | --- | --- |
| | dispense flow rate | 1 |
| | dispense height | 80 |
| | horizontal disp pos | −20 |
| | horiz y disp pos | −5 |
| Aspirate: | aspirate height | 48 |
| | horizontal aspr pos | −18 |
| | horiz y asp pos | −5 |
| | aspiration rate | 0 |
| | aspiration delay | 0 |
| | final asp delay | 500 |

Assay Procedure
  Procedure run on HTS Allegro™:
  1. Carousel: Assay plates (Cell plates) loaded into carousel module #1 ($CO_2$=5%, ambient temperature and Rh)
  2. Barrier: Assay plates retrieved from carousel and passed through environmental barrier (The remaining steps are conducted at room temperature and ambient $CO_2$)
  3. Washer: Assay plates washed with Bath Y on Biotek ELx405.
  4. MultiReagent Dispenser (MRD): 25 uL of CC2-DMPE (and equal volume Pluronic) in Bath Y added to each well to make 10 uM.
  5. Barrier: Assay plates passed through barrier.
  6. Carousel: 30-minute incubation at room temperature.
  7. Barrier: Assay plates passed through barrier.
  8. Washer: Assay plates washed with Bath Y on Biotek ELx405
  9. High Density Transfer Station:
    a. 80 uL oxonol dye loading solution (4 uM DiSBAC2(3), 1 mM VABSC and 30 mM $BaCl_2$ in Bath Y) added to compound plates (pre-spotted with 1 uL compound) using a MultiDrop (offline)
    b. Plates mixed (3 times 20 uL) on CyBiWell (offline). Plates loaded onto compound tray.
    c. Compound tray retrieved from compound tray stacker and compound plate barcodes read.
    d. Assay plate barcode read and moved to SciClone deck
    e. 25 uL compound plus oxonol aspirated from compound plate on SciClone deck and transferred to assay plate.
      i. Final assay volume=50 uL
      ii. Final compound concentration=10 uM
    f. SciClone tips washed in DMSO and 5% ethanol in water to remove external carry-over.
  10. Carousel: Assay plates incubated for 20 minutes at RT
  11. Barrier: Assay plates passed through final barrier
  12. Mitsubishi Robotic Arm: Retrieves assay plate from barrier output, delivers cell plates to EVIPR 384-1, and sends command to initiate EVIPR run.
Assay Window
  Assay window criteria:
  Passing plates≦0.5, rejected plates>0.5

$$\text{Assay Window} = \frac{3(SD_{FullBlock} + SD_{Baseline})}{(AVE_{Baseline} - AVE_{FullBlock})} = 1 - Z'$$

Data Reduction
  The EVIPR files were reduced to decrease the amount of data pumped into the database. Two "windows" of interest were filtered out of each EVIPR file. Each window is a slice of the response measured in each well. The first window is measured before stimulation. The second window samples the peak of the response. The ratio of the two is used to determine the response size.

Data Analysis
  Once the data were collected on the VIPR, they were archived and uploaded, in reduced form, to Mod 3. Once in Mod 3, each individual assay plate was QC'ed (looking for acceptable window and dynamic range).
  hERG Assay: planar patch
  hERG-inhibition was assayed in a Chinese Hamster Lung cell line (CHL) stably transduced with the structural gene for hERG. Cells express high numbers of hERG channels resulting in 500 pA to 1.5nA of hERG outward $K^+$ currents. The method used a planar patch instrument (IonWorks HT, Molecular Devices) that allowed medium-throughput electrophysiology measurements in 384-well format. The potency of hERG inhibition was measured at 1.1 µM, 3.3 µM, 10 µM, and 30 µM of the compound studied. The compound was added from a 3× aqueous addition buffer.
  hERG Assay: Manual Patch.
  hERG-inhibition was assayed in a Chinese Hamster Lung cell line (CHL) stably transduced with the structural gene for hERG. For electrophysiological experiments, cells were grown on small coverslips and used for recording after 2 to 3 days in culture. Electrophysiological recordings were performed with an Axopatch 200A amplifier (Axon Instruments). Internal solution: 100 mM K-gluconate, 40 mM KCl, 3.2 mM $MgCl_2$, 5 mM HEPES, 5 mM EGTA, pH 7.25-7.3 using KOH. Bath solution: 140 mM NaCl, 4.5 mM KCl, 10 mM NaHEPES, 2 mM $CaCl_2$, 1 mM $MgCl_2$, 10 mM glucose, pH 7.25-7.3 using KOH. hERG tail currents were elicited with the stimulation protocol shown below, with peak outward currents seen in FIG. 1 phases A and B of stimulation measured in the presence or absence of test compounds (6-10 min exposure).
  The compounds of the present invention exhibit a desirably low activity against hERG.
  CYP-450 Isozyme Assay
  Compound Preparation:
  1. The desired compound was plated (2 mM in 75% DMSO/25% $H_2O$) with a Pieso Sample Distribution Robot (PSDR™) at 8 nL per well.
  2. The compound was centrifuged briefly at approximately 1000 rpm to shift the compound drop to the bottom of the well.
  3. PVP 10 K (excipient, 0.2% in 75% DMSO/25% $H_2O$) was plated with a PSDR™ at 100 mL per well.
  4. The compound and PVP 10 K were centrifuged briefly at approximately 1000 rpm to ensure an adequate mix of compound and excipient.
  5. The dry-down of the plates was initiated using house vacuum for at least 3 hours.
  6. The plates were transferred to a high vacuum (50 millitorr) apparatus and the dry-down process was continued for at least 15 hours.
  The following assay protocol was employed for a desired CYP-450 isozyme (CYP3A4, CYP2C9, CYP1A2, CYP2C19, or CYP2D6).
  Assay Protocol
  All reagents below were added using a Flying Reagent Dispenser (FRD™).
  1. 800 mL of $dH_2O$ was added to the 100% activity control, compound, and background control wells.
  2. 800 mL of the appropriate control drug (3A4:clotrimazole, 2C9:miconazole, 1A2:ticlopidine, $2C_{19}$:lansoprazole, or 2D6:propanolol; 10 uM final dissolved in $dH_2O$) was added to the drug control wells.
  3. 200 mL of 500 mM $K^+$ Phosphate buffer (pH 8.4)was added to the 100% activity control, drug control, and compound wells.

4. 600 mL of Control Insect Baculosomes (PanVera P2315) in 500 mM K⁺ Phosphate Buffer (pH 8.4) was added to the background control wells. The calculation for this reagent was based on the protein concentration of the 100% activity control wells.
5. The plate was scanned for compound fluorescence using a NanoPlate™ Fluorescence Plate Reader (NPR™).
6. 200 mL of NADP⁺ (Sigma, 100 µM final) and substrate in 100 mM K⁺ Phosphate buffer (50 mM K⁺ Phosphate buffer for 2C9 and 2C19) was added to all wells. Fluorogenic substrate (3A4:5 µM Vivid™ 3A4 Red, 2C9:1 µM Vivid™ 2C9 Green, 1A2:2 µM Vivid™ 1A2 Blue, 2C19:10 M Vivid™ 2C19 Blue, and 2D6: 10 µM Vivid™ 2D6 Blue) was added at a final concentration corresponding to the $K_m$ of the substrate for its pertinent CYP450 isozyme.
7. 400 mL of the desired CYP450 isozyme and recycling buffer (3.3 mM glucose-6-phosphate, 0.4units/ml glucose-6-phosphate dehydrogenase, 100 mM MgCl₂, and 0.00025% Antifoam 289; reagents obtained from Sigma) in 100 mM K⁺ Phosphate Buffer (50 mM K⁺ Phosphate buffer for 2C9 and 2C19) were added to the 100% activity control, drug control, and compound wells. The desired isozyme was added to obtain the following final concentrations of the desired isozyme: 5 nM CYP3A4, 10 nM CYP2C9, 5 nM CYP1A2, 5 nM CYP2C19, or 20 nM CYP2D6.
8. The plate was incubated for 60 minutes at room temperature.
9. The plate was scanned for solution fluorescence using a NanoPlate™ Fluorescence Plate Reader (NPR™).
10. The NPR™ data was converted into a format compatible with importation into a data visualizer and complete the analysis of data acquired.

The compounds of the present invention exhibit a desirably low activity against one or more of the CYP450 isozymes.

The activity of selected compounds of the present invention against NaV 1.8 channel is shown below in Table 4. In Table 4, the symbols have the following meaning:

"+++" means <1 µM; "++" means between 1 µM and 5 µM; and "+" means >5 µM.

TABLE 4

| Cmpd # | IC50 µM |
|---|---|
| 1 | ++ |
| 2 | +++ |
| 3 | +++ |
| 4 | + |
| 5 | +++ |
| 6 | + |
| 7 | ++ |
| 8 | +++ |
| 9 | +++ |
| 10 | ++ |
| 11 | +++ |
| 12 | +++ |
| 13 | +++ |
| 14 | ++ |
| 15 | ++ |
| 16 | ++ |
| 17 | +++ |
| 18 | +++ |

The invention claimed is:
1. A compound of formula IA or formula IB:

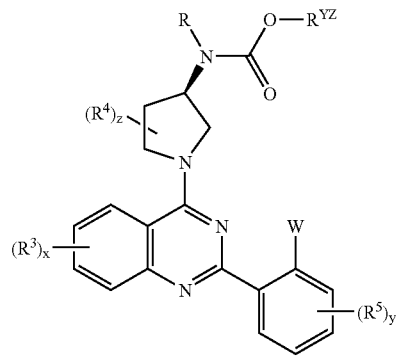

IA

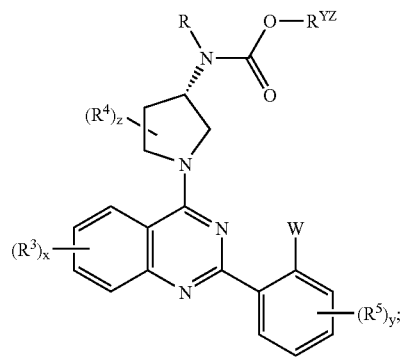

IB or a pharmaceutically acceptable salt or derivative thereof, wherein:

z is 0-3;

$R^{YZ}$ is $C_1$-$C_6$ aliphatic group, optionally substituted with $w_4$ independent occurrences of —$R^{14}$, wherein $w_4$ is 0-3;

wherein up to two methylene units in $R^{YZ}$ are optionally replaced with —NR—, —O—, —COO—, —OCO—, —NRCO—, —CONR—, —SO₂NR—, or —NRSO₂—;

x and y, each, is independently 0-4;

W is halo, —$OR^{XY}$, —CHF₂, or —CF₃;

$R^{XY}$ is hydrogen or a group selected from:

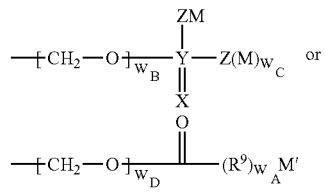

wherein:
each of $w_A$, $w_B$, $w_C$, and $w_D$ is independently 0 or 1;
each M is independently selected from hydrogen, Li, Na, K, Mg, Ca, Ba, —N($R^7$)₄, —$C_1$-$C_{12}$-alkyl, $C_2$-$C_{12}$-alkenyl, or —$R^6$; wherein 1 to 4-CH₂ radicals of the alkyl or alkenyl group, other than the —CH₂ that is bound to Z, is optionally replaced by a heteroatom group selected from O, S, S(O), S(O₂), or N($R^7$); and wherein any hydrogen in said alkyl, alkenyl or $R^6$ is optionally replaced with a substituent selected from oxo, —$OR^7$, —R⁷, —N(R⁷)₂, —N(R⁷)₃, —R⁷OH, —CN, —CO₂R⁷, —C(O)—N(R⁷)₂, S(O)₂—N(R⁷)₂, N(R⁷)—C(O)—R⁷, C(O)R⁷, —S(O)ₙ—R⁷, OCF₃, —S(O)ₙ—R⁶, —N(R⁷)—S(O)₂(R⁷), halo, —CF₃, or —NO₂;

n is 0-2;

M' is H, —C₁-C₁₂-alkyl, —C₂-C₁₂-alkenyl, or —R⁶; wherein 1 to 4-CH₂ radicals of the alkyl or alkenyl group is optionally replaced by a heteroatom group selected from O, S, S(O), S(O₂), or N(R⁷); and wherein any hydrogen in said alkyl, alkenyl or R⁶ is optionally replaced with a substituent selected from oxo, —OR⁷, —R⁷, —N(R⁷)₂, —N(R⁷)₃, —R⁷OH, —CN, —CO₂R⁷, —C(O)—N(R⁷)₂, —S(O)₂—N(R⁷)₂, —N(R⁷)—C(O)—R⁷, —C(O)R⁷, —S(O)ₙ—R⁷, —OCF₃, —S(O)ₙ—R⁶, —N(R⁷)—S(O)₂(R⁷), halo, —CF₃, or —NO₂;

Z is —CH₂₋₅-0-5-5-5-N(R⁷)₂—; or, when M is absent, then Z is hydrogen, =O, or =S;

Y is P or S, wherein when Y is S, then Z is not S;

X is O or S;

each R⁷ is independently selected from hydrogen, or C₁-C₄ aliphatic, optionally substituted with up to two Q₁;

each Q₁ is independently selected from a 3-7 membered saturated, partially saturated or unsaturated carbocyclic ring system; or a 5-7 membered saturated, partially saturated or unsaturated heterocyclic ring containing one or more heteroatom or heteroatom group selected from O, N, NH, S, SO, or SO₂; wherein Q₁ is optionally substituted with up to three substituents selected from oxo, —OH, —O(C₁-C₄ aliphatic), —C₁-C₄ aliphatic, —NH₂, —NH(C₁-C₄ aliphatic), —N(C₁-C₄ aliphatic)₂, —N(C₁-C₄ aliphatic)-C(O)—C₁-C₄ aliphatic, —(C₁-C₄ aliphatic)-OH, —CN, —CO₂H, —CO₂(C₁-C₄ aliphatic), —C(O)—NH₂, —C(O)—NH(C₁-C₄ aliphatic), —C(O)—N(C₁-C₄ aliphatic)₂, halo or —CF₃;

R⁶ is a 5-6 membered saturated, partially saturated or unsaturated carbocyclic or heterocyclic ring system, or an 8-10 membered saturated, partially saturated or unsaturated bicyclic ring system; wherein any of said heterocyclic ring systems contains one or more heteroatoms selected from O, N, S, S(O)ₙ or N(R⁷); and wherein any of said ring systems optionally contains 1 to 4 substituents independently selected from —OH, —C₁-C₄ alkyl, —O—C₁-C₄ alkyl or —O—C(O)—C₁-C₄ alkyl;

R⁹ is C(R⁷)₂, O or N(R⁷);

each occurrence of R¹⁴, R³, R⁴, and R⁵ is independently Q-Rˣ; wherein Q is a bond or is a C₁-C₆ alkylidene chain wherein up to two non-adjacent methylene units of Q are optionally and independently replaced by —NR—, —S—, —O—, —CS—, —CO₂—, —OCO—, —CO—, —COCO—, —CONR—, —NRCO—, —NRCO₂—, —SO₂NR—, —NRSO₂—, —CONRNR—, —NRCONR—, —OCONR—, —NRNR—, —NRSO₂NR—, —SO—, —SO₂—, —PO—, —PO₂—, —OP(O)(OR)—, or —POR—; and each occurrence of Rx is independently selected from —R', halogen, =NR', —NO₂, —CN, —OR', —SR', —N(R')₂, —NR'COR', —NR'CON(R')₂, —NR'CO₂R', —COR', —CO₂R', —OCOR', —CON(R')₂, —OCON(R')₂, —SOR', —SO₂R', —SO₂N(R)₂, —NR'SO₂R', —NR'SO₂N(R)₂, —COLOR', —COCH₂COR', —OP(O)(OR')₂, —P(O)(OR')₂, —OP(O)₂OR', —P(O)₂OR', —PO(R')₂, or —OPO(R')₂; and each occurrence of R is hydrogen or C₁-C₆ aliphatic group having up to three substituents; and each occurrence of R' is independently hydrogen, a C₁-C₆ aliphatic group, a 3-8-membered saturated, partially unsaturated, or fully unsaturated monocyclic ring having 0-3 heteroatoms independently selected from nitrogen, oxygen, or sulfur, or an 8-12 membered saturated, partially unsaturated, or fully unsaturated bicyclic ring system having 0-5 heteroatoms independently selected from nitrogen, oxygen, or sulfur wherein R' has up to four substituents, or R and R', two occurrences of R', or two occurrences of R', are taken together with the atom(s) to which they are bound to form a 3-12 membered saturated, partially unsaturated, or fully unsaturated monocyclic or bicyclic ring having 0-4 heteroatoms independently selected from nitrogen, oxygen, or sulfur;

provided that the following compounds are excluded:

carbamic acid, [(3R)-1-[2-(2-hydroxyphenyl)-7-methyl-4-quinazolinyl]-3-pyrrolidinyl]-, phenylmethyl ester;

carbamic acid, [(3R)-1-[2-(2-hydroxyphenyl)-7-methyl-4-quinazolinyl]-3-pyrrolidinyl]-, phenylmethyl ester, monohydrochloride;

carbamic acid, [(3S)-1-[2-(2-hydroxyphenyl)-7-methyl-4-quinazolinyl]-3-pyrrolidinyl]-, 1,1-dimethylethyl ester;

carbamic acid, [(3R)-1-[2-(2-hydroxyphenyl)-7-methyl-4-quinazolinyl]-3-pyrrolidinyl]-, 1,1-dimethylethyl ester;

carbamic acid, [(3R)-1-[6-fluoro-2-(2-hydroxyphenyl)-4-quinazolinyl]-3-pyrrolidinyl]-, 1,1-dimethylethyl ester;

carbamic acid, [(3R)-1-[2-(2-fluoro-6-hydroxyphenyl)-7-methyl-4-quinazolinyl]-3-pyrrolidinyl]-, 1,1-dimethylethyl ester;

carbamic acid, [(3R)-1-[2-(2-hydroxyphenyl)-7-methyl-4-quinazolinyl]-3-pyrrolidinyl]-, 3-pyridinylmethyl ester, trifluoroacetate (salt);

carbamic acid, [(3R)-1-[2-(2-hydroxyphenyl)-7-methyl-4-quinazolinyl]-3-pyrrolidinyl]-, 4-pyridinylmethyl ester, trifluoroacetate (salt);

carbamic acid, [(3R)-1-[2-(2-hydroxyphenyl)-7-methyl-4-quinazolinyl]-3-pyrrolidinyl]-, 1,3-benzodioxol-4-ylmethyl ester, trifluoroacetate (salt);

carbamic acid, [(3R)-1-[6-fluoro-2-(2-hydroxyphenyl)-4-quinazolinyl]-3-pyrrolidinyl]-, (tetrahydro-2H-pyran-2-yl)methyl ester, trifluoroacetate (salt); and carbamic acid, [(3R)-1-[2-(2-hydroxyphenyl)-7-methyl-4-quinazolinyl]-3-pyrrolidinyl]-, (tetrahydro-2H-pyran-2-yl)methyl ester.

2. The compound according to claim 1, wherein R is hydrogen.

3. The compound according to claim 1, wherein R' is hydrogen.

4. The compound according to claim 1, wherein W is OH.

5. The compound according to claim 1, wherein x is 0-2.

6. The compound according to claim 1, wherein x is 1.

7. The compound according to claim 1, wherein R³ is present at the 6- or 7-position of the quinazoline ring.

8. The compound according to claim 7, wherein R³ is selected from halo, —CN, —NO₂, —N(R')₂, —CH₂N(R')₂, —OR', —CH₂OR', —SR', —CH₂SR', —COOR', —NRCOR', —CON(R')₂, —OCON(R')₂, —COR', —NHCOOR', —SO₂R', —SO₂N(R')₂, or an optionally substituted group selected from C₁-C₆ aliphatic, aryl, heteroaryl, cycloaliphatic, heterocycloaliphatic, arylC₁-C₆alkyl, heteroarylC₁-C₆alkyl, cycloaliphaticC₁-C₆alkyl, or heterocycloaliphaticC₁-C₆alkyl.

9. The compound according to claim 8, wherein R³ is independently —Cl, —Br, —F, —CF₃, —OCF₃, —CH₃, —CH₂CH₃, —CN, —COOH, —NH₂, —N(CH₃)₂, —N(Et)₂, —N(iPr)₂, —O(CH₂)₂OCH₃, —CONH₂, —COOCH₃, —OH, —OCH₃, —OCH₂CH₃, —CH₂OH, —NHCOCH₃, —NHCOCH(CH₃)₂, —SO₂NH₂, —CONH(cyclopropyl), —CONHCH₃, —CONHCH₂CH₃, or an optionally substituted group selected from piperidinyl, piperazinyl, morpholino, phenyl, phenyloxy, benzyl, or benzyloxy.

10. The compound according to claim 9, wherein x is 1 and R³ is —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN.

11. The compound according to claim 1, wherein x is 1 and R³ is at the 6-position of the quinazoline ring and is —Cl, —CH₃, —CH₂CH₃, —F, —CF₃, —OCF₃, —OCH₃, or —OCH₂CH₃.

12. The compound according to claim 1, wherein x is 1 and R³ is at the 7-position of the quinazoline ring and is selected from —Cl, —CH₃, —CH₂CH₃, —F, —CF₃, —OCF₃, —CONHCH₃, —CONHCH₂CH₃, —CONH(cyclopropyl), —OCH₃, —NH₂, —OCH₂CH₃, or —CN.

13. The compound according to claim 1, wherein y is 0-4 and R⁵ is independently halo, —CN, —NO₂, —N(R')₂, —CH₂N(R')₂, —OR', —CH₂OR', —SR', —CH₂SR', —NR-COR', —CON(R')₂, —S(O)₂N(R')₂, —OCOR', —COR', —CO₂R', —OCON(R')₂, —NR'SO₂R', —OP(O)(OR')₂, —P(O)(OR')₂, —OP(O)₂OR', —P(O)₂OR', —PO(R')₂, —OPO(R')₂, or an optionally substituted group selected from C₁-C₆aliphatic, aryl, heteroaryl, cycloaliphatic, heterocycloaliphatic, arylC₁-C₆alkyl, heteroarylC₁-C₆alkyl, cycloaliphaticC₁-C₆alkyl, or heterocycloaliphaticC₁-C₆alkyl.

14. The compound according to claim 1, wherein said compound has formula IIA or formula IIB:

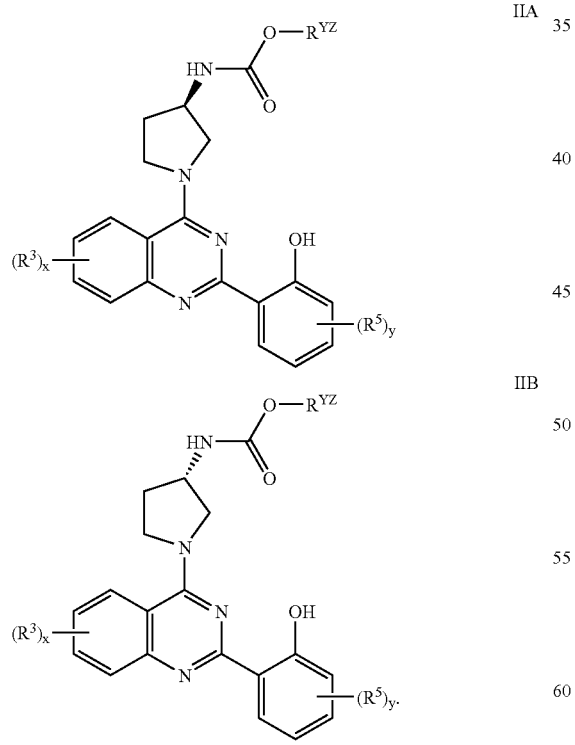

15. The compound according to claim 14, wherein in said compound of formula IIA, R^YZ is —CH₃, —CH₂CH₃, —CH(CH₃)₂, —CH₂CH₂CH₃, —CH₂CH(CH₃)₂, or —CH₂C(CH₃)₃.

16. The compound according to claim 1, wherein said compound is selected from Table 2 below:

Table 2

TABLE 2

1

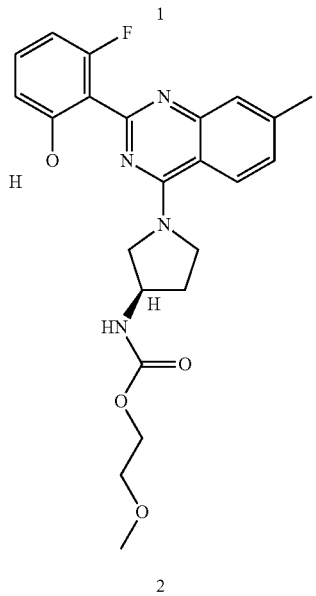

2

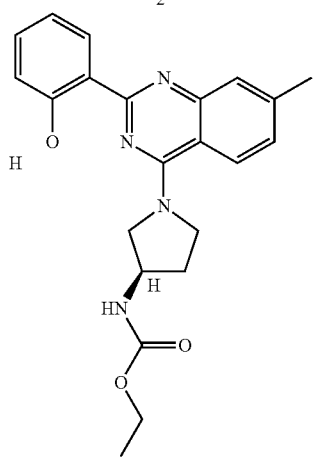

3

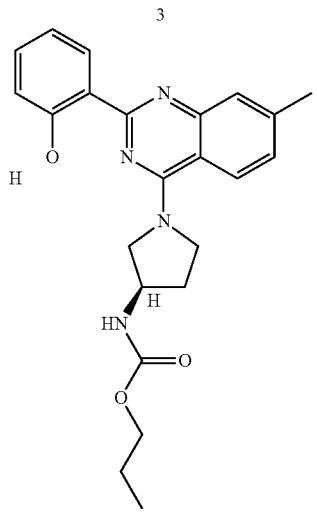

TABLE 2-continued
4
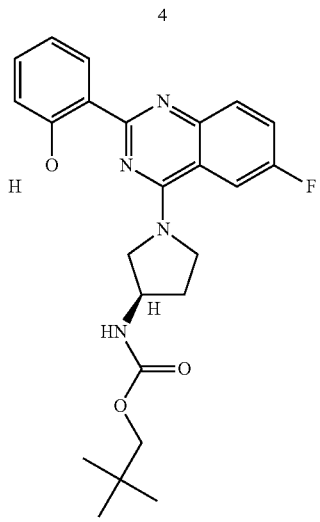
5
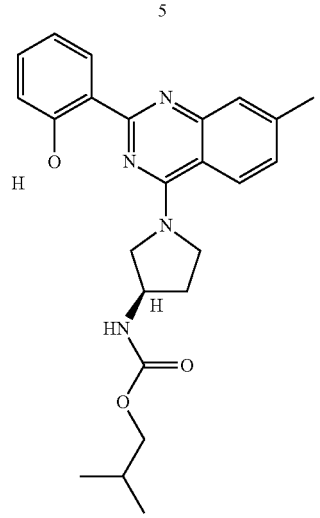
6
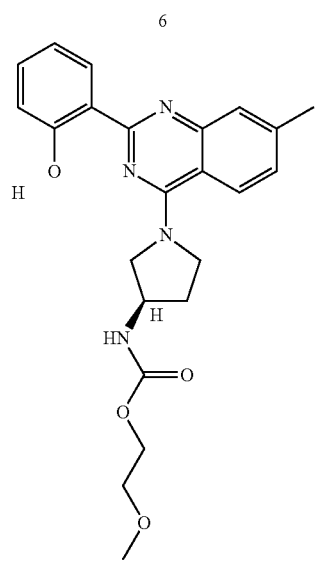
TABLE 2-continued
7
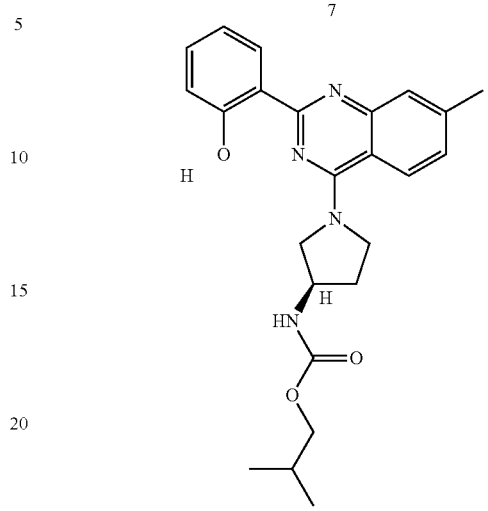
8
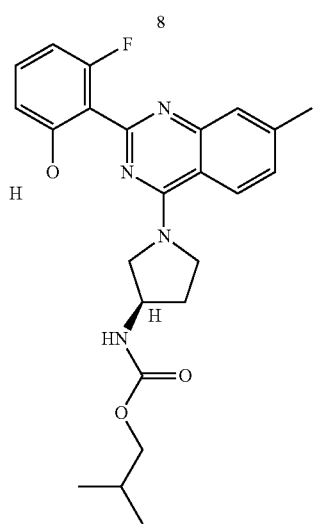
9
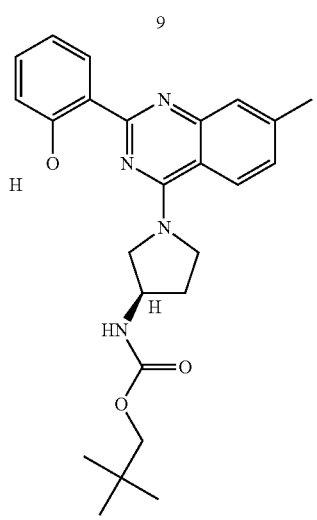

TABLE 2-continued
10
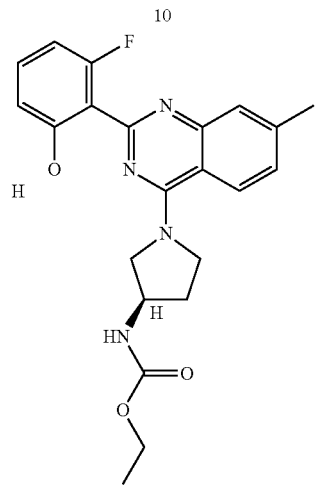
11
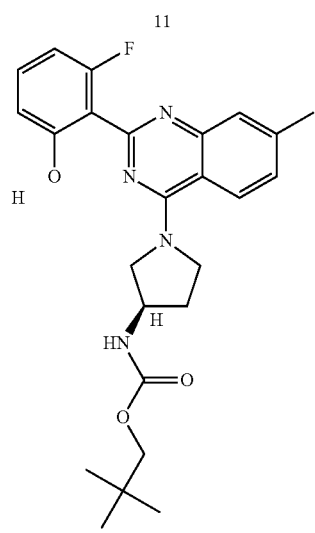
12
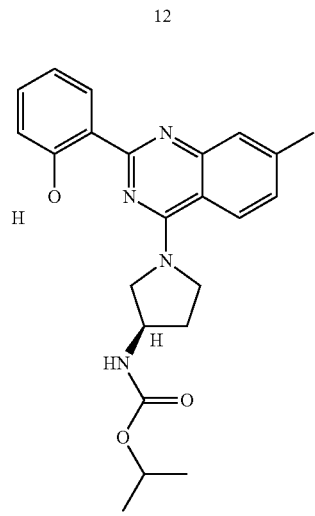
TABLE 2-continued
13
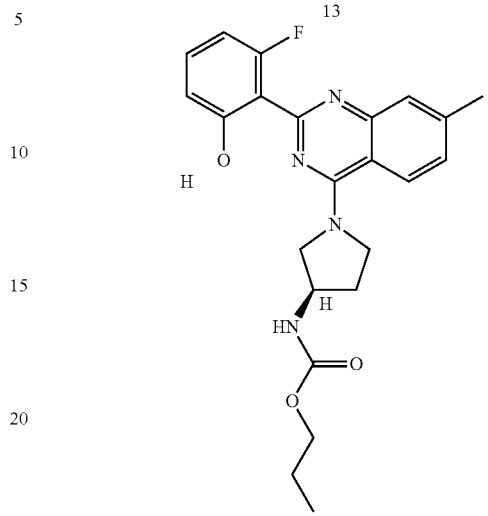
14
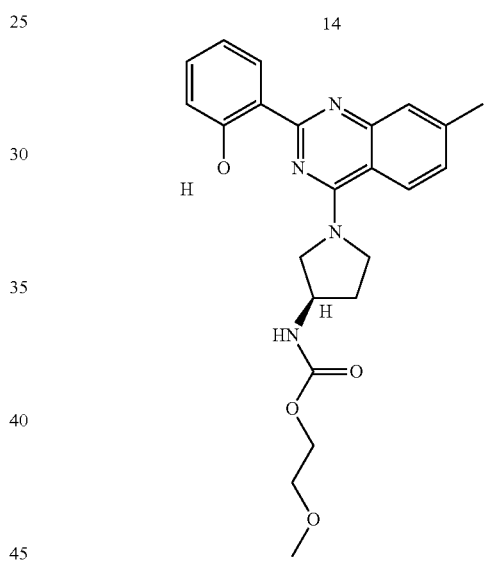
15
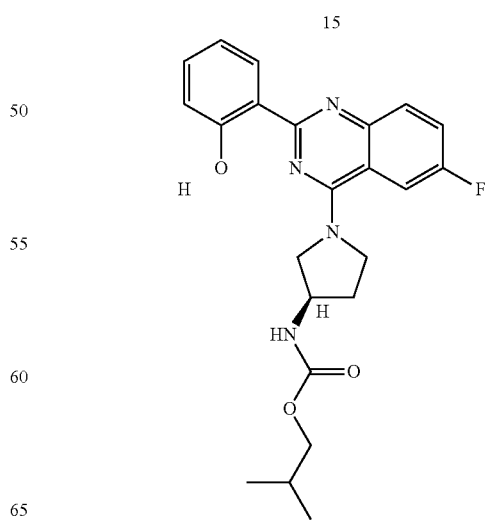

TABLE 2-continued

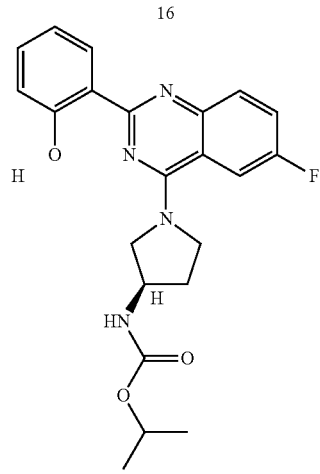

16

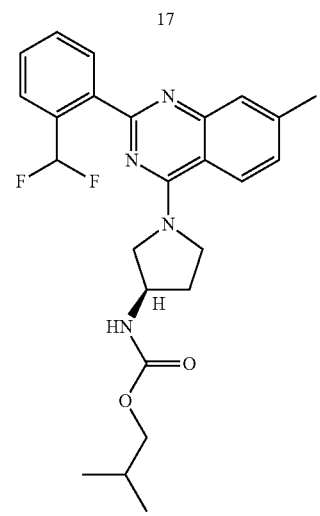

17

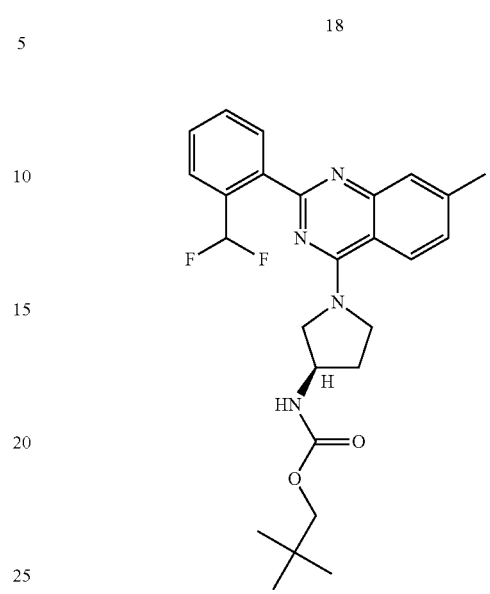

18

17. A pharmaceutical composition comprising a compound according to claim 1 or 16 and a pharmaceutically acceptable carrier.

18. A method for treating or lessening the severity of a disorder or condition selected from acute, chronic, neuropathic, inflammatory pain or severe pain, said method comprising the step of administering to a patient an effective amount of a composition according to claim 17.

* * * * *